US007553644B2

(12) United States Patent
Germino et al.

(10) Patent No.: US 7,553,644 B2
(45) Date of Patent: Jun. 30, 2009

(54) DETECTION AND TREATMENT OF POLYCYSTIC KIDNEY DISEASE

(75) Inventors: Gregory G. Germino, Chevy Chase, MD (US); Terry J. Watnick, Chevy Chase, MD (US); Bunyong Phakdeekitcharoen, Bangkok (TH)

(73) Assignee: The Johns Hopkins University School of Medicine, Baltimore, MD (US)

( * ) Notice: Subject to any disclaimer, the term of this patent is extended or adjusted under 35 U.S.C. 154(b) by 0 days.

(21) Appl. No.: 09/904,968

(22) Filed: Jul. 13, 2001

(65) Prior Publication Data

US 2003/0008288 A1 Jan. 9, 2003

Related U.S. Application Data

(60) Provisional application No. 60/218,261, filed on Jul. 13, 2000, provisional application No. 60/283,691, filed on Apr. 13, 2001.

(51) Int. Cl.
*C07H 21/04* (2006.01)
*C12P 19/34* (2006.01)
(52) U.S. Cl. .................. 435/91.2; 536/24.31; 536/24.3; 536/23.1; 435/6
(58) Field of Classification Search .................... 435/6, 435/91.1, 91.2; 536/23.1, 24.3
See application file for complete search history.

(56) References Cited

U.S. PATENT DOCUMENTS

| 5,472,672 | A | * | 12/1995 | Brennan | 422/131 |
| 5,474,796 | A | * | 12/1995 | Brennan | 427/2.13 |
| 5,654,170 | A | * | 8/1997 | Klinger et al. | 435/69.1 |
| 5,837,832 | A | * | 11/1998 | Chee et al. | 536/22.1 |
| 6,031,088 | A | | 2/2000 | Somlo et al. | |
| 6,071,717 | A | | 6/2000 | Klinger et al. | |
| 6,225,450 | B1 | * | 5/2001 | Koster | 536/22.1 |
| 6,228,591 | B1 | | 5/2001 | Somlo et al. | |
| 6,234,964 | B1 | * | 5/2001 | Iliff | 600/300 |
| 6,297,010 | B1 | * | 10/2001 | Stefano | 435/6 |
| 6,362,326 | B1 | * | 3/2002 | Sathe et al. | 536/23.5 |
| 6,380,360 | B1 | | 4/2002 | Harris et al. | |
| 6,485,960 | B1 | | 11/2002 | Harris et al. | |
| 6,656,681 | B1 | | 12/2003 | Harris et al. | |

FOREIGN PATENT DOCUMENTS

WO WO95/18225 7/1995
WO WO 97/40165 * 10/1997

OTHER PUBLICATIONS

Shapira et al PNAS vol. 88, pp. 7528-7532, Sep. 1991.*
Buck et al. Biotechniques, 528, vol. 27, No.3 1999.*
Turco et al. A novel nonsense mutation in the PKD1 gene (C3817T) is associated with autosomal dominant polysystic kidnely disease (ADPKD) in a large three-generation Italian family. Human Molecular Genetics, 1995, vol. 4, No. 8, 1331-1335.*
Rossetti, Sandro et al., "Mutation Analysis of the Entire PKD1 Gene: Genetic and Diagnostic Implications," *Am. J. Hum. Genet.*, vol. 68, 2001, pp. 46-63.
Rossetti, Sandro et al., "The Position of the Polycystic Kidney Disease 1 (PKD1) Gene Mutation Correlates With the Severity of Renal Disease," *J. Am. Soc. Nephrol*, vol. 13, 2002, pp. 1230-1237.
Bogdanova, Nadia et al., "Homologues to the First Gene for Autosomal Dominant Polycystic Kidney Disease are Pseudogenes," *Genomics*, vol. 74, 2001, pp. 333-341.
Boletta, Alessandra et al., "Polycystin-1, the Gene Product of PKD1, Induces Resistance to Apoptosis and Spontaneous Tubulogenesis in MDCK Cells," *Molecular Cell*, vol. 6, Nov. 2000, pp. 1267-1273.
The European Polycystic Kidney Disease Consortium, "The Polycystic Kidney Disease 1 Gene Encodes a 14 kb Transcript and Lies within a Duplicated Region on Chromosome 16," *Cell*, vol. 77, Jun. 17, 1994, pp. 881-894.
Phakdeekitcharoen, Bunyong et al., "Thirteen Novel Mutations of the Replicated Region of PKD1 in an Asian Population," *Kidney International*, vol. 58, 2000, pp. 1400-1412.
Phakdeekitcharoen, Bunyong et al., "Mutation Analysis of the Entire Replicated Portion of PKD1 Using Genomic DNA Samples," *J. Am. Soc. Nephrol.*, vol. 12, 2001, pp. 955-963.
Watnick, Terry J. et al., "An Unusual Pattern of Mutation in the Duplicated Portion of PKD1 is Revelaed by Use of a Novel Strategy for Mutation Detection," *Human Molecular Genetics*, vol. 6, No. 9, 1997, pp. 1473-1481.
Watnick, Terry J., "Gene Conversion is a Likely Cause of Mutation in PKD1," *Human Molecular Genetics*, vol. 7, No. 8 1998, pp. 1239-1243.
Watnick, Terry J. et al., "Somatic Mutation in Individual Liver Cysts Supports a Two-Hit Model of Cystogenesis in Autosomal Dominant Polycystic Kidney Disease," *Molecular Cell*, vol. 2, Aug. 1998, pp. 247-251.
Watnick, Terry et al., "Mutation Detection of PKD1 Identifies a Novel Mutation Common to Three Famalies with Aneurysms and/or Very-Early-Onset Disease," *Am. J. Hum. Genet.*, vol. 65, 1999, pp. 1561-1571.
Turco et al., "A novel nonsense mutation in the PKD1 gene (C3817T) is associated with autosomal dominant polycystic kidney disease (ADPKD) in a large three-generation Italian family."
Ward et al., "*Homo sapiens* polycystic kidney disease-associated protein (PKD1) gene," *Database EMBL Online!*, http://www.ebi.ac.uk, May 4, 1995.
Neophytou, et al., "Detection of a novel nonsense mutation and an intragenic polymorphism in the PKD1 gene of a Cyproit family with autosomal dominant polycystic kidney disease," *Human Genet* 98: 437-442 (1996).
Peral, et al., "Screening the 3' Region of the Polycystic Kidney Disease 1 (PKD1) Gene Reveals Six Novel Mutations," *Am. J. Human Genet.* 58: 86-96 (1996).

(Continued)

*Primary Examiner*—Juliet C Switzer
(74) *Attorney, Agent, or Firm*—DLA Piper LLP (US)

(57) ABSTRACT

Compositions useful for examining the PKD1 gene are provided. In addition, methods for detecting mutations of the PKD1 gene, which can be associated with autosomal dominant polycystic kidney disease in humans, are provided. Methods for diagnosing a mutant PKD1 gene sequence in a subject also are provided, as are methods of treating a subject having a PKD1-associated disorder.

28 Claims, 2 Drawing Sheets

OTHER PUBLICATIONS

Perrichot, et al., "DGGE Screening of PKD1 gene reveals novel mutations in a large cohort of 146 unrelated patients," *Hum Genet* 105: 231-239 (1999).

Roelfsema, et al., "Mutation Detection in the Repeated Part of the PKD1 Gene," *Am. J. Hum. Genet.* 61: 1044-1052 (1997).

Thomas et al., "Identification of Mutations in the Repeated Part of the Autosomal Dominant Polycystic Kidney Disease Type 1 Gene, PKD1, by Long-Range PCR," *Am. J. Hum. Genet.* 65: 39-49 (1999).

Liu, Wanguo, et al., "Denaturing High Performance Liquid Chromatography (DHPLC) Used in the Detection of Germline and Somatic Mutations," *Nucleic Acids Research*, vol. 26, No. 6, pp. 1396-1400, 1998.

Underhill, Peter A., et al., Detection of Numerous Y Chromosome Biallelic Polymorphisms by Denaturing High-Performance Liquid Chromatography, *Genome Research*, vol. 7, pp. 996-1005, 1997.

\* cited by examiner

SEQUENCE LISTING

<160> NUMBER OF SEQ ID NOS: 113

<210> SEQ ID NO 1
<211> LENGTH: 53522
<212> TYPE: DNA
<213> ORGANISM: Homo sapiens

<400> SEQUENCE: 1
tgtaaacttt ttgagacagc atctcaccct gttccccagg ctggagtgca gtggtgtgat        60
catggctcac tgcagcgtca acctcctggg tctacttgat ctgtaaactt cgagggaagg       120

```
tgtaataaac cctcctgcaa tgtctttgtt tttcaaaatc tttgtatttc acagtttagc        180
ttcgtgggtt gatgttctat tttgttttg tgtgtgtgtg tgtgtgtttt gtgtttttt         240 ttgagacaca gtcttgctct tgttgcccag gctggagtgc aatggtgtga tcttggctca        300
ctgcaacttc cacctcttgg gttcaagaga ttctcctgcc tcagccttcc gagtagctag        360
gattacaggc gccgccacca cccccgcta attttgtatt tttagtagag atggggtttc         420
tccatattgg tcaggctggt ctcaaactcc cgacctcagg tgatccgccc acctcagcct        480
cccaaaatgc tgggattaca ggcgtgagtc accgcacctg gccaatgttc tattttgag         540 aacacaacag ttcataatat attctacata gaccatacct gttatgtgta gataaacaga        600
ctcttttccc atttaacacc ttttgcctta ggtttatttt tctggtatca atactggcac        660
acttactttg tttgcagttt cctgtctttt ttttttttt tttttttttt gagacagagt         720
ctcactctgt cacccaggct ggagtgaagt ggcgggatct cggctcactg caacctctac        780
ctcctgggtt catgcgattc tcctgcctca gcttcccgaa tagctgagac cacaactgtg        840
tgccaccatg cccagccaat ttttgtattt ttagtagaca cggggtttca ccatactggc        900
caggatggct caatctcttg acctcgtgat ccacctgcct ccgcctccca aagtgctggg        960
attacaggca tgagccactg tgcctggcct ttttttttct ttttgagatg gagtctcact       1020
ctgtcaccca ggctggagtg cagtgggta acctcaggtc actgcgacct ccgcctcccg       1080
ggttccagtg attctcctgc ctcagcctcc cgagtagctg ggattacagg cacccaccac       1140
catgcctggc taattttgt attttagta gagacggggt tttgccacgt tggccaggtt       1200
ggtctcgaac tcttggcctc atgtgacccg cctgccttgg cctcccaaag tgctgggatt       1260
acaggtgtga gccactgtgc ctggcctggc tttcttgttt cttttctcct cttctagttt       1320
ccccctttta ggctaacaat tattcactgt taataaaaac cctcaggtct gtattttatc       1380
aagaaacatt tccctcacgt cttcttccct gaaccaaaca agatctctgg cacattttat       1440
ttgctctgtc tcaccacatg gattttgttt ttttgtttct ttgttttttg agatggagtc       1500
tcactcttgt tgcccaggct ggagtgccat ggcacaatct cagctcactg caacctccac       1560
ctcctgggtt caagcgattc tcctgtctca gcctcctgag tagctgggat tacaggcgcg       1620
tgccaccacc cccagctaat ttttgtattt ttagtagaga cggggtttca ccatgttggt       1680
caggctggtc tcgaactcct gaccttgtga tctgcccacc ttggcctccc aaagtgctgg       1740
gattacaggc atgagccacc acgcccggcc cccatggttt ttcaaatagt ttagaatttc       1800
atttccaggt aactaatttg cttctttaaa catatgtctt ttctatttaa gaaatccttt       1860
ctaaacaatt gcattttatt ccacaaccgc cttcaaacaa tcattgagac ttggttaatc       1920
tgttttgctc atttggcagc agtttcttgt ggctgtttct tccctccact ggagtccttg       1980
aatcttaagt ctgtcatttg actgcaatta aaagctgggt ttggaataca atcgcagcct       2040
taccatccac ctgctgtgtg acctggtaaa tttcttttt tttttttgag acggagtctt       2100
gctctgttgc ccaggctgga gtgcagtggc acaacctctg cctcccaggt tcaagcgatt       2160
ctactgcctc aggctcccta gtagctggga ttataggtgc ctgccaccat gcccagctga       2220 ttttgtatt tttagtagag atgaggtttc accatgttgg ctaggctggt ctcgaacttc       2280
tgatcttgtg atctgcccgc ctcggcctcc caaagtgctg ggattacagg catgagccac       2340
cactcccagc cagttctttt tttctttttt ccatttttt tttttcgag acaggatctt       2400 actcttttgc ccaggcggga gtgcagtggc acaatcacgg ctcagcgcag ccactgccta       2460
ctgggctcac acgctcctcc ggcctcagcc tctcgagtac ctgggactac aagcgtgagc       2520
```

```
cagtttggct aattttggct aattttttgta gaaacggggt ctcgccatgt tggccaggct    2580
ggtctccaac tcctggactc aagggatcca ccttcctccc cctctcaaag ttctgggatt    2640
accggagtga gccactgtgc cctgctggca aatttcttaa actgtctgtg cctcagtgac    2700
ctcatttaat aaagggaata attgtagcac acttttttcta gagctgtgaa gattcaatgg   2760
aataaataag gcaataaatg aatggatggg gaatgaagga tgtgggttc ctccctcttg     2820 tctttcaata agctctcacc atcaacctcc cattgcctgt tctctctctt cccctctct    2880 ccctctgtct ctctctcagc caggaaacct ggggtaggga ggcttggagc cagcgggtgc    2940
gtcgggaggc tgcgggtact gactcgggcc gcgcacggag atcgcgggag aaggatccac    3000
aaccgcggaa gaaggatcag ggtggagcct gtggctgctg caggaggagg aacccgccgc    3060
ctggcccaca ccacaggaga agggcggagc agatggcacc ctgcccaccg cttcccgccc    3120
acgcacttta gcctgcagcg gggcggagcg tgaaaaatag ctcgtgctcc tcggccgact    3180
ctgcagtgcg acggcggtgc ttccagacgc tccgccccac gtcgcatgcg ccccgggaac    3240
gcgtggggcg gagcttccgg aggccccgcc ctgctgccga ccctgtggag cggagggtga    3300
agcctccgga tgccagtccc tcatcgctgg cccggtcgcg ctgtggcgaa ggggcggag    3360 cctgcacccg ccccgccccc cctcgccccg tccgccccgc gccgcgcggg gaggaggagg    3420
aggagccgcg gcggggcccg cactgcagcg ccagcgtccg agcgggcggc cgagctcccg    3480
gagcggcctg gccccgagcc ccgagcgggc gtcgctcagc agcaggtcgc ggccgcagcc    3540
ccatccagcc cgcgcccgcc atgccgtccg cgggccccgc ctgagctgcg gcctccgcgc    3600
gcgggcgggc ctggggacgg cggggccatg cgcgcgctgc cctaacgatg ccgcccgccg    3660
cgcccgcccg cctggcgctg gccctgggcc tgggcctgtg gctcggggcg ctggcggggg   3720
gccccgggcg cggctgcggg ccctgcgagc ccccctgcct ctgcggccca gcgcccggcg    3780
ccgcctgccg cgtcaactgc tcgggccgcg ggctgcggac gctcggtccc gcgctgcgca    3840
tccccgcgga cgccacagcg ctgtgagtag cgggcccagc ggcacccggg agaggccgcg    3900
ggacgggcgg gcgtgggcgg gttccctggc ccggacgggg aagcaggacg cgggccagga    3960
cgctcccagg ggcgaggctc cggcgcggca cggcgggccc tgctaaataa ggaacgcctg    4020
gagccgcggt tggcacggcc ccggggagcc gaaaaccccc gggtctggag acagacgtcc    4080
caccccgggg ctctgcagac gccagcgggg gcggggcgcg gaggccgcgc tcagctggga    4140
ggacaaacag tcgctaattg gagaggaatt gggatgcggc ctgggctgc ggggtacccg    4200 gagaggtggg gatggctgta gggggcggca gggaagagtt ccaggaggtg tctggaaaag    4260
gatttgatat atgtgcaaga attgggctga tgcttaggaa ggggcgatga ggtgggtcca    4320
gaagaagggg ggtgaacggt gtgagcaaag accgtgaggc tggaggctgg ccacgggagg    4380 tgtgagggg agggcaggg tggaggtgg gctcgcgggt gggctggggt catgaagggc     4440
ctcaggcgct ctgctattgg gttccaaggc tatcctgaga acagggtga ggggggattg     4500 ccgtgggggg ttaaagcctt gtcatgttcg ctttcgggag ataaaaacaa caggtggcct    4560
ttatggagac gctgcccaga gccaggtctg tgccaggctc ctgttggggg tcgtcatgcg    4620
gaatcctgac tctgaccatc cgaggcatag ggaccgtgga gatttgcatt tcacagatga    4680
ggaaacaggt ttgagaggt gacacgacct gtcccaggca tcacagccgg gatgtgcata    4740
gcaggggttt ggaactatga ggtgcccagg acccagggtt ggattgaaaa gggcggaggg    4800
gactaagata agcagacagt tgtccccagc gctggggaga gtcttgggac cagtctgatg    4860
```

```
ccttgtattt cccaggctcc aggctcctcg ccgggacagt gtctccttgg gtgcgtgctg    4920
gatccctggg ggacgtggca catccccagg cttgctaaac attgggtggg ttctggcatt    4980
tggttttgta acgttactg gtcactcccg cctgtggcca cccttcctta ggggagccgt    5040
gtgtccttgg ggctttgctg ggtggtctcg agggtgggag aagaatgggt tctcctggac    5100
caatggagcc cgtgcccctc ggggccacat tgctcctgcg ctccctgact gcggacgcgt    5160
gtgtctcgcg gctgtctctg tggagatggc ctcctcctgc ctggcaacag cacccacaga    5220
attgcatcag acctacccca cccgttgttt gtgatgctgt agctgagggc tcctctgtct    5280
gccaggccgg tcactgggga ctctgtccag ggcctggtgg ttcctgcttc ccagcacctg    5340
atggtgtcca tgagagcagc ccctcaggag ctgtccggga gagaagggcg ctggtggctg    5400
ctgagcggag agcaaggccc gtgttctcca ggcccttggc acagcagtgg agccccgcc    5460
cctgccttgt gttgtcctct taggctctgg tcctggggtt tggaggaggg ggaccctggg    5520
agttggtggc ctgtcccagc ctgagctggc aagattccga atgccaggcc cccaagtgt    5580
gcaacagggc acagggtgac ctcatgtggg caggtgggtg ctgttctgta cacacctggg    5640
gccgccgctg ggagagttct ggaaggtggg gtgaggggac ccatggcaaa ctagggcctt    5700
aggaaggatg tgaaggccct ggctggcccc ccaggccacc ctctgtgctg tggggcagcc    5760
cagccatttt gctgtctacc ctgcaaactc tccctcgggg agacggctgg gttttccca    5820
gggaagaggg gtcaagctgg gagaggtgaa ggacacagat cacagctgct ggcaggtgtt    5880
caagggtcca agagcgttgc tgtctgggtg tcaccagtag ccttcctggg gggctcacgc    5940
aggtgcctct ccacttgtgg ctccctggct gctgaagctc agcagggaca gctgtgtcca    6000
gttccaggtg gaggacagcc ggggcttctg aggccacagc ctgccttggg ttaatgatgc    6060
tgccgagagg tggtggcttt tggaaaagat ggcgtactgc aaaacgtgct gctctgcgtg    6120
gctcgaagct tcgtggggag acgtgggcag agccgtggct gactcacaga ccccccaccc    6180
cagagcctgc cctgccctcc ctgccccgac ccttctccct cctgacccat gtgttttttt    6240
tttttttttt ttttttttgag acagagttca ctcttgttgc caaggctgga gtgcaatggc    6300
acgatctcgg ctcatggcaa cctccgcctc ctgggttcaa gcgcttttc ctgcctcagc    6360
ctcccgagta gctgggatta caggcgtgca ccaccatgcc tggctaattt tgtattttta    6420
gtagagacag ggtttctcca tattggtcag gctggtcttg aactcctgac ctcagatgat    6480
ccgcccgcct cggcctccca aagtgctggg attacaggca tgagccacca cgcccagccc    6540
tgacccatgt tttgaaccaa attccagcca ccctttatc tgcaagcatt ttggagggca    6600
tcgcaatact gcagacccac ctaacacaac agacagttcc ttcatgccac cgaaggcctg    6660
gtgtgttcac attttggtt taatagtttg aattaagagc caaataaggt ccacacactg    6720
caattagttg atgtcttttt tttttcttt tttttttttt ttttgagacg gagtcttgct    6780
cttgtctcca ggccgcagtg cagtggcatg atctcagctc accgcaacct ccgactccct    6840
ggttcaagcg attctcctgc ctcagcctcc cgagtacctg gtagctgggt tacaggcat    6900
gcaccaccgt gcccagctaa ttttgtatt tttagtagag acggggtttt actgtgttgg    6960
ccaggatggt ctcgatctcc tgacctcgtg atctgcccac ctcggcctcc caaagtgctg    7020
ggattacagg cgtgagccac cgcacccggc caatgtcttt taaaatata acttttttt    7080
ttttttttga cacggagttt cgctcttgtt gcccaggctg gagtgcagtg gcgcgatctc    7140
acctcacgga aacctccgcc tcccgggttc aagtgattct cctgcctcag cctctccagt    7200
agctgggatt acaggcatgt gccaccatgc ctggctaatt ttgtatttt aggagagacg    7260
```

```
gggtttctcc acgttggtca ggctggtctc aaactcctga cctcaggtga tccgcctgcc    7320
ttggcctccc aaagtgttgg gattacaggt gtgagccaac gcgcccagac aaaaatatat    7380
gtgtgtcttt aaggctggtc aagcaaagca gtaggactgg agaaagaatg aagaattcta    7440
cctggctgtg atcaattcgt tgtgaacacc actgtgcttg gaccagctag ctgatgtctt    7500
ttgttttgtt tgtttgaga cggagtctgg ctctgtcacc caggctggag acaatggtg     7560 tgatctcggc tcactgcagc ctccatctcc cgggttcaag cgattctcct gcctcagcct    7620
cctgagtagc tgggattaga ggcgcgcgcc accacgcccg gctaattttt aaaaatattt    7680
ttagtagaga tgggggttca ccatgttggt caggctggtc ttgaactctt ggccttaggt    7740
gatctgcttg cctcggcctc ccaaagtgct gggattacag gtgtgagtga tgtattttat    7800
ttatttattt atttatttat ttttattatt tgagatggag tctcactctg ttgcccaggc    7860
tggagtgcag cagtgccatc tcagctcact gcaagctccg cctcctgggt tcacgccatt    7920
ctcctgcctc agcctcctga gtagcctgga ctggtgcccg ccaccatgcc cagctaattt    7980
tttgtatttt tagtagagac gggatttcac cgtgttagcc aggatggtct ggatctcctg    8040
acctcgtgat cctcccgcct cagcctccca aagtgctggg attacaggct tgagccaccg    8100
cctgtctttt aaatgtccga tgatgtctag gagcttccct tcctctcttt ttccttgtgc    8160
aatttgttga agaaactggc tcctgcagcc tggatttctc gctgtgtctt gggggtgcca    8220
cctccatggt gtcacctccg tggtgctgtg agtgtgtgct ttgtgtttct tgtaaattgg    8280
tcgttggagc cgacatccca ttgtcccaga ggttgtcctg gctggcactg gcctaggtgt    8340
agatgtcatc agctcagggc ccctgctct aaaggccact tctggtgctg gttgccactc    8400
accctggctg ggggtcacct gggtctgctg ctgtctcgca aatgctgggg tccaggactg    8460
ggcacatcga gggacttggt aggtgcttgg ttcactgatg taaaatatag gagcacccgg    8520
ggccttgccc tttcccacct gcatccctga atgacaggag agtgtgggag agtgtaggga    8580
cagcaggcgc agaccccggg gcccctgcct gggattggcg tcgggaaga caggcattct    8640 ggagcgaccc ctaggcctga tgccttagag cgcaactgcc agagacacag cttccttggg    8700
gggctggcca ggccacggag gggccctggc tcccatttct ggtccctgga tcctgagagc    8760
gaggactagg gattgtcacc aaggcctcca tgagccctca gcagaaggag gccacccctc    8820
gagggctccg ttatcactgg agcccgcgtt caaccaacac gcagatgatt ctccaaggac    8880
agagatggat gatggggagg gggctggcct ggaaggaccc ccagtgcagg tgacattgaa    8940
gccaggtttc aaagctccca cagggagctg cccagagaga gtccccaagg ggcaaggtga    9000
ctcgggggca ggggtagggc ctctgtcagg agagcctagg agaggcctgt gtcttctagg    9060
aagagccctg gcagccgagc ggaggcagtg gtgaggacct gcatcctgca tgtccagctg    9120
gcctcacccg gggtccctga gccgggtctt acgtggctcc cgcactcggg cgttcagaac    9180
gtgcctgcgt gagaaacggt agtttcttta ttagacgcgg atgcaaactc gccaaacttg    9240
tggacaaaaa tgtggacaag aagtcacacg ctcactcctg tacgcgattg ccggcagggg    9300
tgggggaagg gatggggagg ctttggttgt gtctgcagca gttgggaatg tggggcaccc    9360
gagctcccac tgcagaggcg actgtggaga cagagagcac ctgcaggtca tccatgcagt    9420
atcggcttgc atccagatca tacagggaac actatgattc aacaacagac agggaccccg    9480
tttaaacatg gacaaggggt cactcacgcc tggaatccca gcagtttggg aggcagggt    9540 gggtggatcg cttgagccca ggagtttgac accagcctgg gcaacagggt gagacccgg   9600
```

```
tctctaaaaa ataaaagaac attggccggg cgtggtggta tgcatctgtg gtcccagcta   9660
ttcaggagac tgaggtggga catcacttga gccgaggagg tcaaggctgc agtgagctgt   9720
gatcacacca ctgcactcca ggctgggtca cagagcaaga ccctgtctca aaaaaaaaaa   9780
aaaaaaaaaa aaaaaatcac aggatctgaa cagagatttc tccaaagaag acgcacagat   9840
ggccaacagc gtgtgagaag atggtcggcc tcattagtca tgagggaaac gtaaatcaaa   9900
accactgtcc agccgggcgc ggtgcctcac gcctgtaatc ccagcacttt aggagagcag   9960
atggcttgag gccaggagtt tgaggccagc ctgggcaaca tagcgagacc aataaataga  10020
tattagtggt ggcgcctgta gtcccagcta gttgggaggc tgaggggga ggattccctg  10080
agtctatgag gttgagactg cagttagctg tgatggtgcc actgcactcc agcctgggcg  10140
actaggaaac ggtctttaaa aaaaaaaaa aaaacaggg tgggcgcggt ggttcacgcc  10200
tgtaatctca gcactttggg aggccaaggt gggggatca caaggtcagg agtttgtgac  10260
cagcctgacc aacatggtga aaccccgttc tactaaaaat acaaaaatta gcgaggtgtg  10320
gtcgtgggcg cctgtaatcc cagctaatta ggaggctgag gcaggagaat cacttgaacc  10380
cgggaggcgg aggttgcagt gagccaatat cacaccactg cactctagcc tggtcaacag  10440
agcgagactc tgtctcaaaa aaaaaaatg ctgagcgtgg tggcgcatgc ctgtagtctc  10500
agctactttg ggggctgagg caggagaatc gcttgaacct gggaggcaga ggtcgcagtg  10560
aggcaagatt gcaccattgc actccagcct gggagacaga gtgaaactct gtctcaaaaa  10620
gaaaaggtct aggaagagtc cgcaccctct ccccgcggtg ccacgccgg gctccgcgct  10680
gagccctctg tgttcttgtc tctccatacc tcatcacggc accgcagggt tgcagccact  10740
cctggtctca ttttacacac caggaaattg aggctctttg agaagccgtg gtgatgattt  10800
catcagcatg ctctggggca gaccctgca gccgcacagg gtgcctgggg cccacactag  10860
tgccctggtt tatagacaga cagaggtggc agtggcgctt ccgagtcggg ctgcgatgtg  10920
cttgcactcc ccgaggggct gagggccct gcgcccaggt gcagctgctt gggtgctgcc  10980
agccctcccc acctctccct ccctgccagc ccctcccacc tctccctccc tgccagcccc  11040
tcccacctct ccctccctgc cagcccctcc cacctctccc tccctgccag ccctcccac  11100
ctctccctcc ctgccagccc ctcccacctc tccctccctg cagccctc ccacctctcc  11160
ctccctgcca gccctccca cctctccctc cctccagccc ctcccacctc tccctccctg  11220
ccagccctc ccacctctcc ctccctgcca gccctcca cctctccctc ctgccagcc  11280
cctcccacct ctccctccct gccagcccct cccacctctc cctccctgcc agcccctccc  11340
acctctccct ccctgccagc cctcccacc tctccctccc tggctcatcc ctgctgtgtc  11400
ccttctctct agtttcctgt tcagtttcag gaaggaggct gggaacccag atgtagggaa  11460
tttgcgccct ggagtcagac ctgggttcac gtcccagcgc ctccacctct ggtgtgacct  11520
tggtccagtc tctcagcctc agtttcctca cctgtaaagt gggctccatg attagatgca  11580
ccctgcaggg cagtgtagca gtgacctggc tcagccactg cagcccca caatcatacc  11640
ttgttaaagt agctctgtcg gttccctcag gggttccggg ggcccattcc cctgtcctcc  11700
atgcactgtg agacctgccc tgccacagag cagagtgtaa cagcctgagg gtgagagcca  11760
gacactgtcc ctgtgcttag accagacact ggacgacggg agccagtgca gcctgggcgg  11820
gtggactcct atggacccct cagcacccag cctcggtgcc ttcagcgcag ggccgcgtgg  11880
ctgtgggggc tcacaagacc cggcccactc ctgcttgtgc ctacatctgg gtgtttgccc  11940
attggtgcct tttgacgcgt tctggtgtgt gtgagacgtg cggggctggg aagtgttggc  12000
```

```
agagccgcga gtaccgtcct cactccttt  gttcttttga cgtaagctgg cgagtggcac    12060
tgcctgagtt ccgctcagtg cccgccctga tgtgcggacc ccgctgcatt cttgctgtta    12120
ggtggtggcg gtgtgcgctg tcgctggtgg gcaccgagag tctttgggag ctttggggag    12180
gttgtgccaa gcctgagcct cgacgtcccc cttcccggct ttctgttggc tcttctgagg    12240
ccagggcatc tctatgaggg cctcctgctg gagccgtctc tgtggatctc ctctgccatc    12300
ctggcccatg agtgggtgat gcgctggcca ccatctggtg acagtggccg ggcaccgctg    12360
ccaaatgtgg gtcccgcatc tgcaagcccc tccctgggtc ccctagggta tggggtggtt    12420
ctgccactgc cctcgctccc ccaccttggg gtgcctctcc ccctgctcgt gggggagacc    12480
ctgcctggga tctgctttcc agcaaggaat atactttgga gggagacaca catgttcttt    12540
tctggagctc tgcagtggcc acggcagccc agcccgccaa gcaccctgga atgaaaacat    12600
cccgctgctg tctgggcctg gcctgcactc tgctgcctgc gctccagctg ctgaggccg     12660
ggcacgtctg cgggcacagc agcgggggcg ccacagtctc cctgcagagt gagcgcagct    12720
ggaaaatgca gctcacgccc tttcccagaa cacctcgctc ttcatggctt ggcagctgtc    12780
cttgcctagg ggccagggtg cccaggcact ggtggcagga aagggctac atctgggct      12840
gaggcgggct gggtccttt  ctccctgcag ctcccgaggc ccagccctgg cccagcctgg    12900
cattcctgac cttagcagcg ccatgatctg aagacaggct ggcttctgtg aggccacctc    12960
agaaagggct ttgtgcccag gcagaggcgg aagccagctc ttccttctgg ttgaggcagg    13020
aatgaggcca gcgctgggca gcccatgcc  cagggaacgt cacagctgtg ggagtacagg    13080
ggctccgggt tctgagcccg tccactgtgc atcgtggccc tggcctcagg atggctcgta    13140
ccatcattgg ctgtgcccac agccgagtgg gtgatgggat tccggctgcc ccgctggatc    13200
tgtgctgctg ccctctccag ggcactgctg tgcccgcaca gccgggcgca gatggccagt    13260
ttgcttgccc ccccccccac catcctcttc ctaccttggc ttcctccatt gacacactgg    13320
accctgctgg ctgcccgggg aggtgtttgg gggatggtgt tgggggagga ggagggcccc    13380
ttgagcctca gtgtgcccat caggagcgta aggtcagtgc agcacctgcc cacacaggct    13440
gtgaagggtg ggagtggaga gggatgcaag ggggtcacaa cgcctggctc catgtcagct    13500
gcgtgcaggg gcaccaggag ccggccctca ttctccccgtt gaactggaag ggtggccccg    13560
accccagcgg caggtagcat acgtatgaag cgctctcctt cctacacccc acaggtgggc    13620
tcgtctccag acgccctttt ttgagctggc tgtgttttc catctgtgta ggcaaggaca    13680
tcgcagactc ccctttctca tctccctcgt tcagcctccg aggccggagt ctccatccct    13740
gtgcctgcct gtgggtcccg ggaggacctg aggctgccca tgtcaccccc ggcatctcat    13800
cctggggaca gttcagccgt gggagggatc tgtaaggaca gaatgccgct gagcctgggg    13860
ctccccagct agtctcacac cccgtgtctg ggacccagag accctcgtgc agggctctgt    13920
tgcttggggc ctggcagcct cgtcctgtat cagaggctgc cacccccacc cctcgtgggg    13980
ccagggttgt ggccggcctc cctggccctc cccatggaag tggtaggcgg agccagcagc    14040
catctgccca gcccggggct gcactgtttt tttcaaatg  agcaccgtcc caaactgcag    14100
cccgttaatt taaacaggat catttccggc cctggaagcc gcctcactct ccttaaatag    14160
aaaggagcac agcgcagagg gaaacagatg aggtcatggc tcggctggcc cagcgaggaa    14220
ggggccgcag tggggtggc actgccgcct gtccctgtc  ctctccagcg cccacactgc    14280
agcccatttc ctcaccctgg gcctgctctc gggagggacg ggcctggggg tcctcttgct    14340
```

```
gggcggaggg gaaccagctc ctccaggaga ggacggggcc tggcaggggg catgggcct   14400 ccctgggtct ggcgtcctgt cctgccctg ccgagggagg agcggttaca taagctccgc   14460
aggcggcccc tccgagccgg tccccccagc ccagtttcca gtgaggcggc cagcgcgggc   14520
gggggtgccg ggcctggcgc acacccgctg ctgaccacac gtgtctggaa tgtgcagatg   14580
tttctttggg ggctccgtcc ggcccccaga ccccactcag catctggtct ggggagtggg   14640
cgcctggggc actcagctct gagtgtgaga ctctgaggca ggtctggttt gtctggggcc   14700
attccctctg ctgtggattg ggagggcccc gggagctgcc ccacacccag ggaagttctc   14760
ctcagtccca ctgttgcatt cccgacccc ggctccccg gcccaggagc gcctgtgggg     14820
cagaaggccc agccccaaga cttcccggcc ctgccagcct caggcttcac ccaccctcgc   14880
gccaactgtg ggcagagccc aggggaggg caggagagcc agcgcctggc tgggaacacc    14940
cctgaggggc cgaggctcca gggcgagggg gcccgacctg ggttcacac gcccgggtgg    15000 cgggcagacc cgctgcagca tgagacacgt gtcagctacc tcgggccggc aggctggccc   15060
tgctgcccac agccctggga cgtggcccca cctgtgacgg gtgtggaggg gcagcctcca   15120
ggcctggcca caccctctgc tgttgctgct cctgctccag gattggcaag ggtgctggga   15180
aggggtgaag accgtactg tggccacaca cctgggactt ccttctccac ccagtggtgc    15240
cccagcagcc gctaaggagc ccgctgggtc ccacgctagg atggtcctaa ctcctcccgc   15300
cttccagatc ggacgctcgg cgctggggac cccttgtgtc ccggggctgg ggcaccgtcc   15360
tgcccccatg ggggtgtact cctcccgaca agcttggctt cagcttccct gggagcacat   15420
cctggccctc gggcacccat caggctgtcc ctgtgcacct ggctcccacc cttccagctc   15480
atagcaggaa ctggggtgag gagtgcgtgg ggcagcaagg gcctgggacc ccagaggacc   15540
ctgcactctg ctctgtgctc ttgcctgggc ttagggccgc tcggtggtcc tgctgccaga   15600
tgcctgggcc ctgctgtgtc ccccatcctt gcagggaacc agaacgtggg ggcagggcat   15660
cagacagcgg cgatgatgtc acctggcggg tgcagaggaa gcccgagggg cggggtgggg   15720
gggctggcgc gaggctgcct ggctaggcct tggcgttccc ccagaacggc gatggcaaaa   15780
gcagatggag acgtgaaaaa gtacgggagc aagcgaggtg aggactccac ggggacccct   15840
gtgctgttcc ctgtccctga agcccacacc tgagtcctgc ccagggcaga tgcttccaca   15900
cccagggggc acctgagtcc tacccagggc agacgcttcc acaccctggg ggctggggga   15960
ctgcacctgg ctcctgtctg ggccccagct tcattccact gccctgggcc ctggagctc    16020 ggccgagcgg ggtcccaag accttgctgc atttctgggc cttgggctgg ggtgagggcc    16080
gggagaagga gccagcctgg agcctggcac gcagggagtg catggccaga accggtgaca   16140
ggcagggctg cctgctggcg tggaagaagt gtccatggca ccccaggcc tggttcacag    16200 tgggatgggc ggggagccgg ggggctctgg ggtcctcggc tgacctgccc ccaccctgc    16260 cctggcttgt cagctcccag cagcagccac tcttgatgga ttttccagaa aatgaggtgt   16320
ggccaaacat cttcaggctt ttccttcttt cctttctccc gtggcctggg tgggagctgc   16380
tccccatgcc tgggggcagg tgcgagagcc tgtgcccctc cctggggcag tttcacagct   16440
gtgtcccttc caggggcct gctgtgttc accgtggcct ctgcagcacc tctcgcccct     16500
tagggctcct cgcgcctcggg tcccggtgcc tcatttctcc ctaaagcatt ggttctgctg   16560
ccgccgcagc cgctggaaag tccctcctca ggtctaactg cagttcctca cggcacagtg   16620
ttccccctcg ggcatggtgc ttgggcagtg ggtgtgagtc cagctgcctc accctgtctc   16680
gagaatggcc tcttgctggt ctcccagcca ccaccctgtc ccaccccacg gcggggatgg   16740
```

```
tgtggatgcc tagcagcgcg gctgtgggcc cacccatcct tatgggcagt ggggagcacc    16800
tcagcccgtg tccctacctt ggtgtagagg aggggacggc agagaagcag ggttcagtta    16860 gggggggaagt ggtggccctg ccggagggggc cgttccctgt gtgcctggcc cccagatcct    16920
ctcccctccc ggagcccagg gcacaggcat aggctctctg agtgtcccac agcccctggg    16980
ggaagggaac tgcaccccca accgtgccct ccatccgcag atggaacgag aagctccggg    17040
agccagtgcc cagcgtctca tctgtctggg cacccagccc aggtgagggc ctggctccac    17100
cgtccgtggc tggtgctgct tcctggcacg gagaaggcct cggctgctct gtcccctcag    17160
ctggggtggc ctctggtccc cttctttgtt ggttcccttc tcaagctctt gccctggccc    17220
cgggccccac cgggcagcct gtgtgtgcgt ctctcctgcg ccgggtaggc tcctgtggga    17280
gcggagctcc ggtgggagga gcagggctgg aggctggcag gggctgggcg ggtgttcagg    17340
gatggaggcc gccccggctt ggggctggct gccgggtggt cattgctggg aagagcaagt    17400
ctaggcggag gcacctgctg ggtcactcgt ggggagggtg acacctgggg aagtagaggc    17460
ccgtggcagg aggtgaggcc tcgggtcct ggggagcagg ggggtggtgt gcagacctgc    17520
ggagccatag tcctgtgcca ggagcactac tgggagtgcg tgggaccagg aggggtgccc    17580
agggtgggcg gcagagtgac ccccgaggtg cttgaggccg aggggaggtg gagttctcgg    17640 tttgcccag ctctctgtct actcacctcc gcatcaccag ctccaggacc tggtttgtaa    17700
ctcgggcagc tctgaaaaga gagacatgct gccgccctgt ggtttctgtt gcttttctt    17760 cactgactac tgacatggga tgttttttcct acggctgtga ccaattgtgc ttcttctaat    17820
tgcctggttt ttctttttt gttttggag tttctcttt ctttcctccc tccctctcac    17880
cctccatcct tttttttt atttttatt tttgagatgg agcttcactc ttgcaggatg    17940
gggtgctgga gtgcagggt gcgatctcag ctcactgcaa cctctgcctc gcgggttcaa    18000
gtgattctcc tgcctaagcc tcctgagtag ctggaattac aggtgcttgc caccacgccc    18060
gactaattct gtagtttgg tagagacagg gtgtctccgt gttggtcggt ctggtcttga    18120
actcctgacc tcaggtgatg cgcccgcctc agcctcccaa agtgctggga ttacaggcag    18180
gagccattgc acccggctct ttccccttct ccttttcttc tctctctcct cccttctttt    18240
cttttctttt ctttttttt tctttgaga tggagtctcg ctctgtcacc aggctggatt    18300
gcagtggcgt gatcttggct cactgcaacc ttcgcctccc gggttcacgt gattctcctg    18360
cctcagcctc ctgagtggct ggcactacag gctcccgccg ccatgcccgg ctaattttg    18420 cattttagt agagacaggg tttcaccctg ttggccagga tggtctcgat tcttgatct    18480 catgatccac ccaccttggc ctcccaaagt tctggcatta caggagtgag ccaccgtgcc    18540
cggccatctt tctttccttg ctttctcttt gttttcttc gagaccgggt cttgctctgt    18600
cgcccaggct ggactgcagt ggcacaatca tagctcactg cagcctcgac ttccctggct    18660
caagcgatcc ttcctcctca gccccccgag tagctggaac tacagttaca cactaccatg    18720
cctggctgat tcttttttc cttgtagaga tggggtcttg ctatgctgtc catcctggtc    18780
tcaaactcct ggccttccca aagcactggg tttacaggca taagccacca cacccagttt    18840
ccttttcttc tttttaactg gaatagttga cgtttctttt attagctgtg tgtcaggagg    18900
gtatttttgg cctttagtat gtcgtgtaag ttgctagtgc ttttctgaga ttgtagtttg    18960
ttttctaatt ttatttatat tttgcgtaga agttgtgtat tttagatgga gttaggtcgg    19020
ctggtctttg atgtttttatt tattaattat gtatgtattt atttatttt gaggtagagt    19080
```

```
ctcgccgttt cacccaggct ggagtacagt gatgcgatct cagctccctg tagccttgac   19140
ctctctgggc tcaagtgatt tttctctcct ctacctcccg agtacttggg accccaggcg   19200
catgccgcca tgcctggcta atgtgtattt tttgtagata cggggtctca ctgtgttgcc   19260
cagggtggtt tcaaaatcct gggcccaggc gatccttccg tctcagctcc cacggtgctg   19320
tgttaccggc gtgtgcccag tgcctggccg tcttggaggt cttgtttctc tgggtttatg   19380
cctcgaggtg gcgcctgctc ccctgtgctc cctggtagcc tggtagtgag cctgcttctc   19440
acacagtcat acctggttgt ggtcccacag tgggaccacc ctgttgggtt cagaacagga   19500
gatgggggcc cctcgagtct gtgtgggggc tgtggacagg gttgggagac cttggctctg   19560
tgggggactg tggacagggg atgggggggcc ttggccctgc gtgggatggg ttgggggtcc   19620
gtgcccttcc tggccctggg tggacaggtc catgtggcac tcggcatagg gctgagatgg   19680
gtgcagaggg ctgaggcccc caggcctctc ctggcttggt ttccccagat gagtgttcat   19740
ttgggtcttc catcagaaag tcccctcctg acctctggga gtggggagct caagggtggg   19800
aggccatagc ttggggatgc tggcaatgtg tgggatgggc caggggaagg cctctggcct   19860
actaggggct ctggccctga cccacggcca ctcactcctc agagacgtct cccacaacct   19920
gctccgggcg ctggacgttg ggctcctggc gaacctctcg gcgctggcag agctgtgagt   19980
gtccccagt cgtgccagca tgcggggctc actccgggtg ggctggcggc accgcctctt   20040
gctgctcagc tgtgggggct tccatcagct ttgccgaatc ccccgtctct tccagggata   20100
taagcaacaa caagatttct acgttagaag aaggaatatt tgctaattta tttaatttaa   20160
gtgaaatgta agttgtggtt ctttgggtgg ggtcctggct ggaccccagg cccccaatat   20220
cccttctgcc ctcccagttg gtccgtgtcc ccttccaggc ttgagaccag atcctggggg   20280
cagttcactg cctgcttgga gcccccagt gccggcttgg ttggggcagg ggaggcggtg   20340
ctgtcagggt ggctccaggg cctggttgcc agtggggggc tggcatagac ccttcccacc   20400
agacctggtc cccaacacct gcccctgccc tgcagaaacc tgagtgggaa cccgtttgag   20460
tgtgactgtg gcctggcgtg gctgccgcga tgggcggagg agcagcaggt gcgggtggtg   20520
cagcccgagg cagccacgtg tgctgggcct ggctccctgg ctggccagcc tctgcttggc   20580
atccccttgc tggacagtgg ctgtggtgag tgccggtggg tggggccagc tctgtccttc   20640
ccagccaggt gggacctggg ccctgcagac actgggcagg gctcaggaag gcctctctgg   20700
gggggggcctc cgggccaagg gaacagcatg ggagcctgtg agtgcggcgg gcggatgtgg   20760
gggcgtgggg tggagccagg aggagcagaa cccgggtcc agtggctgcc tcttctaggt   20820
gaggagtatg tcgcctgcct ccctgacaac agctcaggca ccgtggcagc agtgtccttt   20880
tcagctgccc acgaaggcct gcttcagcca gaggcctgca gcgccttctg cttctccacc   20940
ggccagggcc tcgcagccct ctcggagcag ggctggtgcc tgtgtggggc ggcccagccc   21000
tccagtgcct cctttgcctg cctgtccctc tgctccggcc cccgccacc tctgccccc   21060
acctgtaggg gccccaccct cctccagcac gtcttccctg cctccccagg ggccaccctg   21120
gtggggcccc acgacctct ggcctctggc cagctagcag ccttccacat cgctgccccg   21180
ctccctgtca ctgccacacg ctgggacttc ggagacggct ccgccgaggt ggatgccgct   21240
gggccggctg cctcgcatcg ctatgtgctg cctgggcgct atcacgtgac ggccgtgctg   21300
gccctggggg ccggctcagc cctgctgggg acagacgtgc aggtggaagc ggcacctgcc   21360
gccctggagc tcgtgtgccc gtcctcggtg cagagtgacg agagcctcga cctcagcatc   21420
cagaaccgcg gtggttcagg cctggaggcc gcctacagca tcgtggccct gggcgaggag   21480
```

```
ccggcccgag gtgagtgtct gctgcccact cccttcctc cccagggcca tccagatggg    21540
gcagagcctg gtaccccgt cttgggccca cactgaccgt tgacaccctc gttcccaccg    21600
gtctccagcg gtgcacccgc tctgcccctc ggacacggag atcttccctg gcaacgggca    21660
ctgctaccgc ctggtggtgg agaaggcggc ctggctgcag gcgcaggagc agtgtcaggc    21720
ctgggccggg gccgccctgg caatggtgga cagtcccgcc gtgcagcgct tcctggtctc    21780
ccgggtcacc aggtgcctgc ccccaccccc cgaggggcca taggttggga gatctctgaa    21840
gcactggggg agagactgcg gctggggagt ctcaggagga aggaggtggg agctgggccg    21900
gccctggtga gcaggtggcg ccggccggtg gggccgttcc tgtcagctct gcagatgcag    21960
aggtggacat gagctggggg cagcctccgg acactcctgg gcacgccata cgggaggtgg    22020
cctgcacggg gatccctgcc ggtacccaca ggccccgtgg gtgggtgctg ctgtgagcct    22080
gggctggtgg gccctggtct ccgggctctg agcctcagtt tccccatctg gaaaggggga    22140
cagtgatggg gctcccagcg ggctgctgtg agggtgggag gatggaggag tgccctgagc    22200
cccctgccat cccacacccg cccccaggag cctagacgtg tggatcggct tctcgactgt    22260
gcagggggtg gaggtgggcc cagcgccgca gggcgaggcc ttcagcctgg agagctgcca    22320
gaactggctg cccggggagc cacacccagc cacagccgag cactgcgtcc ggctcgggcc    22380
caccgggtgg tgtaacaccg acctgtgctc agcgccgcac agctacgtct gcgagctgca    22440
gcccggaggt gtgcgggggg ccaggcaggg gcctgagacg ctggctgtgg ttaggggcct    22500
gccgagcgcc cgcggtggag cctgggctga ggaggagggg ctggtggggg ggttttcggg    22560
cggctcggtc cccagtctgt tcgtcctggt gtcctgggcc ctggcccggc gcctcactgt    22620
gcactcgcca ccccaggccc agtgcaggat gccgagaacc tcctcgtggg agcgcccagt    22680
ggggacctgc agggacccct gacgcctctg gcacagcagg acggcctctc agccccgcac    22740
gagcccgtgg aggtagtcgg cccccacgt tctacaacct gccctcctgc ctgccctgg    22800 aggccttgcc tgccctgccc actgtgggtc tcgccaaaaa acttgggggc cttaatgttg    22860
cttgtgccca gtgaagatgg ttgggaaaat ccagagtgca gagaggaaag cgtttactca    22920
cattacctcc aggcctttt tctgagcgtg tgtgagttat tcctgaaagg caggtcaggg    22980
gtcctgcccc ccatggacag tttccaccgg agtcttcctc tcgagcgaca ggagccaggc    23040
ctgtgggggt ctgatggctc gctctccttc cctcccctct tcctgggaag ttcgggtagg    23100
gggagtctgg gcttcaggct gggatggggt ctgtggagct gaggcggccc cctgcccacc    23160
aggtcatggt attcccgggc ctgcgtctga gccgtgaagc cttcctcacc acggccgaat    23220
ttgggaccca ggagctccgg cggcccgccc agctgcggct gcaggtgtac cggctcctca    23280
gcacagcagg tgggactctg ggtggtgggt ggtgggtggt gggcgccgca ggactcgggg    23340
tggcctctct gagcttttcac gtctgctggt cctgtggcca ccagagtggt tcccagtctt    23400
aggtggacag agcaggggtt ccagagacac cagctcattc caggtgtcct gggggtggat    23460
tgggtggggc ctgcctgggg gccggcctgg gtcagtcggc tggccggaga cggacgcagc    23520
actgggctgg gagtgctgcc caggtgggga gacctgtcct cacagcaagg ccaggattgc    23580
tggtgcaggc agttgggcat ctctgacggt ggcctgtggg caaatcaggg ccccaacacc    23640
ctcccctcct cacagggacc ccggagaacg gcagcgagcc tgagagcagg tccccggaca    23700
acaggaccca gctggccccc gcgtgcatgc caggggacg ctggtgccct ggagccaaca    23760
tctgcttgcc gctggacgcc tcctgccacc cccaggcctg cgccaatggc tgcacgtcag    23820
```

-continued

```
ggccagggct acccgggacc ccctatgcgc tatggagaga gttcctcttc tccgttcccg   23880
cggggccccc cgcgcagtac tcggtgtgtg gccctgacct gggtctgttc cctgcatctc   23940
ctcaggccac cttcctgtct gctgcccagg gtctgggtct gtgcaccaga cacacccagc   24000
ctgcaggccc ctcccacgtc cttgccacct ctgacctccg acctctgcag tgccctcggc   24060
cctctcccag tggagaagc tctcgcctgg gccttggca cgagctgtgc ctcctcttcc    24120
tctctcccag cacagctgct ccttcctgtc tgccaggtct tggcctgtgt cctctccccg   24180
tgtgtccccc ggtctgcaac tgtcctgcct gtccttgtca cgagcactgt ggggaggctc   24240
cttgaggtgt ggctgacgaa gcggggagcc ctgcgtgtcc accctcatcc gtcgtgcggg   24300
ggtccacggg ccatgaccgt gaggacgtga tgcagccctg cctccctctc cacaggtcac   24360
cctccacggc caggatgtcc tcatgctccc tggtgacctc gttggcttgc agcacgacg   24420 tggccctggc gccctcctgc actgctcgcc ggctcccggc caccctggtc cccgggcccc   24480
gtacctctcc gccaacgcct cgtcatggct gccccacttg ccagcccagc tggagggcac   24540
ttgggcctgc cctgcctgtg ccctgcggct gcttgcagcc acggaacagc tcaccgtgct   24600
gctgggcttg aggcccaacc ctggactgcg gctgcctggg cgctatgagg tccgggcaga   24660
ggtgggcaat ggcgtgtcca ggcacaacct ctcctgcagc tttgacgtgg tctccccagt   24720
ggctgggctg cgggtcatct accctgcccc ccgcgacggc cgcctctacg tgcccaccaa   24780
cggctcagcc ttggtgctcc aggtggactc tggtgccaac gccacggcca cggctcgctg   24840
gcctgggggc agtgtcagcg cccgctttga gaatgtctgc cctgccctgg tggccacctt   24900
cgtgcccggc tgcccctggg agaccaacga taccctgttc tcagtggtag cactgccgtg   24960
gctcagtgag ggggagcacg tggtggacgt ggtggtggaa aacagcgcca gccgggccaa   25020
cctcagcctg cgggtgacgg cggaggagcc catctgtggc ctccgcgcca cgcccagccc   25080
cgaggcccgt gtactgcagg gagtcctagt ggtgagtatg gccgaggctc caccaccagc   25140
ccccaggcag gtgcctgcag acagggtgct cacacagggc gtgaggcctg gcttcccagt   25200
gagggcagca gcccagttac tggggacgtc ggccccgggc aggtcctgct ggctggctcc   25260
tcgggctacc tggtgggctt taaattcctg gaaagtcacg gctctgacag tggctccgct   25320
aactcattcc actgtctcat ttcacaaaat gaatttaaaa ctctgctccc tgacctcaca   25380
cgagcccccg tgagtctctc acgccctctg ctgtgttctc gcctggctaa agcgagtggc   25440
ttttgaggtg gagtctgaac ccctgatggg aaactgcggg ctgccgcgg tgccaccatg    25500 ctgggtacat gggggacagg gctgtctcca tcttgcgggt acctgcctct tcaccagggg   25560
ccttgggagg ggccatcaga aatggcgtga cctgtgcagc ctgtcctggg ttctgtaagc   25620
cagtgtaggt gcctcccctc actgctccga gctctctggg tgaggagctg gggcaagagc   25680
gccgggaggg tctgagaaga ctcagagaga ggtggactct ttgtagctgg tactaggttt   25740
gctttacaga tggggaaact gaggcacaga gaggttgagg cattagtagt actacatggc   25800
tggctggaga gccggacagt gagtgtccca gcccgggctt ggctcccatg gcatgcagag   25860 cccgggcac ctcctctcct ctgtgcccg cgtgggactc tccagcccga cgggaggtgt    25920
gtccaggagg cgacaggcta agggcagagt cctccacaga gcccaggctg acaccattcc   25980
ccccgcagag gtacagcccc gtggtggagg ccggctcgga catggtcttc cggtggacca   26040
tcaacgacaa gcagtccctg accttccaga acgtggtctt caatgtcatt tatcagagcg   26100
cggcggtctt caagctctca gtaggtgggc ggggtgggg aggggagggg atggggcggg   26160
gcagggcggg ggcgggctcc accttcacct ctgccttctg ctctgcttca tgctgcccga   26220
```

```
ggacgctgcc atggctgtgg gtgagtggag ggagggacgc caatcagggc caggcctctc  26280
acctgccacc tgggctcact gacgcctgtc cctgcagctg acggcctcca accacgtgag  26340
caacgtcacc gtgaactaca acgtaaccgt ggagcggatg aacaggatgc agggtctgca  26400
ggtctccaca gtgccggccg tgctgtcccc caatgccacg ctagcactga cggcgggcgt  26460
gctggtggac tcgccgtgg aggtggcctt cctgtgagtg actcggggc cggtttgggg  26520 tgggcaccag gctcttgtcc cagccccagc ctcagccgag gaccccac atcacgggt  26580 tgcttttctg agcctcggtt tccctgtctg ttgggaggta actgggtgca caggagccct  26640
gaggctgcac gggagccggg agaggcctca gcacagccgg gtgggccctg aatggaggcc  26700
cggggcgtga ctgcagagtg gagcctcggc tgggtcccaa gcaccccctg ccccgccacc  26760
gcccacccct gtcccggttc actcactgcg tcccaccgcc ccggcaggtg gacctttggg  26820
gatggggagc aggccctcca ccagttccag cctccgtaca acgagtcctt cccggttcca  26880 gaccctcgg tgcccaggt gctggtggag cacaatgtca tgcacaccta cgctgcccca  26940
ggtgagggat gaggggtga gggggccact gcctttcagg ctctgagcac gggtccccca  27000
agctccccag tcaagctgcc cccttcctc cccaacagcc ctcactgtga cctcacctgg  27060
gctgatggct taggccctac tggggtgagg gagggggccag gcgtgggggg agtggacagg  27120
gaagctgggc ccctgaactg cgccccccgc cctccccggg cctggctctt gctgctctgc  27180
tgccccgagt gcagctgcac ttggaggcgg tgcgtcctcg ccaggcagcc ctcagtgctg  27240
ctacacctgt gctccgtccc gcacgtggct gggagcctg gaccccttaa ggctgggccg  27300
caggtgcagc cgttcaccc gggctcctca ggcgggggc ttctgccgag cgggtgggga  27360
gcaggtgggg gtgccgcggc tgcccccactc gggcctgtcc ccacaggtga gtacctcctg  27420
accgtgctgg catctaatgc cttcgagaac cggacgcagc aggtgcctgt gagcgtgcgc  27480
gcctccctgc cctccgtggc tgtgggtgtg agtgacggcg tcctggtggc cggccggccc  27540
gtcaccttct acccgcaccc gctgccctcg cctgggggtg ttcttttacac gtgggacttc  27600 ggggacggct cccctgtcct gacccagagc cagccggctg ccaaccacac ctatgcctcg  27660
aggggcacct accacgtgcg cctggaggtc aacaacacgg tgagcggtgc ggcggcccag  27720
gcggatgtgc gcgtctttga ggagctccgc ggactcagcg tggacatgag cctgccgtg  27780 gagcagggcg ccccgtggt ggtcagcgcc gcggtgcaga cgggcgacaa catcacgtgg  27840
accttcgaca tggggacgg caccgtgctg tcgggcccgg aggcaacagt ggagcatgtg  27900
tacctgcggg cacagaactg cacagtgacc gtgggtgcgg ccagccccgc cggccacctg  27960
gcccggagcc tgcacgtgct ggtcttcgtc ctggaggtgc tgcgcgttga cccgccgcc  28020 tgcatcccca cgcagcctga cgcgcggctc acggcctacg tcaccgggaa cccggcccac  28080
tacctcttcg actggacctt cggggatggc tcctccaaca cgaccgtgcg ggggtgcccg  28140
acggtgacac acaacttcac gcggagcggc acgttccccc tggcgctggt gctgtccagc  28200
cgcgtgaaca gggcgcatta cttcaccagc atctgcgtgg agccagaggt gggcaacgtc  28260
accctgcagc cagagaggca gtttgtgcag ctcggggacg aggcctggct ggtggcatgt  28320
gcctggcccc cgttcccta ccgctacacc tgggactttg caccgagga agccgcccc  28380 acccgtgcca ggggccctga ggtgacgttc atctaccgag acccaggctc ctatcttgtg  28440
acagtcaccg cgtccaacaa catctctgct gccaatgact cagccctggt ggaggtgcag  28500
gagcccgtgc tggtcaccag catcaaggtc aatggctccc ttgggctgga gctgcagcag  28560
```

```
ccgtacctgt tctctgctgt gggccgtggg cgccccgcca gctacctgtg ggatctgggg    28620
gacggtgggt ggctcgaggg tccggaggtc acccacgctt acaacagcac aggtgacttc    28680
accgttaggt ggccggctgg aatgaggtga ccgcagcga ggcctggctc aatgtgacgg     28740
tgaagcggcg cgtgcggggg ctcgtcgtca atgcaagccc cacggtggtg cccctgaatg    28800
ggagcgtgag cttcagcacg tcgctggagg ccggcagtga tgtgcgctat tcctgggtgc    28860
tctgtgaccg ctgcacgccc atccctgggg gtcctaccat ctcttacacc ttccgctccg    28920
tgggcacctt caatatcatc gtcacggctg agaacgaggt gggctccgcc caggacagca    28980
tcttcgtcta tgtcctgcag ctcatagagg ggctgcaggt ggtgggcggt ggccgctact    29040
tccccaccaa ccacacggta cagctgcagg ccgtggttag ggatggcacc aacgtctcct    29100
acagctggac tgcctggagg gacaggggcc cggccctggc cggcagcggc aaaggcttct    29160
cgctcaccgt ctcgaggccg gcacctacca tgtgcagctg cgggccacca acatgctggg    29220
cagcgcctgg gccgactgca ccatggactt cgtggagcct gtggggtggc tgatggtggc    29280
cgcctccccg aacccagctg ccgtcaacaa aagcgtcacc ctcagtgccg agctggctgg    29340
tggcagtggt gtcgtataca cttggtcctt ggaggagggg ctgagctggg agacctccga    29400
gccatttacc acccatagct tccccacacc cggcctgcac ttggtcacca tgacggcagg    29460
gaacccgctg ggctcagcca acgccaccgt ggaagtggat gtgcaggtgc ctgtgagtgg    29520
cctcagcatc agggccagcg agcccggagg cagcttcgtg gcggccgggt cctctgtgcc    29580
cttttggggg cagctggcca cgggcaccaa tgtgagctgg tgctgggctg tgcccggcgg    29640
cagcagcaag cgtggccctc atgtcaccat ggtcttcccg gatgctggca ccttctccat    29700
ccggctcaat gcctccaacg cagtcagctg ggtctcagcc acgtacaacc tcacggcgga    29760
ggagcccatc gtgggcctgg tgctgtgggc cagcagcaag gtggtggcgc ccgggcagct    29820
ggtccatttt cagatcctgc tggctgccgg ctcagctgtc accttccgcc tgcaggtcgg    29880
cggggccaac cccgaggtgc tccccgggcc ccgtttctcc cacagcttcc cccgcgtcgg    29940
agaccacgtg gtgagcgtgc ggggcaaaaa ccacgtgagc tgggcccagg cgcaggtgcg    30000
catcgtggtg ctggaggccg tgagtgggct gcaggtgccc aactgctgcg agcctggcat    30060
cgccacgggc actgagagga acttcacagc ccgcgtgcag cgcggctctc gggtcgccta    30120
cgcctggtac ttctcgctgc agaaggtcca gggcgactcg ctggtcatcc tgtcgggccg    30180
cgacgtcacc tacacgcccg tggccgcggg gctgttggag atccaggtgc gcgccttcaa    30240
cgccctgggc agtgagaacc gcacgctggt gctggaggtt caggacgccg tccagtatgt    30300
ggccctgcag agcggcccct gcttcaccaa ccgctcggcg cagtttgagg ccgccaccag    30360
ccccagcccc cggcgtgtgg cctaccactg ggactttggg gatgggtcgc cagggcagga    30420
cacagatgag cccagggccg agcactccta cctgaggcct ggggactacc gcgtgcaggt    30480
gaacgcctcc aacctggtga gcttcttcgt ggcgcaggcc acggtgaccg tccaggtgct    30540
ggcctgccgg gagccggagg tggacgtggt cctgcccctg caggtgctga tgcggcgatc    30600
acagcgcaac tacttggagg cccacgttga cctgcgcgac tgcgtcacct accagactga    30660
gtaccgctgg gaggtgtatc gcaccgccag ctgccagcgg ccggggcgcc cagcgcgtgt    30720
ggccctgccc ggcgtggacg tgagccggcc tcggctggtg ctgccgcggc tggcgctgcc    30780
tgtggggcac tactgctttg tgtttgtcgt gtcatttggg gacacgccac tgacacagag    30840
catccaggcc aatgtgacgg tggccccgga gcgcctggtg cccatcattg agggtggctc    30900
ataccgcgtg tggtcagaca cacgggacct ggtgctggat gggagcgagt cctacgaccc    30960
```

```
caacctggag gacggcgacc agacgccgct cagtttccac tgggcctgtg tggcttcgac   31020
acaggtcagt gcgtggcagg gccgtcctcc atgcccctca cccgtccaca cccatgagcc   31080
cagagaacac ccagcttgcc accagggctg gcccgtcctc agtgcctggt gggccccgtc   31140
ccagcatggg gaggggtct cccgcgctgt ctcctgggcc gggctctgct ttaaaactgg    31200
atggggctct caggccacgt cgcccttgt tctcggcctg cagagggagg ctggcggtg     31260 tgcgctgaac tttgggcccc gcgggagcag cacggtcacc attccacggg agcggctggc   31320
ggctggcgtg gagtacacct tcagcctgac cgtgtggaag gccggccgca aggaggaggc   31380
caccaaccag acggtgggtg ccgcccgccc ctcggccact tgccttggac agcccagcct   31440
ccctggtcat ctactgtttt ccgtgtttta gtgctggtgg aggccgcacg ctctcccctc   31500
tctgtttctg atgcaaattc tatgtaacac gacagcctgc ttcagctttg cttccttcca   31560
aacctgccac agttccacgt acagtcttca agccacatat gctctagtgg caaaagctac   31620
acagtcccct agcaatacca acagtgagga agagcccctt cccaccccag aggtagccac   31680
tgtccccagc ccatgtccct gttgctggat gtggtgggcc ggttctcacc ctcacgctcc   31740
cctctctgga ccggccagga ggcttggtga ccctgagccc gtggtggctg ctcctgctgc   31800
tgtcaggcgg ggcctgctgg tgccccagag tgggcgtctg ttccccagtc cctgctttcc   31860
tcagctggcc tgattggggg tcttcccaga ggggtcgtct gaggggaggg tgtgggagca   31920
ggttccatcc cagctcagcc tcctgaccca ggccctggct aagggctgca ggagtctgtg   31980
agtcaggcct acgtggcagc tgcggtcctc acacccacac atacgtctct tctcacacgc   32040
atccccccag gggccctcag tgagcattgc ctgcctcctg ctagggtcca gctgggtcca   32100
gtacaccaga acgcacactc cagtgtcctc tgccctgtgt atgcccttcc gccgtccaag   32160
ttggaaggtg gcaaaccgga tgagtatcct gggagggagt gagctcaccg gcagtggcca   32220
ggcccctggg aaacctggag tttgggagca gcatcctcca tgggtccccc agtccttcca   32280
gcaggccaaa tagacctgtg ttggaggtaa ccccactccc acgccaggtg ctgatccgga   32340
gtggccgggt gcccattgtg tccttggagt gtgtgtcctg caaggcacag gccgtgtacg   32400
aagtgagccg cagctcctac gtgtacttgg agggccgctg cctcaattgc agcagcggct   32460
ccaagcgagg ggtgagtgtt gagcggggtg tgggcgggct ggggatgggt cccatggccg   32520
aggggacggg gcctgcaggc agaagtgggg ctgacagggc agagggttgc gccccctcac   32580
caccccttct gcctgcagcg gtgggctgca cgtacgttca gcaacaagac gctggtgctg   32640
gatgagacca ccacatccac gggcagtgca ggcatgcgac tggtgctgcg gcggggcgtg   32700
ctgcgggacg gcgagggata cccttcacg ctcacggtgc tgggccgctc tggcgaggag   32760
gagggctgcg cctccatccg cctgtccccc aaccgcccgc cgctgggggg ctcttgccgc   32820
ctcttcccac tggcgctgt gcacgccctc accaccaagg tgcacttcga atgcacgggt   32880
gagtgcaggc ctgcgtgggg ggagcagcgg gatcccccga ctctgtgacg tcacggagcc   32940
ctcccgtgat gccgtgggga ccgtccctca ggctggcatg acgcggagga tgctggcgcc   33000
ccgctggtgt acgccctgct gctgcggcgc tgtcgccagg gccactgcga ggagttctgt   33060
gtctacaagg gcagcctctc cagctacgga gccgtgctgc cccgggttt caggccacac   33120 ttcgaggtgg gcctggccgt ggtggtgcag gaccagctgg gagccgctgt ggtcgccctc   33180
aacaggtgag ccaggccgtg ggagggcgcc cccgagactg ccacctgctc accacccct    33240 ctgctcgtag gtctttggcc atcaccctcc cagagcccaa cggcagcgca acggggctca   33300
```

```
cagtctggct gcacgggctc accgctagtg tgctcccagg gctgctgcgg caggccgatc    33360
cccagcacgt catcgagtac tcgttggccc tggtcaccgt gctgaacgag gtgagtgcag    33420
cctgggaggg gacgtcacat ctgctgcatg cgtgcttggg accaagacct gtacccctgc    33480
ctggagcttt gcagagggct catcccgggc cccagagata aatcccagtg accctgaagc    33540
agcaccccga ccttccgctc ccagcagcca cacccaccgg ccctctccg gcgtctgctt     33600 tccacaatgc agccccgcc caggagggcc catgtgctta ccctgttttg cccatgaaga     33660
aacagctcag tgttgtgggt cagtgcccgc atcacacagc gtctagcacg taactgcacc    33720
ccgggagtcg tgggcatctg ctggcctcct gccggcctcc tgcgctgctg acagcttgct    33780
gtgccccctg cctgccccag tacgagcggg ccctggacgt ggcgcagagc ccaagcacga    33840
gcggcagcac cgagcccaga tacgcaagaa catcacggag actctggtgt ccctgagggt    33900
ccacactgtg gatgacatcc agcagatcgc tgctgcgctg gcccagtgca tggtaggatg    33960
gccccacctg ctcaccctgc cccgcatgcc tgccagggca ctgggttcag cccccaaggg    34020
cagacgggca gcttggccga ggagctgagc ctccagcctg ggctccttcc tgccatggcg    34080
ttcctcggtc tctgacctgc ttcagtagcc tcagccgttc tgtcctgtgt gaacgcaggg    34140
tgcctctcgg gggacccagg gtgtaaagag gggcccagat gtggggaggg actaagaaga    34200
tgctgctctg tgccctccac tctcccctcc cctcccctcc ccttccctc cctagcccc     34260 tcccctcctc ccctccccta gcccttcccc tcctccctc cctagccct ttccctctt      34320 ccccccagc ccttccctc ctccctccc ctagccttc ccctcctccc ctcccctacc       34380 ccttccctc ctccctccc ctagaccttc ccctcacctc ctccgctga gccctccac       34440 tcgtccccca gcctctccct cccctagccc ctccctccc ccttcctccc ctcctccccc    34500 tccctctcctc cctccctc ttcctcccc tccctcctc ccctcctc cctctctc          34560 ccctccct cctgtccccc ctcctccct cctcctct cccctcctcc ccctcctcc          34620 tccctctcct cctcctccc tctcccct cctcctctc cctcctctc tcctccctc          34680 ctccctctcc ctcctccccc tcccctctcc ctcctccccc ctccccctc cctcctccc     34740 cctctcctcc tcccatccct cctcccatcc ctcctcccg ttcccattct ctcccctccc    34800
ccttccattt ctccctcctc ccctgcccct cctctcctcc tcacctcccc ttctccgctc   34860
ctttcttctc ctccctccct ttctctcctc cctcccctt ccctcttctc ctcttctccc    34920
cttctcctct cttttcatcc ttccttctt ccctcctttc ctcctcttt cctcttctc      34980 cccctcctc ccctcttcc tcctcccatt ccccctcct cccctccca ttccccctcc       35040 tcccctctt cctcctccca ttaccctc tctcctccc tcctcccacc ccctctcct        35100 cccggctcct ctcctcccct cctcatcccc ctcctctcct tccctcctaa ccccctcct    35160 ctcctcccct cctcatcccc ctcctctcct tccctcctcc tatccccct ctctcctcc     35220 cctcctccta ttccccctcc tctctcccc tccttcctcc tcctcctctc ccatgccccc    35280
tcctcccctc ctcccatccc ctcctcccc tcctccctcc tcccatccca tccccctcct    35340 ctcctccct tctctcccct cctctcctcc cctcctctcc tctcctcctc tcctccctc     35400 ctcccatccc cctcctccc atccccctc ctctcctccc cactcctctc ctccccactc    35460
ctctcctccc ctcatccccc tcctctctcc tccctctcc ctctctcct tcctcctcc     35520 tttcctcccc tccccctcct tcccctcct cccctcctt ctccccatcc ccttcccct     35580 tctcctcctc tccctcccc cttctctttt tccctcctcc tccttcctc ctcccctctt    35640 ctccccttt ccctttctc ttcctctcct ccccttctcc cctcctgtcc tccctcccctt   35700
```

```
tctctctttc tttcctccct ttccttctcc cctgttctcc tccctccct tctccctttt    35760 tcttccctcc tcctttcctc ccctcctcct tttctctgtt tctcttcctt tccctccac    35820 tttcccttc ctttccctc tccttcctcc ttccttcct ctcccttct cttccttttc       35880 ctctctcccc ttcttttccc tcttccctc ccctcctctt cccctcccct cctcttcccc    35940
tcccctcctc ttccctccc ctcctcttcc cctctcctcc tcttccctc cctcctctt     36000 tccctcccct cttctcctcc cctcctctcc cctcttcccc tcccctcctc ttccctcccc   36060
ttccctcccc ctcctcttcc ctccccttcc cctccctcc tcttccctcc ccttccctc    36120 ctcttccttc ctctcttccc ctccctcct cttccctccc ctcttccct cccttctct    36180 tctcctcccc ttctcttccc ctccccttt cttccctctc cttgtcttcc ctgccctcct   36240
cttccctccc ctcctcttcc ctcccctctt ccctctcct cctcttccct cccctcttcc   36300
tctttcctct tccctcccc tcctcctccc tccctttcc cctcttcccc tcccctccgc    36360
ttccctcccc tttctccccc ttctctcccc tcccctctcc ccccttctct cccctcccct   36420 ctccccttc tctcccctcc cctctccccc ttctctcccc tctcctctcc cccttctctc    36480 cccttctct cccccttctc tctcccctc tctccccctt ctctccctc ccccttctc     36540 tcccctcccc tctcccctt ctctccccct cctctcccc tgtcctctcc tctccaccct    36600 tctctccct ccctctcct ctcccttc cctctcctct ccccttctc tcccctcccc     36660 tctcctctcc ccctttct ccactccct ctctctctc ccctcctcct ccgtctcat     36720 gtgaagaggt gccttgtgtg gtcggtgggc tgcatcacgt ggtccccagg tggaggccct    36780
gggtcatgca gagccacaga aaatgcttag tgaggaggct gtggggtcc agtcaagtgg    36840 gctctccagc tgcagggctg ggggtgggag ccaggtgagg acccgtgtag agaggagggc    36900
gtgtgcaagg agtggggcca ggagcggggc tggacactgc tggctccaca caggggccca    36960
gcagggagct cgtatgccgc tcgtgcctga agcagacgct gcacaagctg gaggccatga    37020
tgctcatcct gcaggcagag accaccgcgg gcaccgtgac gcccaccgcc atcggagaca    37080
gcatcctcaa catcacaggt gccgcggccc gtgcccatg ccacccgccc gccccgtgcg     37140 gcccttcct ctgcctccct cctccccca accgcgtcgc ctttgcccca tcccatcttc    37200
gtccccctcc cctcccccca attcccatcc tcatccccct ccccaattc ccattctcct   37260 cccctcccc cttccctatt accatccctt ttctccatct ctctccctt ttctccattt    37320 ccccccccgt cctcccgtc cttttgtcca ttccctcat cttcctcatc cccctcatcc    37380
cccttcccct cccttatccc ccttcccctc cctttccccc tgctcctctt cttctccctt    37440
ctcttttctc tacccttttc cttccttttt cctccctctc cccatcatcc ccctcatctt    37500
cgtcctcatc cccatcacct tcccctccc ccctccacca ctctctctcc agcttccccc    37560
ttccttctgc ctgcacctcg ctctctgccc cctcaggttc cccctttctc ccagccccca    37620
ccctccggct ccccctttt gcctgccccc accctccctc tacctccctg tctctgcact    37680
gacctcacgc atgtctgcag gagacctcat ccacctggcc agctcggacg tgcgggcacc    37740
acagccctca gagctgggag ccgagtcacc atctcggatg gtggcgtccc aggcctacaa    37800
cctgacctct gccctcatgc gcatcctcat gcgctcccgc gtgctcaacg aggagcccct    37860
gacgctggcg ggcgaggaga tcgtggccca gggcaagcgc tcggaccgc ggagcctgct    37920 gtgctatggc ggcgcccag ggcctggctg ccacttctcc atccccgagg ctttcagcgg    37980
ggccctggcc aacctcagtg acgtggtgca gctcatcttt ctggtggact ccaatccctt    38040
```

```
tcccttttggc tatatcagca actacaccgt ctccaccaag gtggcctcga tggcattcca   38100
gacacaggcc ggcgcccaga tccccatcga gcggctggcc tcagagcgcg ccatcaccgt   38160
gaaggtgccc aacaactcgg actgggctgc ccggggccac cgcagctccg ccaactccgc   38220
caactccgtt gtggtccagc cccaggcctc cgtcggtgct gtggtcaccc tggacagcag   38280
caaccctgcg gccgggctgc atctgcagct caactatacg ctgctggacg gtgcgtgcag   38340
cgggtggggc acacgcggcc ccctggcctt gttcttgggg ggaaggcgtt tctcgtaggg   38400
cttccatggg tgtctctggt gaaatttgct ttctgtttca tgggctgctg ggggcctggc   38460
cagagaggag ctgggggcca cggagaagca ggtgccagct ctggtgcaga ggctcctatg   38520 cttttcaggcc cgtggcagag ggtgggctca ggagggccat cgtgggtgtc cccgggtgg   38580 ttgagcttcc cggcaggcgt gtgacctgcg cgttctgccc caggccacta cctgtctgag   38640
gaacctgagc cctacctggc agtctaccta cactcggagc cccggcccaa tgagcacaac   38700
tgctcggcta gcaggaggat ccgcccgag tcactccagg gtgctgacca ccggccctac   38760
accttcttca tttccccggg gtgagctctg cgggccagcc tggcagggca gggcagggca   38820
tcatgggtca gcattgcctg ggttactggc cccatgggga cggcaggcag cgaggggact   38880
ggaccgggta tgggctctga gactgcgaca tccaacctgg cggagcctgg gctcacgtcc   38940
gctacccctt ccctgcccag gagcagagac ccagcgggga gttaccatct gaacctctcc   39000
agccacttcc gctggtcggc gctgcaggtg tccgtgggcc tgtacacgtc cctgtgccag   39060
tacttcagcg aggaggacat ggtgtggcgg acagaggggc tgctgcccct ggaggagacc   39120
tcgccccgcc aggccgtctg cctcacccgc cacctcaccg ccttcggcgc cagcctcttc   39180
gtgcccccaa gccatgtccg ctttgtgttt cctgtgagtg accctgtgct cctgggagcc   39240
tctgcagagt cgaggagggc ctgggtgggc tcggctctat cctgagaagg cacagcttgc   39300
acgtgacctc ctgggcccgg cggctgtgtc ctcacaggag ccgacagcgg atgtaaacta   39360
catcgtcatg ctgacatgtg ctgtgtgcct ggtgacctac atggtcatgg ccgccatcct   39420
gcacaagctg gaccagttgg atgccagccg gggccgcgcc atcccttcct gtgggcagcg   39480
gggccgcttc aagtacgaga tcctcgtcaa gacaggctgg ggccggggct caggtgaggg   39540
gcgcagcggg gtggcagggc ctcccctgct ctcactggct gtgctggttg caccctctgg   39600
gagtgagtct cgtcgcaggc gtcagaacaa ggcagttttt gcagtgctgt gtgaagggct   39660
cgtgtgttca tcctgggaat gacctcgtga gcactcactg tccctgagga ctaggacagc   39720
tcctagctgg aagtaggtgc cagtcagtca gggtgggcag cccacgttct gcacagtagc   39780
gtggccccac aagtgacgtg agcatcgcta ccactgtggg agactgtgca tccacccgcg   39840
atcctgactg catagctcgt ctctcagacg gaggcgccag caccctcccc gtggctgttt   39900
cttcagtacc tccatttttcc tttcattgga attgcccttc tggcattccc ttttttgtttt   39960 cgttttttctt tttttagaga cggagtctca ctctgttgcc caggctggag tgcaatggca   40020
tgatcttggc tcacagcaac ttccagctcc cgggtttaag ccattcccct taagcgattc   40080
tcctgagtag ctgggagtac aggtgcacac caccacaccc agttaatttt tcaccatgtc   40140
agccaggcga actcctgacc tcaggtgatc cgcctgcctc ggcctgccag agtgctggga   40200
tgacaggtgt gagccaccac acctggctgt gttcccattt tttatctctg tgctgctttc   40260
ctcttcattg cccagttctt tcttttgatt acctacttt aaaaactgtc ggccgggcgc   40320
ggtggctcac acctgtaatc cgagcacttt gggaggccag gcaggcaaat cacgggtca   40380 ggagatcgag accatcctgg ctaacggtga aaccctgtct ctaataaaaa gtacaaaaaa   40440
```

```
attagcccgg cgtagtggca ggcgcctgta gtcccagctc cttgggagac tgaggcagga   40500
gaatggcgtg aacccgggag gcggagcttg cagtgagctg agattgcgcc actgcactcc   40560
agcctgggtg acacagcaag actccatctc aaaaaaaaaa gaaaaaaaat actgtcacct   40620
gggtctgtca ctgggagagg aggtgacaca gcttcacgct ttgcagtctg tgcatgaact   40680
gagggacggg tgtgtggtgc gggtcaccgg ttgtggcatg actgaggcgt ggacaggtgt   40740
gcagtgcggg tcactggttg tggtgtggac tgaggcgtgt gcagccatgt ttgcatgtca   40800
caagttacag ttcttttccat gtaacttaat catgtccttg aggtcctgct gttaattgga   40860
caaattgcag taaccgcagc tccttgtgta tggcagagcc gtgcaaagcc gggactgcct   40920
gtgtggctcc ttgagtgcgc acaggccaaa gctgagatga cttgcctggg atgccacacg   40980
tgttgggcag cagaccgagc ctcccacccc tccctcttgc ctcccaggta ccacggccca   41040
cgtgggcatc atgctgtatg gggtggacag ccggagcggc caccggcacc tggacggcga   41100
cagagccttc caccgcaaca gcctggacat cttccggatc gccaccccgc acagcctggg   41160
tagcgtgtgg aagatccgag tgtggcacga caacaaaggt ttgtgcggac cctgccaagc   41220
tctgcccctc tgccccgca ttggggcgcc ctgcgagcct gacctccctc ctgcgcctct   41280
gcagggctca gccctgcctg gttcctgcag cacgtcatcg tcaggacct gcagacggca   41340
cgcagcgcct tcttcctggt caatgactgg ctttcggtgg agacggaggc caacggggc   41400
ctggtggaga aggaggtgct ggccgcgagt aaggcctcgt tccatggtcc cactccgtgg   41460
gaggttgggc agggtggtcc tgccccgtgg cctcctgcag tgcggccctc cctgccttct   41520
aggcgacgca gccctttgc gcttccggcg cctgctggtg gctgagctgc agcgtggctt   41580
ctttgacaag cacatctggc tctccatatg ggaccggccg cctcgtagcc gtttcactcg   41640
catccagagg gccacctgct gcgttctcct catctgcctc ttcctgggcg ccaacgccgt   41700
gtggtacggg gctgttggcg actctgccta caggtgggtg ccgtaggggt cggggcagcc   41760
tcttcctgcc cagcccttcc tgcccctcag cctcacctgt gtggcctcct ctcctccaca   41820
cagcacgggg catgtgtcca ggctgagccc gctgagcgtc gacacagtcg ctgttggcct   41880
ggtgtccagc gtggttgtct atcccgtcta cctggccatc cttttcctct tccggatgtc   41940
ccggagcaag gtgggctggg gctggggacc cgggagtact gggaatggag cctgggcctc   42000
ggcaccatgc ctagggccgc cactttccag tgctgcagcc agagggaaag gcgtccacca   42060
aaggctgctc gggaagggtc aacacacttg agcagcctta gctagactga ccaggggaaa   42120
agagagaaga ctcagaagcc agaatggtga agaacgagg gcactttgct aagcagacgc   42180
cacggacgac tgcacagcag cacgccagat aactcagaag aagcaagcac gcggctgtgc   42240
acgcttccga aatgcactcc agaagaaaat ctcagtacat ctataggaag tgaagaggct   42300
gagttagtcc cttagaaacg tcccagtggc cgggccgggt gtggtggctc acgcctgtaa   42360
tcccaacact tcaggtggcc gaggtgggcg gatctgagtc caggagtttg agaccagcct   42420
gggcaacata gcaagacccc atctatataa aacattaaaa agggccaggc gcggtggctc   42480
acgcctgtaa tcccagcact ttgggaggcc gaggcgggca gatcacttga ggtcaggagt   42540
tcgagaccag cctggccaac acaatgaaac cccgactcta ctacaaatac aaaaacttag   42600
ctgggcatgg tggcgggcgc ctgtagtccc agctactcga gaggctgagg caggagaatg   42660
gcatgaaccc aggaggcgga gcttgcagtg agccagagatt gcgccactgc actccatcct   42720
gggcaacgga gcaagactcc atctccaaaa aaaaaaaaaa aaatcccac aaagaaaagc   42780
```

```
tcaggctcag agccttcacg atagaatttt tctaagcagt taaggaagaa ttaacaccaa   42840
tccttcacag actcttttcca agaatacagc aggtgggaac gcttcccatt catacggaaa   42900
cgggaggccg cacccttag gaatgcacac gtgggtcct caagaggtta catgcaaact    42960
aaccccagca gcacacagag aaggcgcata agccgcgacc aggaggggtt gctcccgagt   43020
ccgtggcagg aaccgaggc cacatgtggc tgctcgtatt taagttaatt aaaatggaac    43080
gatggccggg tgtggtggct cacacctgta atcccagcac tttgggaggc ggaggcgggc   43140
agatcacttg aggtcaggag ttccaagacc agcctggcca acacagtgaa accccgtctc   43200
tactaaaaat acaaaaaatt agctgggcat ggtggcaggc acctgtaatc ccagctactc   43260
aggaggctga gccaggacaa tcgcctgaac gcgggaggtg gaggttgcag tgagctgaga   43320
ttgcgccatt gcactccagc ctgggtgaca gcgagactcc atctaaaaaa gaaaatatga   43380
aatttaaaac tctgttcctt agctgcacca gtctgctgtc aagtgttcag tggcacacgt   43440
cgcgaggggc tgccatcacg gacggtgcag atgtcccata tatccagcat tctaggacat   43500
tctgtcagat ggcaccgggc tctgtcctgt ctgctgagga ggtggcttct catccctgtc   43560
ctgagcaggt ctgagctgcc gcccgctgac cactgccctc gtcctgcagg tggctgggag   43620
cccgagcccc acacctgccg ggcagcaggt gctggacatc gacagctgcc tggactcgtc   43680
cgtgctggac agctccttcc tcacgttctc aggcctccac gctgaggtga ggactctact   43740
gggggtcctg ggctgggctg ggggtcctgc cgccttggcg cagcttggac tcaagacact   43800
gtgcacctct cagcaggcct tgttggaca atgaagagt gacttgtttc tggatgattc    43860
taagaggtgg gttccctaga gaaacctcga gccctggtgc aggtcactgt gtctggggtg   43920
ccgggggtgt gcgggctgcg tgtccttgct gggtgtctgt ggctccatgt ggtcacacca   43980
cccgggagca ggtttgctcg gaagcccagg gtgtccgtgc gtgactggac gggggtgggc   44040
tgtgtgtgtg acacatcccc tggtaccttg ctgacccgcg ccacctgcag tctggtgtgc   44100
tggccctccg gcgagggaac gctcagttgg ccggacctgc tcagtgaccc gtccattgtg   44160
ggtagcaatc tgcggcagct ggcacggggc caggcgggcc atgggctggg cccagaggag   44220
gacggcttct ccctggccag ccctactcg cctgccaaat ccttctcagc atcaggtgag    44280
ctggggtgag aggaggggc tctgaagctc acccttgcag ctgggcccac cctatgcctc    44340
ctgtacctct agatgaagac ctgatccagc aggtccttgc cgagggggtc agcagcccag   44400
cccctaccca agacacccac atggaaacgg acctgctcag cagcctgtga gtgtccggct   44460 ctcggggag gggggattgc cagaggaggg gccgggactc aggccaggca gccgtggttc    44520
ccgcctgggg taggggtgggg tggggtgcca gggcagggct gtggctgcac cacttcactt   44580
ctctgaacct ctgttgtctg tggaaagagc ctcatgggat ccccagggcc ccagaaccttt   44640 ccctctaggg agggagcagg ctcatggggc tttgtaggag cagaaaggct cctgtgtgag   44700
gctggccggg gccacgtttt tatcttggtc tcagagcagt gagaaattat gggcgggttt   44760
ttaaataccc cattttttggc cgggcgcggt ggctcacacg tgtaatccca gcactttggg   44820
aggccgaggt gggcagatga cctgaggtca gcagttcgag accagcctgg ccaacatggc   44880
gaaaccccgt ctctactaaa aatacaaaaa attagccggg catgctggca ggcgcctgta   44940
gtcccagtta ctcgggagac tgaggtagga gaatcgattg aacctggtag gtgaaggttg   45000
tagtgagccg agatcgcgcc actgcactcc agcctgggca acaagagcga aactccgtct   45060
caaaaacaaa aaaattcctc aatttcttgg ttgttttgta acttatcaac aaatggtcat   45120
atagaggtta ccttgtatgt agtcacgcac atagtcacgc acatgcagc cggcggcgga   45180
```

```
gcgcacccac ggcgtgttcc cacgcgtgtg accccgggct ctgccatgcc ctcctatgct    45240
caggtgtgct gaggtccaca cggccctgcc gttgcactgc agctgcctgc aggattcagt    45300
gcagtggcat gcagtgcagg tgcggtgccc cggagccaca ggccacacca cagggcctgc    45360
atgcacaggg gctgcggtgt ctgggtttgg gtaactacgc cctgtgacat tgcacagca    45420 acagaattac ctaatgacgc atttctcaga acacatccct ggcactaagt ggtgcgtgac    45480
tgctgctttt gcatccacat ctagtttgat ttgtgtgtta ttcctttgag tgcttctcat    45540
tgttaagcaa ccaagaacta aagaggtatg aactgcccct ggactcaaac aaaaaggaaa    45600
acttcctgat ttacaaaagg cagataacca tcacatgagg gcatctttat gaataaattg    45660
ctggttggtt ttaaaaatac agagtatggg gaaatccagg ggtagtcact acatgctgac    45720
cagccccagg tatctccggc ccaaagctct gtgaaatcca gattcagtgc ttccgcgggg    45780
atttctgacg gcagctcaga ctccgcatcc acacagagcg cgtggccctc accctcccgg    45840
cttcctcaac ccttggccgt cccttgctcg gacagtgctt cgggctgacc aggtcggagg    45900
cttgggtttg tcctggaccc ctctgcgtcc ttcctcactg cagcctccag cgcgtcccgt    45960
ggctcctttc ccaacgcaga gcacggcctt ccctgcgcct gagcctgcac cctccgtcct    46020
ggcggcgcct ctgccctggc attccctgcc actccatgcc tccctattgg ccattctccg    46080
tctctgccag cgagagcctg ctccctgagt cagaccctga gtcatttgtg ttgctataaa    46140
ggaatagttg aggctgggtt atttttttatt tttatttatt tttttgagat ggagtctctg    46200
ttgcccagac tggagtgcag tcgcatgatc tcggctcact gcaaagtctg cctcccacgt    46260
tcaagcagtt atctgcctca gcctcccaag tagctaagat tacaggcgcc cgccgccaca    46320
gccggctaat ttttgtgtg tgtgttttag tagagaggag gtttcaccat cttagccagg    46380
ctggtcttga actcctgacc tcgtgatcca cccatctcag cctcccaaaa tgctgagatt    46440
acaggcgtga gccaccacgc ctgaccaagt tgaggctagg tcattttta atttttgta    46500 aagacagggt ctcactgtct ccaactcctg agctcaagtg atcctcctgc ctcagcctcc    46560
tgaagtgctg ggattacagg cttgagacac tgcgcccagc caagagtgtc ttttatcctc    46620
cgagagacag caaaacagga agcattcagt gcagtgtgac cctgggtcag gccgttcttt    46680
cggtgatggg ctgacgaggg cgcaggtacg ggagagcgtc ctgagagccc gggactcggc    46740
gtctcgcagt tggtctcgtc ctcccccctca acgtgtcttc gctgcctctg tacctcttct    46800
ctagcagctc tgggaccggg catatcagca tggtggcccg atgcagtggc acagcctcgg    46860
tggtcactgg ctcctggaga cacaagcaga tctctggcct cagggagccc tacacactgt    46920
tgggatttga aaggcattca tatgtttcct tgtccagaag ttaattttag gccataaacc    46980
tgcatgggac agacacactg gcgtctctag attgtagaga tgcttgttgg atggttgaga    47040
cccaatcata gtttgcaggg ttgaagggggg gctcattgca ccctgagaga ctgtgcactg    47100
ctgtaagggc agctggtcag gctgtgggcg atgggtttat cagcagcaag cgggcgggag    47160
agggacgcag gcggacgcct gacttcggtg cctggagtgg ctcttggttc cctggctccc    47220
agcaccactc ccactctcgt ttggggtagg gtcttccggc tttttgtcgg ggggacccctg    47280 tgacccaaga ggctcaagaa actgcccgcc caggttaaca tgggcttggc tgcaactgcc    47340
tcctggaggc cgggatgaat tcacagccta ccatgtccct caggtccagc actcctgggg    47400
agaagacaga gacgctggcg ctgcagaggc tgggggagct ggggcaccc agcccaggcc    47460 tgaactggga acagccccag gcagcgaggc tgtccaggac aggtgtgctt gcgtagcccc    47520
```

```
gggatgcccc tagccctcc  ctgtgagctg cctctcacag gtctgtctct gcttccccag  47580
gactggtgga gggtctgcgg aagcgcctgc tgccggcctg gtgtgcctcc ctggcccacg  47640
ggctcagcct gctcctggtg gctgtggctg tggctgtctc agggtgggtg ggtgcgagct  47700
tccccccggg cgtgagtgtt gcgtggctcc tgtccagcag cgccagcttc ctggcctcat  47760
tcctcggctg ggagccactg aaggtgaggg ggctgccagg ggtaggctac aggcctccat  47820
cacgggggac ccctctgaag ccaccccctc cccaggtctt gctggaagcc ctgtacttct  47880
cactggtggc caagcggctg cacccggatg aagatgacac cctggtagag agcccggctg  47940
tgacgcctgt gagcgcacgt gtgccccgcg tacgccacc  ccacggcttt gcactcttcc  48000
tggccaagga agaagcccgc aaggtcaaga ggctacatgg catgctgcgg gtgagcctgg  48060
gtgcggcctg tgcccctgcc acctccgtct cttgtctccc acctcccacc catgcacgca  48120
ggacactcct gtcccccttt cctcacctca gaaggccctt aggggttcaa tgctctgcag  48180
cctttgcccg gtctccctcc taccccacgc cccccacttg ctgccccagt ccctgccagg  48240
gcccagctcc aatgcccact cctgcctggc cctgaaggcc cctaagcacc actgcagtgg  48300
cctgtgtgtc tgcccccagg tgggtcc  ggcagggtgt gtgctgccat accctggcc   48360
aggtagagtc ttggggcgcc ccctgccagc tcaccttcct gcagccacac ctgccgcagc  48420
catggctcca gccgttgcca aagccctgct gtcactgtgg gctggggcca ggctgaccac  48480
agggccccc  cgtccaccag agcctcctgg tgtacatgct ttttctgctg gtgaccctgc  48540
tggccagcta tggggatgcc tcatgccatg ggcacgccta ccgtctgcaa agcgccatca  48600
agcaggagct gcacagccgg gccttcctgg ccatcacgcg gtacgggcat ccggtgcact  48660
ggtctgtctt ctgggcttta gttttgcctt tagtccagcc agaccctagg ggacatgtgg  48720
acatgtgtag ataccttgt ggctgctaga actggaggta ggtgctgctg gcatcagtag  48780
gcagagggga gggacacagg tccgtgtctt gcagtgcaca ggacgggccc atgacagaca  48840
actgtctgcc ccagaacatc cccaggataa ggctgagaag cccaggtcta gccgtggcca  48900
gcagggcagt gggagccatg ttccctgggt ctctggtggc cgctcactcg aggcgggcat  48960
ggggcagtag gggctggagc gtgtgactga tgctgtggca ggtctgagga gctctggcca  49020
tggatggccc acgtgctgct gccctacgtc cacgggaacc agtccagccc agagctgggg  49080
ccccacggc tgcggcaggt gcggctgcag gaaggtgagc tggcagggcg tgccccaaga  49140
cttaaatcgt tcctcttgtt gagagagcag cctttagcgg agctctggca tcagccctgc  49200
tccctagctg tgtgacctt  gccctcttaa caccgccgtt tccttctctg tatatgagag  49260
atggtaacgt tgtctaattg atggctgctg ggagggttcc ctggggtggc gccgaaccag  49320
agctcaggcg agctggccag caggaaacac tcctgttggg ttttgatgag gccctggccc  49380
cggcctgggg ctctgtgtgt ttcagcactc tacccagacc ctcccggccc cagggtccac  49440
acgtgctcgg ccgcaggagg cttcagcacc agcgattacg acgttggctg ggagagtcct  49500
cacaatggct cggggacgtg ggcctattca gcgccggatc tgctggggtg agcagagcga  49560
gggcccggg  cgtctacgcc aaggacaagg gagtagttct ccaggagtgc gcggcctcc   49620
tgaccagcct ggctccgggg tgccggaagg gctggggtgc ggcacccacg ccacccctct  49680
ccggcagggc atggtcctgg ggctcctgtg ccgtgtatga cagcggggc  tacgtgcagg  49740
agctgggcct gagcctggag gagagccgcg accggctgcg cttcctgcag ctgcacaact  49800
ggctggacaa caggtgggag ctccctcccc tgccctctcc ggggtggccg cagtcaccag  49860
ccaggagccc accctcactc ctccggcccc cgctggccta ggcggcttcc acagcccctc  49920
```

```
agccacgcct gcactgcgcg gtccccgcag ctcccgccct gccacccgct cctactgacc   49980
cgcaccctct gcgcaggagc cgcgctgtgt tcctggagct cacgcgctac agcccggccg   50040
tggggctgca cgccgccgtc acgctgcgcc tcgagttccc ggcggccggc cgcgccctgg   50100
ccgccctcag cgtccgcccc tttgcgctgc gccgcctcag cgcgggcctc tcgctgcctc   50160
tgctcacctc ggtacgcccg tccccggcca gaccccgcgc ctccaccgg cagcgtcccg    50220 cccctcgcg gggccccgcc cggcagcgtc tcacccctcg cagcgccccg ccccctcgca    50280
gcgtcccgcc ccctcgcagg gccccgcccc ggcagcgtcc cgcccctcg tagggccccg    50340 ccccggcagc gtcccgcccc ctcgcagggc cccgccccgg cagcgtccct cccgccctcc   50400
tgaccgcgcc ccccacaggt gtgcctgctg ctgttcgccg tgcacttcgc cgtggccgag   50460
gcccgtactt ggcacaggga agggcgctgg cgcgtgctgc ggctcggagc ctgggcgcgg   50520
tggctgctgg tggcgctgac ggcggccacg gcactggtac gcctcgccca gctgggtgcc   50580
gctgaccgcc agtggacccg tttcgtgcgc ggccgcccgc gccgcttcac tagcttcgac   50640
caggtggcgc agctgagctc cgcagcccgt ggcctggcgg cctcgctgct cttcctgctt   50700
ttggtcaagg tgagggctgg gccggtgggc gcggggctgg gcgcacaccc cagggctgca   50760
agcagacaga tttctcgtcc gcaggctgcc cagcagctac gcttcgtgcg ccagtggtcc   50820
gtctttggca agacattatg ccgagctctg ccagagctcc tgggggtcac cttgggcctg   50880
gtggtgctcg gggtagccta cgcccagctg gccatcctgg taggtgactg cgcggccggg   50940
gagggcgtct tagctcagct cagctcagct gtacgccctc actggtgtcg ccttcccgc    51000 agctcgtgtc ttcctgtgtg gactccctct ggagcgtggc ccaggccctg ttggtgctgt   51060 gccctggac tgggctctct accctgtgtc ctgccgagtc ctggcacctg tcaccctgc     51120 tgtgtgtggg gctctgggca ctgcggctgt ggggcgccct acggctgggg gctgttattc   51180
tccgctggcg ctaccacgcc ttgcgtggag agctgtaccg gccggcctgg gagccccagg   51240
actacgagat ggtggagttg ttcctgcgca ggctgcgcct ctggatgggc ctcagcaagg   51300
tcaaggaggt gggtacggcc cagtgggggg gagagggaca cgccctgggc tctgcccagg   51360
gtgcagccgg actgactgag cccctgtgcc gcccccagtt ccgccacaaa gtccgctttg   51420
aagggatgga gccgctgccc tctcgctcct ccaggggctc caaggtatcc ccggatgtgc   51480
ccccacccag cgctggctcc gatgcctcgc acccctccac ctcctccagc cagctggatg   51540
ggctgagcgt gagcctgggc cggctgggga caagtgtga gcctgagccc tcccgcctcc    51600
aagccgtgtt cgaggccctg ctcacccagt ttgaccgact caaccaggcc acagaggacg   51660
tctaccagct ggagcagcag ctgcacagcc tgcaaggccg caggagcagc cgggcgcccc   51720
ccggatcttc ccgtggccca tccccgggcc tgcggccagc actgcccagc cgccttgccc   51780
gggccagtcg gggtgtggac ctggccactg gccccagcag acacccctt cgggccaaga    51840 acaaggtcca ccccagcagc acttagtcct ccttcctggc ggggtgggc cgtggagtcg    51900 gagtggacac cgctcagtat tactttctgc cgctgtcaag gccagagggcc aggcagaatg   51960 gctgcacgta ggttccccag agagcaggca ggggcatctg tctgtctgtg ggcttcagca   52020
ctttaaagag gctgtgtggc caaccaggac ccagggtccc ctcccagct cccttgggaa     52080 ggacacagca gtattggacg gtttctagcc tctgagatgc taatttattt ccccgagtcc   52140
tcaggtacag cgggctgtgc ccggcccac ccctgggca gatgtccccc actgctaagg      52200
ctgctggctt cagggagggt tagcctgcac cgccgccacc ctgcccctaa gttattacct   52260
```

```
ctccagttcc taccgtactc cctgcaccgt ctcactgtgt gtctcgtgtc agtaatttat    52320
atggtgttaa aatgtgtata tttttgtatg tcactatttt cactagggct gagggcctg     52380 cgcccagagc tggcctcccc caacacctgc tgcgcttggt aggtgtggtg gcgttatggc    52440
agcccggctg ctgcttggat gcgagcttgg ccttgggccg gtgctggggg cacagctgtc    52500
tgccaggcac tctcatcacc ccagaggcct tgtcatcctc ccttgcccca ggccaggtag    52560
caagagagca gcgcccaggc ctgctggcat caggtctggg caagtagcag gactaggcat    52620
gtcagaggac cccagggtgg ttagaggaaa agactcctcc tgggggctgg ctcccagggt    52680
ggaggaaggt gactgtgtgt gtgtgtgtgt gcgcgcgcgc acgcgcgagt gtgctgtatg    52740
gcccaggcag cctcaaggcc ctcggagctg gctgtgcctg cttctgtgta ccacttctgt    52800
gggcatggcc gcttctagag cctcgacacc cccccaaccc ccgcaccaag cagacaaagt    52860
caataaaaga gctgtctgac tgcaatctgt gcctctatgt ctgtgcactg gggtcaggac    52920
tttatttatt tcactgacag gcaataccgt ccaaggccag tgcaggaggg agggccccgg    52980
cctcacacaa actcggtgaa gtcctccacc gaggagatga ggcgcttccg ctggcccacc    53040
tcatagccag gtgtgggctc ggctggagtc tgtgcagggg ctttgctatg ggacggaggg    53100
tgcaccagag gtaggctggg gttggagtag gcggcttcct cgcagatctg aaggcagagg    53160
cggcttgggc agtaagtctg ggaggcgtgg caaccgctct gcccacacac ccgccccaca    53220
gcttgggcag ccagcacacc ccgctgaggg agccccatat tccctacccg ctggcggagc    53280
gcttgatgtg gcggagcggg caatccactt ggaggggtag atatcggtgg ggttggagcg    53340
gctatgatgc acctgtgagg ccatctgggg acgtaggcag ggggtgagct cactatcagg    53400
tggcacctgg gcctgtccca ccagctcacg cctggaccca cccccactca catttgcgtg    53460
cagggccatc tggcgggcca cgaagggcag gttgcggtca gacacgatct tggccacgct    53520
gg                                                                  53522
```

<210> SEQ ID NO 2
<211> LENGTH: 4303
<212> TYPE: PRT
<213> ORGANISM: Homo sapiens

<400> SEQUENCE: 2

```
Met Pro Pro Ala Ala Pro Ala Arg Leu Ala Leu Ala Leu Gly Leu Gly
1               5                   10                  15

Leu Trp Leu Gly Ala Leu Ala Gly Gly Pro Gly Arg Gly Cys Gly Pro
            20                  25                  30

Cys Glu Pro Pro Cys Leu Cys Gly Pro Ala Gly Ala Ala Cys Arg
        35                  40                  45

Val Asn Cys Ser Gly Arg Gly Leu Arg Thr Leu Gly Pro Ala Leu Arg
    50                  55                  60

Ile Pro Ala Asp Ala Thr Glu Leu Asp Val Ser His Asn Leu Arg
65                  70                  75                  80

Ala Leu Asp Val Gly Leu Leu Ala Asn Leu Ser Ala Leu Ala Glu Leu
                85                  90                  95

Asp Ile Ser Asn Asn Lys Ile Ser Thr Leu Glu Glu Gly Ile Phe Ala
            100                 105                 110

Asn Leu Phe Asn Leu Ser Glu Ile Asn Leu Ser Gly Asn Pro Phe Glu
        115                 120                 125

Cys Asp Cys Gly Leu Ala Trp Leu Pro Gln Trp Ala Glu Glu Gln Gln
    130                 135                 140
```

-continued

```
Val Arg Val Val Gln Pro Glu Ala Ala Thr Cys Ala Gly Pro Gly Ser
145                 150                 155                 160

Leu Ala Gly Gln Pro Leu Leu Gly Ile Pro Leu Leu Asp Ser Gly Cys
                165                 170                 175

Gly Glu Glu Tyr Val Ala Cys Leu Pro Asp Asn Ser Ser Gly Thr Val
            180                 185                 190

Ala Ala Val Ser Phe Ser Ala Ala His Glu Gly Leu Leu Gln Pro Glu
        195                 200                 205

Ala Cys Ser Ala Phe Cys Phe Ser Thr Gly Gln Gly Leu Ala Ala Leu
    210                 215                 220

Ser Glu Gln Gly Trp Cys Leu Cys Gly Ala Ala Gln Pro Ser Ser Ala
225                 230                 235                 240

Ser Phe Ala Cys Leu Ser Leu Cys Ser Gly Pro Pro Ala Pro Pro Ala
                245                 250                 255

Pro Thr Cys Arg Gly Pro Thr Leu Leu Gln His Val Phe Pro Ala Ser
            260                 265                 270

Pro Gly Ala Thr Leu Val Gly Pro His Gly Pro Leu Ala Ser Gly Gln
        275                 280                 285

Leu Ala Ala Phe His Ile Ala Ala Pro Leu Pro Val Thr Asp Thr Arg
    290                 295                 300

Trp Asp Phe Gly Asp Gly Ser Ala Glu Val Asp Ala Ala Gly Pro Ala
305                 310                 315                 320

Ala Ser His Arg Tyr Val Leu Pro Gly Arg Tyr His Val Thr Ala Val
                325                 330                 335

Leu Ala Leu Gly Ala Gly Ser Ala Leu Leu Gly Thr Asp Val Gln Val
            340                 345                 350

Glu Ala Ala Pro Ala Ala Leu Glu Leu Val Cys Pro Ser Ser Val Gln
        355                 360                 365

Ser Asp Glu Ser Leu Asp Leu Ser Ile Gln Asn Arg Gly Gly Ser Gly
    370                 375                 380

Leu Glu Ala Ala Tyr Ser Ile Val Ala Leu Gly Glu Glu Pro Ala Arg
385                 390                 395                 400

Ala Val His Pro Leu Cys Pro Ser Asp Thr Glu Ile Phe Pro Gly Asn
                405                 410                 415

Gly His Cys Tyr Arg Leu Val Val Glu Lys Ala Ala Trp Leu Gln Ala
            420                 425                 430

Gln Glu Gln Cys Gln Ala Trp Ala Gly Ala Ala Leu Ala Met Val Asp
        435                 440                 445

Ser Pro Ala Val Gln Arg Phe Leu Val Ser Arg Val Thr Arg Ser Leu
    450                 455                 460

Asp Val Trp Ile Gly Phe Ser Thr Val Gln Gly Val Glu Val Gly Pro
465                 470                 475                 480

Ala Pro Gln Gly Glu Ala Phe Ser Leu Glu Ser Cys Gln Asn Trp Leu
                485                 490                 495

Pro Gly Glu Pro His Pro Ala Thr Ala Glu His Cys Val Arg Leu Gly
            500                 505                 510

Pro Thr Gly Trp Cys Asn Thr Asp Leu Cys Ser Ala Pro His Ser Tyr
        515                 520                 525

Val Cys Glu Leu Gln Pro Gly Gly Pro Val Gln Asp Ala Glu Asn Leu
    530                 535                 540

Leu Val Gly Ala Pro Ser Gly Asp Leu Gln Gly Pro Leu Thr Pro Leu
545                 550                 555                 560

Ala Gln Gln Asp Gly Leu Ser Ala Pro His Glu Pro Val Glu Val Met
```

-continued

```
                565                 570                 575
Val Phe Pro Gly Leu Arg Leu Ser Arg Glu Ala Phe Leu Thr Thr Ala
            580                 585                 590
Glu Phe Gly Thr Gln Glu Leu Arg Arg Pro Ala Gln Leu Arg Leu Gln
            595                 600                 605
Val Tyr Arg Leu Leu Ser Thr Ala Gly Thr Pro Glu Asn Gly Ser Glu
            610                 615                 620
Pro Glu Ser Arg Ser Pro Asp Asn Arg Thr Gln Leu Ala Pro Ala Cys
625                 630                 635                 640
Met Pro Gly Gly Arg Trp Cys Pro Gly Ala Asn Ile Cys Leu Pro Leu
                645                 650                 655
Asp Ala Ser Cys His Pro Gln Ala Cys Ala Asn Gly Cys Thr Ser Gly
                660                 665                 670
Pro Gly Leu Pro Gly Ala Pro Tyr Ala Leu Trp Arg Glu Phe Leu Phe
            675                 680                 685
Ser Val Pro Ala Gly Pro Ala Gln Tyr Ser Val Thr Leu His Gly
            690                 695                 700
Gln Asp Val Leu Met Leu Pro Gly Asp Leu Val Gly Leu Gln His Asp
705                 710                 715                 720
Ala Gly Pro Gly Ala Leu Leu His Cys Ser Pro Ala Pro Gly His Pro
                725                 730                 735
Gly Pro Arg Ala Pro Tyr Leu Ser Ala Asn Ala Ser Ser Trp Leu Pro
                740                 745                 750
His Leu Pro Ala Gln Leu Glu Gly Thr Trp Gly Cys Pro Ala Cys Ala
            755                 760                 765
Leu Arg Leu Leu Ala Gln Arg Glu Gln Leu Thr Val Leu Leu Gly Leu
            770                 775                 780
Arg Pro Asn Pro Gly Leu Arg Leu Pro Gly Arg Tyr Glu Val Arg Ala
785                 790                 795                 800
Glu Val Gly Asn Gly Val Ser Arg His Asn Leu Ser Cys Ser Phe Asp
                805                 810                 815
Val Val Ser Pro Val Ala Gly Leu Arg Val Ile Tyr Pro Ala Pro Arg
            820                 825                 830
Asp Gly Arg Leu Tyr Val Pro Thr Asn Gly Ser Ala Leu Val Leu Gln
            835                 840                 845
Val Asp Ser Gly Ala Asn Ala Thr Ala Thr Ala Arg Trp Pro Gly Gly
            850                 855                 860
Ser Leu Ser Ala Arg Phe Glu Asn Val Cys Pro Ala Leu Val Ala Thr
865                 870                 875                 880
Phe Val Pro Ala Cys Pro Trp Glu Thr Asn Asp Thr Leu Phe Ser Val
                885                 890                 895
Val Ala Leu Pro Trp Leu Ser Glu Gly Glu His Val Val Asp Val Val
                900                 905                 910
Val Glu Asn Ser Ala Ser Arg Ala Asn Leu Ser Leu Arg Val Thr Ala
            915                 920                 925
Glu Glu Pro Ile Cys Gly Leu Arg Ala Thr Pro Ser Pro Glu Ala Arg
            930                 935                 940
Val Leu Gln Gly Val Leu Val Arg Tyr Ser Pro Val Val Glu Ala Gly
945                 950                 955                 960
Ser Asp Met Val Phe Arg Trp Thr Ile Asn Asp Lys Gln Ser Leu Thr
                965                 970                 975
Phe Gln Asn Val Val Phe Asn Val Ile Tyr Gln Ser Ala Ala Val Phe
                980                 985                 990
```

```
Lys Leu Ser Leu Thr Ala Ser Asn  His Val Ser Asn  Val  Thr Val Asn
        995              1000              1005

Tyr Asn  Val Thr Val Glu Arg  Met Asn Arg Met  Gln  Gly Leu Gln
    1010              1015              1020

Val Ser  Thr Val Pro Ala Val  Leu Ser Pro Asn  Ala  Thr Leu Ala
    1025              1030              1035

Leu Thr  Ala Gly Val Leu Val  Asp Ser Ala Val  Glu  Val Ala Phe
    1040              1045              1050

Leu Trp  Thr Phe Gly Asp Gly  Glu Gln Ala Leu  His  Gln Phe Gln
    1055              1060              1065

Pro Pro  Tyr Asn Glu Ser Phe  Pro Val Pro Asp  Pro  Ser Val Ala
    1070              1075              1080

Gln Val  Leu Val Glu His Asn  Val Thr His Thr  Tyr  Ala Ala Pro
    1085              1090              1095

Gly Glu  Tyr Leu Leu Thr Val  Leu Ala Ser Asn  Ala  Phe Glu Asn
    1100              1105              1110

Leu Thr  Gln Gln Val Pro Val  Ser Val Arg Ala  Ser  Leu Pro Ser
    1115              1120              1125

Val Ala  Val Gly Val Ser Asp  Gly Val Leu Val  Ala  Gly Arg Pro
    1130              1135              1140

Val Thr  Phe Tyr Pro His Pro  Leu Pro Ser Pro  Gly  Gly Val Leu
    1145              1150              1155

Tyr Thr  Trp Asp Phe Gly Asp  Gly Ser Pro Val  Leu  Thr Gln Ser
    1160              1165              1170

Gln Pro  Ala Ala Asn His Thr  Tyr Ala Ser Arg  Gly  Thr Tyr His
    1175              1180              1185

Val Arg  Leu Glu Val Asn Asn  Thr Val Ser Gly  Ala  Ala Ala Gln
    1190              1195              1200

Ala Asp  Val Arg Val Phe Glu  Glu Leu Arg Gly  Leu  Ser Val Asp
    1205              1210              1215

Met Ser  Leu Ala Val Glu Gln  Gly Ala Pro Val  Val  Val Ser Ala
    1220              1225              1230

Ala Val  Gln Thr Gly Asp Asn  Ile Thr Trp Thr  Phe  Asp Met Gly
    1235              1240              1245

Asp Gly  Thr Val Leu Ser Gly  Pro Glu Ala Thr  Val  Glu His Val
    1250              1255              1260

Tyr Leu  Arg Ala Gln Asn Cys  Thr Val Thr Val  Gly  Ala Gly Ser
    1265              1270              1275

Pro Ala  Gly His Leu Ala Arg  Ser Leu His Val  Leu  Val Phe Val
    1280              1285              1290

Leu Glu  Val Leu Arg Val Glu  Pro Ala Ala Cys  Ile  Pro Thr Gln
    1295              1300              1305

Pro Asp  Ala Arg Leu Thr Ala  Tyr Val Thr Gly  Asn  Pro Ala His
    1310              1315              1320

Tyr Leu  Phe Asp Trp Thr Phe  Gly Asp Gly Ser  Ser  Asn Thr Thr
    1325              1330              1335

Val Arg  Gly Cys Pro Thr Val  Thr His Asn Phe  Thr  Arg Ser Gly
    1340              1345              1350

Thr Phe  Pro Leu Ala Leu Val  Leu Ser Ser Arg  Val  Asn Arg Ala
    1355              1360              1365

His Tyr  Phe Thr Ser Ile Cys  Val Glu Pro Glu  Val  Gly Asn Val
    1370              1375              1380
```

```
Thr Leu Gln Pro Glu Arg Gln Phe Val Gln Leu Gly Asp Glu Ala
    1385             1390             1395

Trp Leu Val Ala Cys Ala Trp Pro Pro Phe Pro Tyr Arg Tyr Thr
    1400             1405             1410

Trp Asp Phe Gly Thr Glu Glu Ala Ala Pro Thr Arg Ala Arg Gly
    1415             1420             1425

Pro Glu Val Thr Phe Ile Tyr Arg Asp Pro Gly Ser Tyr Leu Val
    1430             1435             1440

Thr Val Thr Ala Ser Asn Asn Ile Ser Ala Ala Asn Asp Ser Ala
    1445             1450             1455

Leu Val Glu Val Gln Glu Pro Val Leu Val Thr Ser Ile Lys Val
    1460             1465             1470

Asn Gly Ser Leu Gly Leu Glu Leu Gln Gln Pro Tyr Leu Phe Ser
    1475             1480             1485

Ala Val Gly Arg Gly Arg Pro Ala Ser Tyr Leu Trp Asp Leu Gly
    1490             1495             1500

Asp Gly Gly Trp Leu Glu Gly Pro Glu Val Thr His Ala Tyr Asn
    1505             1510             1515

Ser Thr Gly Asp Phe Thr Val Arg Val Ala Gly Trp Asn Glu Val
    1520             1525             1530

Ser Arg Ser Glu Ala Trp Leu Asn Val Thr Val Lys Arg Arg Val
    1535             1540             1545

Arg Gly Leu Val Val Asn Ala Ser Arg Thr Val Val Pro Leu Asn
    1550             1555             1560

Gly Ser Val Ser Phe Ser Thr Ser Leu Glu Ala Gly Ser Asp Val
    1565             1570             1575

Arg Tyr Ser Trp Val Leu Cys Asp Arg Cys Thr Pro Ile Pro Gly
    1580             1585             1590

Gly Pro Thr Ile Ser Tyr Thr Phe Arg Ser Val Gly Thr Phe Asn
    1595             1600             1605

Ile Ile Val Thr Ala Glu Asn Glu Val Gly Ser Ala Gln Asp Ser
    1610             1615             1620

Ile Phe Val Tyr Val Leu Gln Leu Ile Glu Gly Leu Gln Val Val
    1625             1630             1635

Gly Gly Gly Arg Tyr Phe Pro Thr Asn His Thr Val Gln Leu Gln
    1640             1645             1650

Ala Val Val Arg Asp Gly Thr Asn Val Ser Tyr Ser Trp Thr Ala
    1655             1660             1665

Trp Arg Asp Arg Gly Pro Ala Leu Ala Gly Ser Gly Lys Gly Phe
    1670             1675             1680

Ser Leu Thr Val Leu Glu Ala Gly Thr Tyr His Val Gln Leu Arg
    1685             1690             1695

Ala Thr Asn Met Leu Gly Ser Ala Trp Ala Asp Cys Thr Met Asp
    1700             1705             1710

Phe Val Glu Pro Val Gly Trp Leu Met Val Ala Ala Ser Pro Asn
    1715             1720             1725

Pro Ala Ala Val Asn Thr Ser Val Thr Leu Ser Ala Glu Leu Ala
    1730             1735             1740

Gly Gly Ser Gly Val Val Tyr Thr Trp Ser Leu Glu Glu Gly Leu
    1745             1750             1755

Ser Trp Glu Thr Ser Glu Pro Phe Thr Thr His Ser Phe Pro Thr
    1760             1765             1770

Pro Gly Leu His Leu Val Thr Met Thr Ala Gly Asn Pro Leu Gly
```

-continued

```
            1775                1780                1785

Ser Ala Asn Ala Thr Val Glu Val Asp Val Gln Val Pro Val Ser
    1790                1795                1800

Gly Leu Ser Ile Arg Ala Ser Glu Pro Gly Gly Ser Phe Val Ala
    1805                1810                1815

Ala Gly Ser Ser Val Pro Phe Trp Gly Gln Leu Ala Thr Gly Thr
    1820                1825                1830

Asn Val Ser Trp Cys Trp Ala Val Pro Gly Gly Ser Ser Lys Arg
    1835                1840                1845

Gly Pro His Val Thr Met Val Phe Pro Asp Ala Gly Thr Phe Ser
    1850                1855                1860

Ile Arg Leu Asn Ala Ser Asn Ala Val Ser Trp Val Ser Ala Thr
    1865                1870                1875

Tyr Asn Leu Thr Ala Glu Glu Pro Ile Val Gly Leu Val Leu Trp
    1880                1885                1890

Ala Ser Ser Lys Val Val Ala Pro Gly Gln Leu Val His Phe Gln
    1895                1900                1905

Ile Leu Leu Ala Ala Gly Ser Ala Val Thr Phe Arg Leu Gln Val
    1910                1915                1920

Gly Gly Ala Asn Pro Glu Val Leu Pro Gly Pro Arg Phe Ser His
    1925                1930                1935

Ser Phe Pro Arg Val Gly Asp His Val Val Ser Val Arg Gly Lys
    1940                1945                1950

Asn His Val Ser Trp Ala Gln Ala Gln Val Arg Ile Val Val Leu
    1955                1960                1965

Glu Ala Val Ser Gly Leu Gln Val Pro Asn Cys Cys Glu Pro Gly
    1970                1975                1980

Ile Ala Thr Gly Thr Glu Arg Asn Phe Thr Ala Arg Val Gln Arg
    1985                1990                1995

Gly Ser Arg Val Ala Tyr Ala Trp Tyr Phe Ser Leu Gln Lys Val
    2000                2005                2010

Gln Gly Asp Ser Leu Val Ile Leu Ser Gly Arg Asp Val Thr Tyr
    2015                2020                2025

Thr Pro Val Ala Ala Gly Leu Leu Glu Ile Gln Val Arg Ala Phe
    2030                2035                2040

Asn Ala Leu Gly Ser Glu Asn Arg Thr Leu Val Leu Glu Val Gln
    2045                2050                2055

Asp Ala Val Gln Tyr Val Ala Leu Gln Ser Gly Pro Cys Phe Thr
    2060                2065                2070

Asn Arg Ser Ala Gln Phe Glu Ala Ala Thr Ser Pro Ser Pro Arg
    2075                2080                2085

Arg Val Ala Tyr His Trp Asp Phe Gly Asp Gly Ser Pro Gly Gln
    2090                2095                2100

Asp Thr Asp Glu Pro Arg Ala Glu His Ser Tyr Leu Arg Pro Gly
    2105                2110                2115

Asp Tyr Arg Val Gln Val Asn Ala Ser Asn Leu Val Ser Phe Phe
    2120                2125                2130

Val Ala Gln Ala Thr Val Thr Val Gln Val Leu Ala Cys Arg Glu
    2135                2140                2145

Pro Glu Val Asp Val Val Leu Pro Leu Gln Val Leu Met Arg Arg
    2150                2155                2160

Ser Gln Arg Asn Tyr Leu Glu Ala His Val Asp Leu Arg Asp Cys
    2165                2170                2175
```

```
Val Thr Tyr Gln Thr Glu Tyr Arg Trp Glu Val Tyr Arg Thr Ala
    2180                2185                2190

Ser Cys Gln Arg Pro Gly Arg Pro Ala Arg Val Ala Leu Pro Gly
    2195                2200                2205

Val Asp Val Ser Arg Pro Arg Leu Val Leu Pro Arg Leu Ala Leu
    2210                2215                2220

Pro Val Gly His Tyr Cys Phe Val Phe Val Val Ser Phe Gly Asp
    2225                2230                2235

Thr Pro Leu Thr Gln Ser Ile Gln Ala Asn Val Thr Val Ala Pro
    2240                2245                2250

Glu Arg Leu Val Pro Ile Ile Glu Gly Gly Ser Tyr Arg Val Trp
    2255                2260                2265

Ser Asp Thr Arg Asp Leu Val Leu Asp Gly Ser Glu Ser Tyr Asp
    2270                2275                2280

Pro Asn Leu Glu Asp Gly Asp Gln Thr Pro Leu Ser Phe His Trp
    2285                2290                2295

Ala Cys Val Ala Ser Thr Gln Arg Glu Ala Gly Gly Cys Ala Leu
    2300                2305                2310

Asn Phe Gly Pro Arg Gly Ser Ser Thr Val Thr Ile Pro Arg Glu
    2315                2320                2325

Arg Leu Ala Ala Gly Val Glu Tyr Thr Phe Ser Leu Thr Val Trp
    2330                2335                2340

Lys Ala Gly Arg Lys Glu Ala Thr Asn Gln Thr Val Leu Ile
    2345                2350                2355

Arg Ser Gly Arg Val Pro Ile Val Ser Leu Glu Cys Val Ser Cys
    2360                2365                2370

Lys Ala Gln Ala Val Tyr Glu Val Ser Arg Ser Ser Tyr Val Tyr
    2375                2380                2385

Leu Glu Gly Arg Cys Leu Asn Cys Ser Ser Gly Ser Lys Arg Gly
    2390                2395                2400

Arg Trp Ala Ala Arg Thr Phe Ser Asn Lys Thr Leu Val Leu Asp
    2405                2410                2415

Glu Thr Thr Thr Ser Thr Gly Ser Ala Gly Met Arg Leu Val Leu
    2420                2425                2430

Arg Arg Gly Val Leu Arg Asp Gly Glu Gly Tyr Thr Phe Thr Leu
    2435                2440                2445

Thr Val Leu Gly Arg Ser Gly Glu Glu Glu Gly Cys Ala Ser Ile
    2450                2455                2460

Arg Leu Ser Pro Asn Arg Pro Pro Leu Gly Gly Ser Cys Arg Leu
    2465                2470                2475

Phe Pro Leu Gly Ala Val His Ala Leu Thr Thr Lys Val His Phe
    2480                2485                2490

Glu Cys Thr Gly Trp His Asp Ala Glu Asp Ala Gly Ala Pro Leu
    2495                2500                2505

Val Tyr Ala Leu Leu Leu Arg Arg Cys Arg Gln Gly His Cys Glu
    2510                2515                2520

Glu Phe Cys Val Tyr Lys Gly Ser Leu Ser Ser Tyr Gly Ala Val
    2525                2530                2535

Leu Pro Pro Gly Phe Arg Pro His Phe Glu Val Gly Leu Ala Val
    2540                2545                2550

Val Val Gln Asp Gln Leu Gly Ala Ala Val Val Ala Leu Asn Arg
    2555                2560                2565
```

-continued

```
Ser Leu Ala Ile Thr Leu Pro Glu Pro Asn Gly Ser Ala Thr Gly
    2570                2575                2580

Leu Thr Val Trp Leu His Gly Leu Thr Ala Ser Val Leu Pro Gly
    2585                2590                2595

Leu Leu Arg Gln Ala Asp Pro Gln His Val Ile Glu Tyr Ser Leu
    2600                2605                2610

Ala Leu Val Thr Val Leu Asn Glu Tyr Glu Arg Ala Leu Asp Val
    2615                2620                2625

Ala Ala Glu Pro Lys His Glu Arg Gln His Arg Ala Gln Ile Arg
    2630                2635                2640

Lys Asn Ile Thr Glu Thr Leu Val Ser Leu Arg Val His Thr Val
    2645                2650                2655

Asp Asp Ile Gln Gln Ile Ala Ala Ala Leu Ala Gln Cys Met Gly
    2660                2665                2670

Pro Ser Arg Glu Leu Val Cys Arg Ser Cys Leu Lys Gln Thr Leu
    2675                2680                2685

His Lys Leu Glu Ala Met Met Leu Ile Leu Gln Ala Glu Thr Thr
    2690                2695                2700

Ala Gly Thr Val Thr Pro Thr Ala Ile Gly Asp Ser Ile Leu Asn
    2705                2710                2715

Ile Thr Gly Asp Leu Ile His Leu Ala Ser Ser Asp Val Arg Ala
    2720                2725                2730

Pro Gln Pro Ser Glu Leu Gly Ala Glu Ser Pro Ser Arg Met Val
    2735                2740                2745

Ala Ser Gln Ala Tyr Asn Leu Thr Ser Ala Leu Met Arg Ile Leu
    2750                2755                2760

Met Arg Ser Arg Val Leu Asn Glu Glu Pro Leu Thr Leu Ala Gly
    2765                2770                2775

Glu Glu Ile Val Ala Gln Gly Lys Arg Ser Asp Pro Arg Ser Leu
    2780                2785                2790

Leu Cys Tyr Gly Gly Ala Pro Gly Pro Gly Cys His Phe Ser Ile
    2795                2800                2805

Pro Glu Ala Phe Ser Gly Ala Leu Ala Asn Leu Ser Asp Val Val
    2810                2815                2820

Gln Leu Ile Phe Leu Val Asp Ser Asn Pro Phe Pro Phe Gly Tyr
    2825                2830                2835

Ile Ser Asn Tyr Thr Val Ser Thr Lys Val Ala Ser Met Ala Phe
    2840                2845                2850

Gln Thr Gln Ala Gly Ala Gln Ile Pro Ile Glu Arg Leu Ala Ser
    2855                2860                2865

Glu Arg Ala Ile Thr Val Lys Val Pro Asn Asn Ser Asp Trp Ala
    2870                2875                2880

Ala Arg Gly His Arg Ser Ser Ala Asn Ser Ala Asn Ser Val Val
    2885                2890                2895

Val Gln Pro Gln Ala Ser Val Gly Ala Val Val Thr Leu Asp Ser
    2900                2905                2910

Ser Asn Pro Ala Ala Gly Leu His Leu Gln Leu Asn Tyr Thr Leu
    2915                2920                2925

Leu Asp Gly His Tyr Leu Ser Glu Glu Pro Glu Pro Tyr Leu Ala
    2930                2935                2940

Val Tyr Leu His Ser Glu Pro Arg Pro Asn Glu His Asn Cys Ser
    2945                2950                2955

Ala Ser Arg Arg Ile Arg Pro Glu Ser Leu Gln Gly Ala Asp His
```

```
                2960                2965                2970

Arg Pro Tyr Thr Phe Phe Ile Ser Pro Gly Ser Arg Asp Pro Ala
    2975                2980                2985

Gly Ser Tyr His Leu Asn Leu Ser Ser His Phe Arg Trp Ser Ala
    2990                2995                3000

Leu Gln Val Ser Val Gly Leu Tyr Thr Ser Leu Cys Gln Tyr Phe
    3005                3010                3015

Ser Glu Glu Asp Met Val Trp Arg Thr Glu Gly Leu Leu Pro Leu
    3020                3025                3030

Glu Glu Thr Ser Pro Arg Gln Ala Val Cys Leu Thr Arg His Leu
    3035                3040                3045

Thr Ala Phe Gly Ala Ser Leu Phe Val Pro Pro Ser His Val Arg
    3050                3055                3060

Phe Val Phe Pro Glu Pro Thr Ala Asp Val Asn Tyr Ile Val Met
    3065                3070                3075

Leu Thr Cys Ala Val Cys Leu Val Thr Tyr Met Val Met Ala Ala
    3080                3085                3090

Ile Leu His Lys Leu Asp Gln Leu Asp Ala Ser Arg Gly Arg Ala
    3095                3100                3105

Ile Pro Phe Cys Gly Gln Arg Gly Arg Phe Lys Tyr Glu Ile Leu
    3110                3115                3120

Val Lys Thr Gly Trp Gly Arg Gly Ser Gly Thr Thr Ala His Val
    3125                3130                3135

Gly Ile Met Leu Tyr Gly Val Asp Ser Arg Ser Gly His Arg His
    3140                3145                3150

Leu Asp Gly Asp Arg Ala Phe His Arg Asn Ser Leu Asp Ile Phe
    3155                3160                3165

Arg Ile Ala Thr Pro His Ser Leu Gly Ser Val Trp Lys Ile Arg
    3170                3175                3180

Val Trp His Asp Asn Lys Gly Leu Ser Pro Ala Trp Phe Leu Gln
    3185                3190                3195

His Val Ile Val Arg Asp Leu Gln Thr Ala Arg Ser Ala Phe Phe
    3200                3205                3210

Leu Val Asn Asp Trp Leu Ser Val Glu Thr Glu Ala Asn Gly Gly
    3215                3220                3225

Leu Val Glu Lys Glu Val Leu Ala Ala Ser Asp Ala Ala Leu Leu
    3230                3235                3240

Arg Phe Arg Arg Leu Leu Val Ala Glu Leu Gln Arg Gly Phe Phe
    3245                3250                3255

Asp Lys His Ile Trp Leu Ser Ile Trp Asp Arg Pro Pro Arg Ser
    3260                3265                3270

Arg Phe Thr Arg Ile Gln Arg Ala Thr Cys Cys Val Leu Leu Ile
    3275                3280                3285

Cys Leu Phe Leu Gly Ala Asn Ala Val Trp Tyr Gly Ala Val Gly
    3290                3295                3300

Asp Ser Ala Tyr Ser Thr Gly His Val Ser Arg Leu Ser Pro Leu
    3305                3310                3315

Ser Val Asp Thr Val Ala Val Gly Leu Val Ser Ser Val Val Val
    3320                3325                3330

Tyr Pro Val Tyr Leu Ala Ile Leu Phe Leu Phe Arg Met Ser Arg
    3335                3340                3345

Ser Lys Val Ala Gly Ser Pro Ser Pro Thr Pro Ala Gly Gln Gln
    3350                3355                3360
```

-continued

Val Leu Asp Ile Asp Ser Cys Leu Asp Ser Ser Val Leu Asp Ser
3365                3370                3375

Ser Phe Leu Thr Phe Ser Gly Leu His Ala Glu Gln Ala Phe Val
3380                3385                3390

Gly Gln Met Lys Ser Asp Leu Phe Leu Asp Asp Ser Lys Ser Leu
3395                3400                3405

Val Cys Trp Pro Ser Gly Glu Gly Thr Leu Ser Trp Pro Asp Leu
3410                3415                3420

Leu Ser Asp Pro Ser Ile Val Gly Ser Asn Leu Arg Gln Leu Ala
3425                3430                3435

Arg Gly Gln Ala Gly His Gly Leu Gly Pro Glu Glu Asp Gly Phe
3440                3445                3450

Ser Leu Ala Ser Pro Tyr Ser Pro Ala Lys Ser Phe Ser Ala Ser
3455                3460                3465

Asp Glu Asp Leu Ile Gln Gln Val Leu Ala Glu Gly Val Ser Ser
3470                3475                3480

Pro Ala Pro Thr Gln Asp Thr His Met Glu Thr Asp Leu Leu Ser
3485                3490                3495

Ser Leu Ser Ser Thr Pro Gly Glu Lys Thr Glu Thr Leu Ala Leu
3500                3505                3510

Gln Arg Leu Gly Glu Leu Gly Pro Pro Ser Pro Gly Leu Asn Trp
3515                3520                3525

Glu Gln Pro Gln Ala Ala Arg Leu Ser Arg Thr Gly Leu Val Glu
3530                3535                3540

Gly Leu Arg Lys Arg Leu Leu Pro Ala Trp Cys Ala Ser Leu Ala
3545                3550                3555

His Gly Leu Ser Leu Leu Leu Val Ala Val Ala Val Ala Val Ser
3560                3565                3570

Gly Trp Val Gly Ala Ser Phe Pro Pro Gly Val Ser Val Ala Trp
3575                3580                3585

Leu Leu Ser Ser Ser Ala Ser Phe Leu Ala Ser Phe Leu Gly Trp
3590                3595                3600

Glu Pro Leu Lys Val Leu Leu Glu Ala Leu Tyr Phe Ser Leu Val
3605                3610                3615

Ala Lys Arg Leu His Pro Asp Glu Asp Asp Thr Leu Val Glu Ser
3620                3625                3630

Pro Ala Val Thr Pro Val Ser Ala Arg Val Pro Arg Val Arg Pro
3635                3640                3645

Pro His Gly Phe Ala Leu Phe Leu Ala Lys Glu Glu Ala Arg Lys
3650                3655                3660

Val Lys Arg Leu His Gly Met Leu Arg Ser Leu Leu Val Tyr Met
3665                3670                3675

Leu Phe Leu Leu Val Thr Leu Leu Ala Ser Tyr Gly Asp Ala Ser
3680                3685                3690

Cys His Gly His Ala Tyr Arg Leu Gln Ser Ala Ile Lys Gln Glu
3695                3700                3705

Leu His Ser Arg Ala Phe Leu Ala Ile Thr Arg Ser Glu Glu Leu
3710                3715                3720

Trp Pro Trp Met Ala His Val Leu Leu Pro Tyr Val His Gly Asn
3725                3730                3735

Gln Ser Ser Pro Glu Leu Gly Pro Pro Arg Leu Arg Gln Val Arg
3740                3745                3750

-continued

```
Leu Gln Glu Ala Leu Tyr Pro Asp Pro Gly Pro Arg Val His
    3755                3760            3765

Thr Cys Ser Ala Ala Gly Gly Phe Ser Thr Ser Asp Tyr Asp Val
    3770                3775            3780

Gly Trp Glu Ser Pro His Asn Gly Ser Gly Thr Trp Ala Tyr Ser
    3785                3790            3795

Ala Pro Asp Leu Leu Gly Ala Trp Ser Trp Gly Ser Cys Ala Val
    3800                3805            3810

Tyr Asp Ser Gly Gly Tyr Val Gln Glu Leu Gly Leu Ser Leu Glu
    3815                3820            3825

Glu Ser Arg Asp Arg Leu Arg Phe Leu Gln Leu His Asn Trp Leu
    3830                3835            3840

Asp Asn Arg Ser Arg Ala Val Phe Leu Glu Leu Thr Arg Tyr Ser
    3845                3850            3855

Pro Ala Val Gly Leu His Ala Ala Val Thr Leu Arg Leu Glu Phe
    3860                3865            3870

Pro Ala Ala Gly Arg Ala Leu Ala Ala Leu Ser Val Arg Pro Phe
    3875                3880            3885

Ala Leu Arg Arg Leu Ser Ala Gly Leu Ser Leu Pro Leu Leu Thr
    3890                3895            3900

Ser Val Cys Leu Leu Leu Phe Ala Val His Phe Ala Val Ala Glu
    3905                3910            3915

Ala Arg Thr Trp His Arg Glu Gly Arg Trp Arg Val Leu Arg Leu
    3920                3925            3930

Gly Ala Trp Ala Arg Trp Leu Leu Val Ala Leu Thr Ala Ala Thr
    3935                3940            3945

Ala Leu Val Arg Leu Ala Gln Leu Gly Ala Ala Asp Arg Gln Trp
    3950                3955            3960

Thr Arg Phe Val Arg Gly Arg Pro Arg Arg Phe Thr Ser Phe Asp
    3965                3970            3975

Gln Val Ala His Val Ser Ser Ala Ala Arg Gly Leu Ala Ala Ser
    3980                3985            3990

Leu Leu Phe Leu Leu Leu Val Lys Ala Ala Gln His Val Arg Phe
    3995                4000            4005

Val Arg Gln Trp Ser Val Phe Gly Lys Thr Leu Cys Arg Ala Leu
    4010                4015            4020

Pro Glu Leu Leu Gly Val Thr Leu Gly Leu Val Val Leu Gly Val
    4025                4030            4035

Ala Tyr Ala Gln Leu Ala Ile Leu Leu Val Ser Ser Cys Val Asp
    4040                4045            4050

Ser Leu Trp Ser Val Ala Gln Ala Leu Leu Val Leu Cys Pro Gly
    4055                4060            4065

Thr Gly Leu Ser Thr Leu Cys Pro Ala Glu Ser Trp His Leu Ser
    4070                4075            4080

Pro Leu Leu Cys Val Gly Leu Trp Ala Leu Arg Leu Trp Gly Ala
    4085                4090            4095

Leu Arg Leu Gly Ala Val Ile Leu Arg Trp Arg Tyr His Ala Leu
    4100                4105            4110

Arg Gly Glu Leu Tyr Arg Pro Ala Trp Glu Pro Gln Asp Tyr Glu
    4115                4120            4125

Met Val Glu Leu Phe Leu Arg Arg Leu Arg Leu Trp Met Gly Leu
    4130                4135            4140

Ser Lys Val Lys Glu Phe Arg His Lys Val Arg Phe Glu Gly Met
```

```
                  4145                 4150                 4155

Glu Pro Leu Pro Ser Arg  Ser Arg Gly Ser Lys  Val Ser Pro
    4160                 4165                 4170

Asp Val Pro Pro Pro Ser  Ala Gly Ser Asp Ala  Ser His Pro Ser
    4175                 4180                 4185

Thr Ser Ser Ser Gln Leu  Asp Gly Leu Ser Val  Ser Leu Gly Arg
    4190                 4195                 4200

Leu Gly Thr Arg Cys Glu  Pro Glu Pro Ser Arg  Leu Gln Ala Val
    4205                 4210                 4215

Phe Glu Ala Leu Leu Thr  Gln Phe Asp Arg Leu  Asn Gln Ala Thr
    4220                 4225                 4230

Glu Asp Val Tyr Gln Leu  Glu Gln Gln Leu His  Ser Leu Gln Gly
    4235                 4240                 4245

Arg Arg Ser Ser Arg Ala  Pro Ala Gly Ser Ser  Arg Gly Pro Ser
    4250                 4255                 4260

Pro Gly Leu Arg Pro Ala  Leu Pro Ser Arg Leu  Ala Arg Ala Ser
    4265                 4270                 4275

Arg Gly Val Asp Leu Ala  Thr Gly Pro Ser Arg  Thr Pro Leu Arg
    4280                 4285                 4290

Ala Lys Asn Lys Val His  Pro Ser Ser Thr
    4295                 4300

<210> SEQ ID NO 3
<211> LENGTH: 29
<212> TYPE: DNA
<213> ORGANISM: Artificial sequence
<220> FEATURE:
<223> OTHER INFORMATION: PCR primer BPF14

<400> SEQUENCE: 3
ccatccacct gctgtgtgac ctggtaaat                                    29

<210> SEQ ID NO 4
<211> LENGTH: 26
<212> TYPE: DNA
<213> ORGANISM: Artificial sequence
<220> FEATURE:
<223> OTHER INFORMATION: PCR primer BPR9

<400> SEQUENCE: 4
ccacctcatc gccccttcct aagcat                                       26

<210> SEQ ID NO 5
<211> LENGTH: 31
<212> TYPE: DNA
<213> ORGANISM: Artificial sequence
<220> FEATURE:
<223> OTHER INFORMATION: PCR primer BPF9

<400> SEQUENCE: 5
attttttgag atggagcttc actcttgcag g                                 31

<210> SEQ ID NO 6
<211> LENGTH: 20
<212> TYPE: DNA
<213> ORGANISM: Artificial sequence
<220> FEATURE:
<223> OTHER INFORMATION: PCR primer BPR4

<400> SEQUENCE: 6
cgctcggcag gccccctaacc                                             20
```

<210> SEQ ID NO 7
<211> LENGTH: 21
<212> TYPE: DNA
<213> ORGANISM: Artificial sequence
<220> FEATURE:
<223> OTHER INFORMATION: PCR primer BPF12

<400> SEQUENCE: 7
ccgcccccag gagcctagac g                                          21

<210> SEQ ID NO 8
<211> LENGTH: 27
<212> TYPE: DNA
<213> ORGANISM: Artificial sequence
<220> FEATURE:
<223> OTHER INFORMATION: PCR primer BPR5

<400> SEQUENCE: 8
catcctgttc atccgctcca cggttac                                    27

<210> SEQ ID NO 9
<211> LENGTH: 20
<212> TYPE: DNA
<213> ORGANISM: Artificial sequence
<220> FEATURE:
<223> OTHER INFORMATION: PCR primer F13

<400> SEQUENCE: 9
tggagggagg gacgccaatc                                            20

<210> SEQ ID NO 10
<211> LENGTH: 20
<212> TYPE: DNA
<213> ORGANISM: Artificial sequence
<220> FEATURE:
<223> OTHER INFORMATION: PCR primer R27

<400> SEQUENCE: 10
gtcaacgtgg gcctccaagt                                            20

<210> SEQ ID NO 11
<211> LENGTH: 21
<212> TYPE: DNA
<213> ORGANISM: Artificial sequence
<220> FEATURE:
<223> OTHER INFORMATION: PCR primer F26

<400> SEQUENCE: 11
agcgcaacta cttggaggcc c                                          21

<210> SEQ ID NO 12
<211> LENGTH: 28
<212> TYPE: DNA
<213> ORGANISM: Artificial sequence
<220> FEATURE:
<223> OTHER INFORMATION: PCR primer R2

<400> SEQUENCE: 12
gcagggtgag caggtggggc catcctac                                   28

<210> SEQ ID NO 13
<211> LENGTH: 26
<212> TYPE: DNA
<213> ORGANISM: Artificial sequence
<220> FEATURE:

```
<223> OTHER INFORMATION: PCR primer BPF15

<400> SEQUENCE: 13
gaggctgtgg gggtccagtc aagtgg                                          26

<210> SEQ ID NO 14
<211> LENGTH: 25
<212> TYPE: DNA
<213> ORGANISM: Artificial sequence
<220> FEATURE:
<223> OTHER INFORMATION: PCR primer BPR12

<400> SEQUENCE: 14
agggaggcag aggaaagggc cgaac                                           25

<210> SEQ ID NO 15
<211> LENGTH: 24
<212> TYPE: DNA
<213> ORGANISM: Artificial sequence
<220> FEATURE:
<223> OTHER INFORMATION: PCR primer BPF6

<400> SEQUENCE: 15
ccccgtcctc cccgtccttt tgtc                                            24

<210> SEQ ID NO 16
<211> LENGTH: 21
<212> TYPE: DNA
<213> ORGANISM: Artificial sequence
<220> FEATURE:
<223> OTHER INFORMATION: PCR primer BPR6

<400> SEQUENCE: 16
aagcgcaaaa gggctgcgtc g                                               21

<210> SEQ ID NO 17
<211> LENGTH: 22
<212> TYPE: DNA
<213> ORGANISM: Artificial sequence
<220> FEATURE:
<223> OTHER INFORMATION: PCR primer BPF13

<400> SEQUENCE: 17
ggccctccct gccttctagg cg                                              22

<210> SEQ ID NO 18
<211> LENGTH: 21
<212> TYPE: DNA
<213> ORGANISM: Artificial sequence
<220> FEATURE:
<223> OTHER INFORMATION: PCR primer KG8R25

<400> SEQUENCE: 18
gttgcagcca agcccatgtt a                                               21

<210> SEQ ID NO 19
<211> LENGTH: 19
<212> TYPE: DNA
<213> ORGANISM: Artificial sequence
<220> FEATURE:
<223> OTHER INFORMATION: PCR primer 1F1

<400> SEQUENCE: 19
ggtcgcgctg tggcgaagg                                                  19
```

```
<210> SEQ ID NO 20
<211> LENGTH: 16
<212> TYPE: DNA
<213> ORGANISM: Artificial sequence
<220> FEATURE:
<223> OTHER INFORMATION: PCR primer 1R1

<400> SEQUENCE: 20
cggcgggcgg catcgt                                                        16

<210> SEQ ID NO 21
<211> LENGTH: 16
<212> TYPE: DNA
<213> ORGANISM: Artificial sequence
<220> FEATURE:
<223> OTHER INFORMATION: PCR primer 1F2

<400> SEQUENCE: 21
acggcggggc catgcg                                                        16

<210> SEQ ID NO 22
<211> LENGTH: 18
<212> TYPE: DNA
<213> ORGANISM: Artificial sequence
<220> FEATURE:
<223> OTHER INFORMATION: PCR primer 1R2

<400> SEQUENCE: 22
gcgtcctggc ccgcgtcc                                                      18

<210> SEQ ID NO 23
<211> LENGTH: 20
<212> TYPE: DNA
<213> ORGANISM: Artificial sequence
<220> FEATURE:
<223> OTHER INFORMATION: PCR primer 2F

<400> SEQUENCE: 23
ttggggatgc tggcaatgtg                                                    20

<210> SEQ ID NO 24
<211> LENGTH: 20
<212> TYPE: DNA
<213> ORGANISM: Artificial sequence
<220> FEATURE:
<223> OTHER INFORMATION: PCR primer 2R

<400> SEQUENCE: 24
gggattcggc aaagctgatg                                                    20

<210> SEQ ID NO 25
<211> LENGTH: 20
<212> TYPE: DNA
<213> ORGANISM: Artificial sequence
<220> FEATURE:
<223> OTHER INFORMATION: PCR primer 3F

<400> SEQUENCE: 25
ccatcagctt tgccgaatcc                                                    20

<210> SEQ ID NO 26
<211> LENGTH: 20
<212> TYPE: DNA
<213> ORGANISM: Artificial sequence
<220> FEATURE:
<223> OTHER INFORMATION: PCR primer 3R
```

```
<400> SEQUENCE: 26
agggcagaag ggatattggg                                           20

<210> SEQ ID NO 27
<211> LENGTH: 20
<212> TYPE: DNA
<213> ORGANISM: Artificial sequence
<220> FEATURE:
<223> OTHER INFORMATION: PCR primer 4F

<400> SEQUENCE: 27
agacccttcc caccagacct                                           20

<210> SEQ ID NO 28
<211> LENGTH: 19
<212> TYPE: DNA
<213> ORGANISM: Artificial sequence
<220> FEATURE:
<223> OTHER INFORMATION: PCR primer 4R

<400> SEQUENCE: 28
tgagccctgc ccagtgtct                                            19

<210> SEQ ID NO 29
<211> LENGTH: 21
<212> TYPE: DNA
<213> ORGANISM: Artificial sequence
<220> FEATURE:
<223> OTHER INFORMATION: PCR primer 5F1

<400> SEQUENCE: 29
gagccaggag gagcagaacc c                                         21

<210> SEQ ID NO 30
<211> LENGTH: 21
<212> TYPE: DNA
<213> ORGANISM: Artificial sequence
<220> FEATURE:
<223> OTHER INFORMATION: PCR primer 5R1

<400> SEQUENCE: 30
agagggacag gcaggcaaag g                                         21

<210> SEQ ID NO 31
<211> LENGTH: 18
<212> TYPE: DNA
<213> ORGANISM: Artificial sequence
<220> FEATURE:
<223> OTHER INFORMATION: PCR primer 5F2

<400> SEQUENCE: 31
cccagccctc cagtgcct                                             18

<210> SEQ ID NO 32
<211> LENGTH: 20
<212> TYPE: DNA
<213> ORGANISM: Artificial sequence
<220> FEATURE:
<223> OTHER INFORMATION: PCR primer 5R2

<400> SEQUENCE: 32
cccaggcagc acatagcgat                                           20

<210> SEQ ID NO 33
<211> LENGTH: 18
```

```
<212> TYPE: DNA
<213> ORGANISM: Artificial sequence
<220> FEATURE:
<223> OTHER INFORMATION: PCR primer 5F3

<400> SEQUENCE: 33
ccgaggtgga tgccgctg                                               18

<210> SEQ ID NO 34
<211> LENGTH: 21
<212> TYPE: DNA
<213> ORGANISM: Artificial sequence
<220> FEATURE:
<223> OTHER INFORMATION: PCR primer 5R3

<400> SEQUENCE: 34
gaaggggagt gggcagcaga c                                           21

<210> SEQ ID NO 35
<211> LENGTH: 21
<212> TYPE: DNA
<213> ORGANISM: Artificial sequence
<220> FEATURE:
<223> OTHER INFORMATION: PCR primer 6F

<400> SEQUENCE: 35
cactgaccgt tgacaccctc g                                           21

<210> SEQ ID NO 36
<211> LENGTH: 21
<212> TYPE: DNA
<213> ORGANISM: Artificial sequence
<220> FEATURE:
<223> OTHER INFORMATION: PCR primer 6R

<400> SEQUENCE: 36
tgccccagtg cttcagagat c                                           21

<210> SEQ ID NO 37
<211> LENGTH: 19
<212> TYPE: DNA
<213> ORGANISM: Artificial sequence
<220> FEATURE:
<223> OTHER INFORMATION: PCR primer 7F

<400> SEQUENCE: 37
ggagtgccct gagccccct                                              19

<210> SEQ ID NO 38
<211> LENGTH: 19
<212> TYPE: DNA
<213> ORGANISM: Artificial sequence
<220> FEATURE:
<223> OTHER INFORMATION: PCR primer 7R

<400> SEQUENCE: 38
cccctaacca cagccagcg                                              19

<210> SEQ ID NO 39
<211> LENGTH: 21
<212> TYPE: DNA
<213> ORGANISM: Artificial sequence
<220> FEATURE:
<223> OTHER INFORMATION: PCR primer 8F

<400> SEQUENCE: 39
```

-continued

| | |
|---|---|
| tctgttcgtc ctggtgtcct g | 21 |

<210> SEQ ID NO 40
<211> LENGTH: 21
<212> TYPE: DNA
<213> ORGANISM: Artificial sequence
<220> FEATURE:
<223> OTHER INFORMATION: PCR primer 8R

<400> SEQUENCE: 40

| | |
|---|---|
| gcaggagggc aggttgtaga a | 21 |

<210> SEQ ID NO 41
<211> LENGTH: 20
<212> TYPE: DNA
<213> ORGANISM: Artificial sequence
<220> FEATURE:
<223> OTHER INFORMATION: PCR primer 9F

<400> SEQUENCE: 41

| | |
|---|---|
| ggtaggggga gtctgggctt | 20 |

<210> SEQ ID NO 42
<211> LENGTH: 17
<212> TYPE: DNA
<213> ORGANISM: Artificial sequence
<220> FEATURE:
<223> OTHER INFORMATION: PCR primer 9R

<400> SEQUENCE: 42

| | |
|---|---|
| gaggccaccc cgagtcc | 17 |

<210> SEQ ID NO 43
<211> LENGTH: 20
<212> TYPE: DNA
<213> ORGANISM: Artificial sequence
<220> FEATURE:
<223> OTHER INFORMATION: PCR primer 10F

<400> SEQUENCE: 43

| | |
|---|---|
| gttgggcatc tctgacggtg | 20 |

<210> SEQ ID NO 44
<211> LENGTH: 20
<212> TYPE: DNA
<213> ORGANISM: Artificial sequence
<220> FEATURE:
<223> OTHER INFORMATION: PCR primer 10R

<400> SEQUENCE: 44

| | |
|---|---|
| ggaaggtggc ctgaggagat | 20 |

<210> SEQ ID NO 45
<211> LENGTH: 17
<212> TYPE: DNA
<213> ORGANISM: Artificial sequence
<220> FEATURE:
<223> OTHER INFORMATION: PCR primer 11F2

<400> SEQUENCE: 45

| | |
|---|---|
| ggggtccacg ggccatg | 17 |

<210> SEQ ID NO 46
<211> LENGTH: 20
<212> TYPE: DNA
<213> ORGANISM: Artificial sequence

```
<220> FEATURE:
<223> OTHER INFORMATION: PCR primer 11R2

<400> SEQUENCE: 46
aagcccagca gcacggtgag                                               20

<210> SEQ ID NO 47
<211> LENGTH: 17
<212> TYPE: DNA
<213> ORGANISM: Artificial sequence
<220> FEATURE:
<223> OTHER INFORMATION: PCR primer 11midF

<400> SEQUENCE: 47
gcttgcagcc acggaac                                                  17

<210> SEQ ID NO 48
<211> LENGTH: 20
<212> TYPE: DNA
<213> ORGANISM: Artificial sequence
<220> FEATURE:
<223> OTHER INFORMATION: PCR primer 11midR

<400> SEQUENCE: 48
gcagtgctac cactgagaac                                               20

<210> SEQ ID NO 49
<211> LENGTH: 23
<212> TYPE: DNA
<213> ORGANISM: Artificial sequence
<220> FEATURE:
<223> OTHER INFORMATION: PCR primer 11F1

<400> SEQUENCE: 49
tgcccctggg agaccaacga tac                                           23

<210> SEQ ID NO 50
<211> LENGTH: 22
<212> TYPE: DNA
<213> ORGANISM: Artificial sequence
<220> FEATURE:
<223> OTHER INFORMATION: PCR primer 11R1

<400> SEQUENCE: 50
ggctgctgcc ctcactggga ag                                            22

<210> SEQ ID NO 51
<211> LENGTH: 18
<212> TYPE: DNA
<213> ORGANISM: Artificial sequence
<220> FEATURE:
<223> OTHER INFORMATION: PCR primer 12F

<400> SEQUENCE: 51
gaggcgacag gctaaggg                                                 18

<210> SEQ ID NO 52
<211> LENGTH: 25
<212> TYPE: DNA
<213> ORGANISM: Artificial sequence
<220> FEATURE:
<223> OTHER INFORMATION: Primer for PCR

<400> SEQUENCE: 52
aggtcaacgt gggcctccaa gtagt                                         25
```

```
<210> SEQ ID NO 53
<211> LENGTH: 19
<212> TYPE: DNA
<213> ORGANISM: Artificial sequence
<220> FEATURE:
<223> OTHER INFORMATION: Forward nested primer F32

<400> SEQUENCE: 53
gccttgcgca gcttggact                                               19

<210> SEQ ID NO 54
<211> LENGTH: 20
<212> TYPE: DNA
<213> ORGANISM: Artificial sequence
<220> FEATURE:
<223> OTHER INFORMATION: Second specific primer 31R

<400> SEQUENCE: 54
acagtgtctt gagtccaagc                                              20

<210> SEQ ID NO 55
<211> LENGTH: 30
<212> TYPE: DNA
<213> ORGANISM: Artificial sequence
<220> FEATURE:
<223> OTHER INFORMATION: PCR primer

<400> SEQUENCE: 55
ctggtgacct acatggtcat ggccgagatc                                   30

<210> SEQ ID NO 56
<211> LENGTH: 30
<212> TYPE: DNA
<213> ORGANISM: Artificial sequence
<220> FEATURE:
<223> OTHER INFORMATION: PCR primer

<400> SEQUENCE: 56
ggttgtctat cccgtctacc tggccctcct                                   30

<210> SEQ ID NO 57
<211> LENGTH: 25
<212> TYPE: DNA
<213> ORGANISM: Artificial sequence
<220> FEATURE:
<223> OTHER INFORMATION: PCR primer

<400> SEQUENCE: 57
gtccccagcc ccagcccacc tggcc                                        25

<210> SEQ ID NO 58
<211> LENGTH: 7
<212> TYPE: PRT
<213> ORGANISM: Homo sapiens

<400> SEQUENCE: 58

Trp Asp Phe Gly Asp Gly Ser
1               5

<210> SEQ ID NO 59
<211> LENGTH: 4
<212> TYPE: PRT
<213> ORGANISM: Homo sapiens

<400> SEQUENCE: 59
```

His Leu Thr Ala
1

<210> SEQ ID NO 60
<211> LENGTH: 27
<212> TYPE: DNA
<213> ORGANISM: Artificial sequence
<220> FEATURE:
<223> OTHER INFORMATION: PCR primer

SEQUENCE: 60 gcagggtgag caggtggggc catccta    27

<210> SEQ ID NO 61
<211> LENGTH: 19
<212> TYPE: DNA
<213> ORGANISM: Artificial sequence
<220> FEATURE:
<223> OTHER INFORMATION: PCR primer 12R-2

<400> SEQUENCE: 61
catgaagcag agcagaagg    19

<210> SEQ ID NO 62
<211> LENGTH: 20
<212> TYPE: DNA
<213> ORGANISM: Artificial sequence
<220> FEATURE:
<223> OTHER INFORMATION: PCR primer 13F

<400> SEQUENCE: 62
tggagggagg gacgccaatc    20

<210> SEQ ID NO 63
<211> LENGTH: 19
<212> TYPE: DNA
<213> ORGANISM: Artificial sequence
<220> FEATURE:
<223> OTHER INFORMATION: PCR primer 13R

<400> SEQUENCE: 63
gaggctgggg ctgggacaa    19

<210> SEQ ID NO 64
<211> LENGTH: 18
<212> TYPE: DNA
<213> ORGANISM: Artificial sequence
<220> FEATURE:
<223> OTHER INFORMATION: PCR primer 14F

<400> SEQUENCE: 64
cccggttcac tcactgcg    18

<210> SEQ ID NO 65
<211> LENGTH: 20
<212> TYPE: DNA
<213> ORGANISM: Artificial sequence
<220> FEATURE:
<223> OTHER INFORMATION: PCR primer 14R

SEQUENCE: 65 ccgtgctcag agcctgaaag    20

<210> SEQ ID NO 66
<211> LENGTH: 18
<212> TYPE: DNA

```
<213> ORGANISM: Artificial sequence
<220> FEATURE:
<223> OTHER INFORMATION: PCR primer 15F16

<400> SEQUENCE: 66
cgggtgggga gcaggtgg                                                 18

<210> SEQ ID NO 67
<211> LENGTH: 21
<212> TYPE: DNA
<213> ORGANISM: Artificial sequence
<220> FEATURE:
<223> OTHER INFORMATION: PCR primer 15R16

<400> SEQUENCE: 67
gctctgggtc aggacagggg a                                             21

<210> SEQ ID NO 68
<211> LENGTH: 18
<212> TYPE: DNA
<213> ORGANISM: Artificial sequence
<220> FEATURE:
<223> OTHER INFORMATION: PCR primer 15F15

<400> SEQUENCE: 68
cgcctggggg tgttctttt                                                18

<210> SEQ ID NO 69
<211> LENGTH: 18
<212> TYPE: DNA
<213> ORGANISM: Artificial sequence
<220> FEATURE:
<223> OTHER INFORMATION: PCR primer 15R15

<400> SEQUENCE: 69
acgtgatgtt gtcgcccg                                                 18

<210> SEQ ID NO 70
<211> LENGTH: 18
<212> TYPE: DNA
<213> ORGANISM: Artificial sequence
<220> FEATURE:
<223> OTHER INFORMATION: PCR primer 15F14

<400> SEQUENCE: 70
gcccccgtgg tggtcagc                                                 18

<210> SEQ ID NO 71
<211> LENGTH: 18
<212> TYPE: DNA
<213> ORGANISM: Artificial sequence
<220> FEATURE:
<223> OTHER INFORMATION: PCR primer 15R14

<400> SEQUENCE: 71
caggctgcgt ggggatgc                                                 18

<210> SEQ ID NO 72
<211> LENGTH: 18
<212> TYPE: DNA
<213> ORGANISM: Artificial sequence
<220> FEATURE:
<223> OTHER INFORMATION: PCR primer 15F13

<400> SEQUENCE: 72
ctggaggtgc tgcgcgtt                                                 18
```

<210> SEQ ID NO 73
<211> LENGTH: 18
<212> TYPE: DNA
<213> ORGANISM: Artificial sequence
<220> FEATURE:
<223> OTHER INFORMATION: PCR primer 15R13

<400> SEQUENCE: 73
ctggctccac gcagatgc                                                 18

<210> SEQ ID NO 74
<211> LENGTH: 18
<212> TYPE: DNA
<213> ORGANISM: Artificial sequence
<220> FEATURE:
<223> OTHER INFORMATION: PCR primer 15F12

<400> SEQUENCE: 74
cgtgaacagg gcgcatta                                                 18

<210> SEQ ID NO 75
<211> LENGTH: 21
<212> TYPE: DNA
<213> ORGANISM: Artificial sequence
<220> FEATURE:
<223> OTHER INFORMATION: PCR primer 15R12

<400> SEQUENCE: 75
gcagcagaga tgttgttgga c                                             21

<210> SEQ ID NO 76
<211> LENGTH: 21
<212> TYPE: DNA
<213> ORGANISM: Artificial sequence
<220> FEATURE:
<223> OTHER INFORMATION: PCR primer 15F11

<400> SEQUENCE: 76
ccaggctcct atcttgtgac a                                             21

<210> SEQ ID NO 77
<211> LENGTH: 21
<212> TYPE: DNA
<213> ORGANISM: Artificial sequence
<220> FEATURE:
<223> OTHER INFORMATION: PCR primer 15R11

<400> SEQUENCE: 77
tgaagtcacc tgtgctgttg t                                             21

<210> SEQ ID NO 78
<211> LENGTH: 19
<212> TYPE: DNA
<213> ORGANISM: Artificial sequence
<220> FEATURE:
<223> OTHER INFORMATION: PCR primer 15F10

<400> SEQUENCE: 78
ctacctgtgg gatctgggg                                                19

<210> SEQ ID NO 79
<211> LENGTH: 18
<212> TYPE: DNA
<213> ORGANISM: Artificial sequence
<220> FEATURE:

```
<223> OTHER INFORMATION: PCR primer 15R10

<400> SEQUENCE: 79
tgctgaagct cacgctcc                                                  18

<210> SEQ ID NO 80
<211> LENGTH: 20
<212> TYPE: DNA
<213> ORGANISM: Artificial sequence
<220> FEATURE:
<223> OTHER INFORMATION: PCR primer 15F9

<400> SEQUENCE: 80
gggctcgtcg tcaatgcaag                                                20

<210> SEQ ID NO 81
<211> LENGTH: 20
<212> TYPE: DNA
<213> ORGANISM: Artificial sequence
<220> FEATURE:
<223> OTHER INFORMATION: PCR primer 15R9

<400> SEQUENCE: 81
caccacctgc agcccctcta                                                20

<210> SEQ ID NO 82
<211> LENGTH: 20
<212> TYPE: DNA
<213> ORGANISM: Artificial sequence
<220> FEATURE:
<223> OTHER INFORMATION: PCR primer 15F8

<400> SEQUENCE: 82
ccgcccagga cagcatcttc                                                20

<210> SEQ ID NO 83
<211> LENGTH: 18
<212> TYPE: DNA
<213> ORGANISM: Artificial sequence
<220> FEATURE:
<223> OTHER INFORMATION: PCR primer 15R8

<400> SEQUENCE: 83
cgctgcccag catgttgg                                                  18

<210> SEQ ID NO 84
<211> LENGTH: 19
<212> TYPE: DNA
<213> ORGANISM: Artificial sequence
<220> FEATURE:
<223> OTHER INFORMATION: PCR primer 15F7

<400> SEQUENCE: 84
cggcaaaggc ttctcgctc                                                 19

<210> SEQ ID NO 85
<211> LENGTH: 20
<212> TYPE: DNA
<213> ORGANISM: Artificial sequence
<220> FEATURE:
<223> OTHER INFORMATION: PCR primer 15R7

<400> SEQUENCE: 85
ccgggtgtgg ggaagctatg                                                20
```

<210> SEQ ID NO 86
<211> LENGTH: 21
<212> TYPE: DNA
<213> ORGANISM: Artificial sequence
<220> FEATURE:
<223> OTHER INFORMATION: PCR primer 15F6

<400> SEQUENCE: 86
cgagccattt accacccata g         21

<210> SEQ ID NO 87
<211> LENGTH: 19
<212> TYPE: DNA
<213> ORGANISM: Artificial sequence
<220> FEATURE:
<223> OTHER INFORMATION: PCR primer 15R6

<400> SEQUENCE: 87
gcccagcacc agctcacat         19

<210> SEQ ID NO 88
<211> LENGTH: 19
<212> TYPE: DNA
<213> ORGANISM: Artificial sequence
<220> FEATURE:
<223> OTHER INFORMATION: PCR primer 15F5

<400> SEQUENCE: 88
ccacgggcac caatgtgag         19

<210> SEQ ID NO 89
<211> LENGTH: 20
<212> TYPE: DNA
<213> ORGANISM: Artificial sequence
<220> FEATURE:
<223> OTHER INFORMATION: PCR primer 15R5

<400> SEQUENCE: 89
ggcagccagc aggatctgaa         20

<210> SEQ ID NO 90
<211> LENGTH: 18
<212> TYPE: DNA
<213> ORGANISM: Artificial sequence
<220> FEATURE:
<223> OTHER INFORMATION: PCR pimer 15F4

<400> SEQUENCE: 90
cagcagcaag gtggtggc         18

<210> SEQ ID NO 91
<211> LENGTH: 18
<212> TYPE: DNA
<213> ORGANISM: Artificial sequence
<220> FEATURE:
<223> OTHER INFORMATION: PCR primer 15R4

<400> SEQUENCE: 91
gcgtaggcga cccgagag         18

<210> SEQ ID NO 92
<211> LENGTH: 21
<212> TYPE: DNA
<213> ORGANISM: Artificial sequence
<220> FEATURE:
<223> OTHER INFORMATION: PCR primer 15F3

```
<400> SEQUENCE: 92
acgggcactg agaggaactt c                                              21

<210> SEQ ID NO 93
<211> LENGTH: 20
<212> TYPE: DNA
<213> ORGANISM: Artificial sequence
<220> FEATURE:
<223> OTHER INFORMATION: PCR primer 15R3

<400> SEQUENCE: 93
accagcgtgc ggttctcact                                                20

<210> SEQ ID NO 94
<211> LENGTH: 19
<212> TYPE: DNA
<213> ORGANISM: Artificial sequence
<220> FEATURE:
<223> OTHER INFORMATION: PCR primer 15F2

<400> SEQUENCE: 94
gccgcgacgt cacctacac                                                 19

<210> SEQ ID NO 95
<211> LENGTH: 18
<212> TYPE: DNA
<213> ORGANISM: Artificial sequence
<220> FEATURE:
<223> OTHER INFORMATION: PCR primer 15R2

<400> SEQUENCE: 95
tcggccctgg gctcatct                                                  18

<210> SEQ ID NO 96
<211> LENGTH: 20
<212> TYPE: DNA
<213> ORGANISM: Artificial sequence
<220> FEATURE:
<223> OTHER INFORMATION: PCR primer 15F1

<400> SEQUENCE: 96
gtcgccaggg caggacacag                                                20

<210> SEQ ID NO 97
<211> LENGTH: 21
<212> TYPE: DNA
<213> ORGANISM: Artificial sequence
<220> FEATURE:
<223> OTHER INFORMATION: PCR primer 15F1-1

<400> SEQUENCE: 97
acttggaggc ccacgttgac c                                              21

<210> SEQ ID NO 98
<211> LENGTH: 19
<212> TYPE: DNA
<213> ORGANISM: Artificial sequence
<220> FEATURE:
<223> OTHER INFORMATION: PCR primer 15R1-1

<400> SEQUENCE: 98
tgatgggcac caggcgctc                                                 19

<210> SEQ ID NO 99
<211> LENGTH: 21
```

```
<212> TYPE: DNA
<213> ORGANISM: Artificial sequence
<220> FEATURE:
<223> OTHER INFORMATION: PCR primer 15F1-2

<400> SEQUENCE: 99
catccaggcc aatgtgacgg t                                         21

<210> SEQ ID NO 100
<211> LENGTH: 21
<212> TYPE: DNA
<213> ORGANISM: Artificial sequence
<220> FEATURE:
<223> OTHER INFORMATION: PCR primer 15R1-2

<400> SEQUENCE: 100
cctggtggca agctgggtgt t                                         21

<210> SEQ ID NO 101
<211> LENGTH: 20
<212> TYPE: DNA
<213> ORGANISM: Artificial sequence
<220> FEATURE:
<223> OTHER INFORMATION: PCR primer 16F

<400> SEQUENCE: 101
taaaactgga tggggctctc                                           20

<210> SEQ ID NO 102
<211> LENGTH: 18
<212> TYPE: DNA
<213> ORGANISM: Artificial sequence
<220> FEATURE:
<223> OTHER INFORMATION: PCR primer 16R

<400> SEQUENCE: 102
ggcctccacc agcactaa                                             18

<210> SEQ ID NO 103
<211> LENGTH: 20
<212> TYPE: DNA
<213> ORGANISM: Artificial sequence
<220> FEATURE:
<223> OTHER INFORMATION: PCR primer 17F

<400> SEQUENCE: 103
gggtccccca gtccttccag                                           20

<210> SEQ ID NO 104
<211> LENGTH: 17
<212> TYPE: DNA
<213> ORGANISM: Artificial sequence
<220> FEATURE:
<223> OTHER INFORMATION: PCR primer 17R

<400> SEQUENCE: 104
tccccagccc gcccaca                                              17

<210> SEQ ID NO 105
<211> LENGTH: 20
<212> TYPE: DNA
<213> ORGANISM: Artificial sequence
<220> FEATURE:
<223> OTHER INFORMATION: PCR primer 18F

<400> SEQUENCE: 105
```

-continued gcccctcac cacccttct                     20

<210> SEQ ID NO 106
<211> LENGTH: 18
<212> TYPE: DNA
<213> ORGANISM: Artificial sequence
<220> FEATURE:
<223> OTHER INFORMATION: PCR primer 18R

<400> SEQUENCE: 106
tcccgctgct cccccac                      18

<210> SEQ ID NO 107
<211> LENGTH: 18
<212> TYPE: DNA
<213> ORGANISM: Artificial sequence
<220> FEATURE:
<223> OTHER INFORMATION: PCR primer 19F

<400> SEQUENCE: 107
gatgccgtgg ggaccgtc                     18

<210> SEQ ID NO 108
<211> LENGTH: 20
<212> TYPE: DNA
<213> ORGANISM: Artificial sequence
<220> FEATURE:
<223> OTHER INFORMATION: PCR primer 19R

<400> SEQUENCE: 108
gtgagcaggt ggcagtctcg                   20

<210> SEQ ID NO 109
<211> LENGTH: 21
<212> TYPE: DNA
<213> ORGANISM: Artificial sequence
<220> FEATURE:
<223> OTHER INFORMATION: PCR primer 20F

<400> SEQUENCE: 109 ccacccctc tgctcgtagg t                  21

<210> SEQ ID NO 110
<211> LENGTH: 19
<212> TYPE: DNA
<213> ORGANISM: Artificial sequence
<220> FEATURE:
<223> OTHER INFORMATION: PCR primer 20R

<400> SEQUENCE: 110
ggtcccaagc acgcatgca                    19

<210> SEQ ID NO 111
<211> LENGTH: 22
<212> TYPE: DNA
<213> ORGANISM: Artificial sequence
<220> FEATURE:
<223> OTHER INFORMATION: PCR primer 21F

<400> SEQUENCE: 111
tgccggcctc ctgcgctgct ga                22

<210> SEQ ID NO 112
<211> LENGTH: 28
<212> TYPE: DNA
<213> ORGANISM: Artificial sequence -continued

```
<220> FEATURE:
<223> OTHER INFORMATION: PCR primer TWR2-1

<400> SEQUENCE: 112
gtaggatggc cccacctgct caccctgc                                          28

<210> SEQ ID NO 113
<211> LENGTH: 20
<212> TYPE: DNA
<213> ORGANISM: Artificial sequence
<220> FEATURE:
<223> OTHER INFORMATION: PCR primer R27'

<400> SEQUENCE: 113
aggtcaacgt gggcctccaa                                                   20
```

DETECTION AND TREATMENT OF POLYCYSTIC KIDNEY DISEASE

This application claims the benefit of priority under 35 U.S.C. § 119(e) of U.S. Ser. No. 60/218,261, filed Jul. 13, 2000, and U.S. Ser. No. 60/283,691, filed Apr. 13, 2001, the entire contents of each of which is incorporated herein by reference.

This invention was made in part with government support under Grant Nos. DK48006, TW05393, and DK02562 awarded by the National Institutes of Health. The government has certain rights in the invention.

BACKGROUND OF THE INVENTION

1. Field of the Invention

The present invention relates generally to the diagnosis and treatment of polycystic kidney disease and more specifically to probes and agents useful in diagnosing and treating polycystic kidney disease and related disorders.

2. Background Information

Autosomal dominant polycystic kidney disease (ADPKD), also called adult-onset polycystic kidney disease, is one of the most common hereditary disorders in humans, affecting approximately one individual in a thousand. The prevalence in the United States is greater than 500,000, with 6,000 to 7,000 new cases detected yearly (Striker et al., Am. J. Nephrol. 6:161-164, 1986; Iglesias et al., Am. J. Kid. Dis. 2:630-639, 1983). The disease is considered to be a systemic disorder, characterized by cyst formation in the ductal organs such as kidney, liver, and pancreas, as well as by gastrointestinal, cardiovascular, and musculoskeletal abnormalities, including colonic diverticulitis, berry aneurysms, hernias, and mitral valve prolapse (Gabow et al., Adv. Nephrol. 18:19-32, 1989; Gabow, New Eng. J. Med. 329:332-342, 1993).

The most prevalent and obvious symptom of ADPKD is the formation of kidney cysts, which result in grossly enlarged kidneys and a decrease in renal-concentrating ability. In approximately half of ADPKD patients, the disease progresses to end-stage renal disease, and ADPKD is responsible for 4-8% of the renal dialysis and transplantation cases in the United States and Europe (Proc. Eur. Dialysis and Transplant Assn., Robinson and Hawkins, eds., 17:20, 1981).

Few diagnostics are available for the identification and characterization of mutations of the PKD1 gene, which is located on human chromosome 16. A major factor contributing to the difficulty in identifying and characterizing mutations of the PKD1 gene is that greater than 70% of the length of the PKD1 gene is replicated on chromosome 16 and elsewhere, resulting in at least six PKD1 homologs. Significantly, the PKD1 homologs share a very high sequence identity with the PKD1 gene, including sequences having greater than 95% identity with the PKD1 gene. As such, oligonucleotides that have been examined for use as specific probes, or as primers for amplification, of PKD1 gene sequences have been found to cross-hybridize with the PKD1 homologs, and the inability to identify PKD1 locus specific probes has prevented accurate analysis of PKD1 gene mutations.

The identification and characterization of PKD1 gene mutations have been further hindered, in part, because transcription of the PKD1 gene results in production of a 14 kilobase (kb) mRNA, which is highly GC-rich. In addition, unlike the remainder of the PKD1 gene, which is extremely compact (approximately 13.5 kb mRNA coded within approximately 30 kb genomic DNA), exon 1 is separated from the rest of the gene by an intron of approximately 19 kb. Thus, previous investigators have simply placed the 5' anchor primer within the first intron and used it as a link to more 3' sequences. Exon 1 has several other features that have been major obstacles to its amplification, including an extremely high GC content (approximately 85%), and the ability to replicate with high fidelity in PKD1 gene homologs. Furthermore, no effective method for DNA based analysis of PKD1 gene exon 22, which is flanked on both ends by introns that contain lengthy polypyrimidine tracts. Accordingly, very few positions within the replicated segment and flanking exon 22 are suitable for the design of PKD1-specific primers.

A few oligonucleotides useful for examining regions of the human PKD1 gene, have been described. For example, the primer set forth below as SEQ ID NO:11 has been described in U.S. Pat. No. 6,017,717, and the primer set forth as SEQ ID NO:18 has been described by Watnick et al. (Hum. Mol. Genet. 6:1473-1481, 1997). Also, the primers set forth below as SEQ ID NOS:9, 10, 49 to 51, and 61 to 105 have been described by Watnick et al. (Am. J. Hum. Genet. 65:1561-1571, 1999). The primers set forth below as SEQ ID NOS: 9 and 10 and SEQ ID NOS: 11 and 12 also were more recently described by Phakdeekitcharoen et al. (Kidney International 58:1400-1412, 2000). In addition, a primer set forth as SEQ ID NO:13 in U.S. Pat. No. 6,071,717 has a nucleotide sequence that is substantially identical to that set forth below as SEQ ID NO:10, and a primer designated TWR2 by Watnick et al. (Mol. Cell 2:247-251, 1998) has a nucleotide sequence that is substantially identical to that set forth below as SEQ ID NO:12.

Despite the large number of families having diseases associated with PKD1 gene mutations, the potential clinical and scientific impact of mutation studies, and the availability of a genomic structure, the fact that only a relatively small number of PKD1 mutations have been described demonstrates the relative paucity of data due to the complicated genomic structure of the PKD1 gene. Thus, there exists a need for diagnostic methods suitable for examining the PKD1 gene and for identifying disorders related to PKD1 gene mutations. The present invention satisfies this need and provides additional advantages.

SUMMARY OF THE INVENTION

The present invention provides compositions and methods that allow for the selective examination of the human PKD1 gene, including the detection and identification of PKD1 gene mutations. For example, the compositions of the invention include oligonucleotide primers that are useful for selectively amplifying a region of a PKD1 gene, but not a corresponding region of a PKD1 homolog. Accordingly, the present invention relates to a PKD1 gene specific primer, which can be one of a primer pair. A primer of the invention includes a 5' region and adjacent PKD1-specific 3' region, wherein the 5' region has a nucleotide sequence that can hybridize to a PKD1 gene sequence and, optionally, to a PKD1 homolog sequence, and the 3' region has a nucleotide sequence that selectively hybridizes only to a PKD1 gene sequence, and particularly not to a PKD1 gene homolog sequence, except that a primer of the invention does not have a sequence as set forth in SEQ ID NO:11, SEQ ID NO:18, SEQ ID NO:52, or SEQ ID NO:60. A 5' region of a primer of the invention generally contains at least about ten contiguous nucleotides, and the 3' region contains at least one 3' terminal nucleotide, wherein the at least one 3' terminal nucleotide is identical to a nucleotide that is 5' and adjacent to the nucleotide sequence of the PKD1 gene to which the 5' region of the primer can hybridize, and is different from a nucleotide that is 5' and adjacent to a nucleotide sequence of the PKD1 homolog to which the 5' region of the primer can hybridize. Generally, the primer includes a 5' region of about 14 to 18 nucleotides and a 3' region of about 2 to 6 nucleotides, particularly about 2 to 4 nucleotides. For example, a primer of the invention can have a sequence as set forth in any of SEQ ID NOS:3 to 10, 12 to 17, 19 to 51 and 61 to 113.

The present invention also relates to an isolated mutant PKD1 polynucleotide, or an oligonucleotide portion thereof. The polynucleotides of the invention are exemplified by mutation of SEQ ID NO:1, which appear to be normal variants that are not associated with a PKD1-associated disorder, for example, a polynucleotide or oligonucleotide that includes nucleotide 474, wherein nucleotide 474 is a T; nucleotide 487, wherein nucleotide 487 is an A; nucleotide 9367, wherein nucleotide 9367 is a T; nucleotide 10143, wherein nucleotide 10143 is a G; nucleotide 10234, wherein nucleotide 10234 is a C; nucleotide 10255, wherein nucleotide 10255 is a T; or a combination thereof; and by mutations of SEQ ID NO:1 that are associated with a PKD1-associated disorder, for example, a polynucleotide or oligonucleotide that includes nucleotide 3110 of SEQ ID NO:1, wherein nucleotide 3110 is a C; nucleotide 8298 of SEQ ID NO:1, wherein nucleotide 8298 is a G; nucleotide 9164 of SEQ ID NO:1, wherein nucleotide 9164 is a G; nucleotide 9213 of SEQ ID NO:1, wherein nucleotide 9213 is an A; nucleotide 9326 of SEQ ID NO:1, wherein nucleotide 9326 is a T; nucleotide 10064 of SEQ ID NO:1, wherein nucleotide 10064 is an A; or a combination thereof. The invention also provides a vector containing such a polynucleotide, or an oligonucleotide portion thereof, and provides a host cell containing such a polynucleotide or oligonucleotide, or vector.

A PKD1-specific primer of the invention is exemplified by an oligonucleotide that can selectively hybridize to a nucleotide sequence that flanks and is within about fifty nucleotides of a nucleotide sequence selected from about nucleotides 2043 to 4290; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320 of SEQ ID NO:1. The primer, which can be one of a primer pair, can have a nucleotide sequence substantially identical to any of SEQ ID NOS: 3 to 18, provided that when the primer is not one of a primer pair, the primer does not have a sequence as set forth in SEQ ID NO:11, SEQ ID NO:18, SEQ ID NO:52, or SEQ ID NO:60. Accordingly, the present invention further relates to a primer pair that can amplify a portion of a PKD1 gene, for example, the wild type PKD1 gene set forth as SEQ ID NO:1, wherein the amplification product can include about nucleotides 2043 to 4290; nucleotides 17907 to 22489; nucleotides 22218 to 26363; nucleotides 26246 to 30615; nucleotides 30606 to 33957; nucleotides 36819 to 37140; nucleotides 37329 to 41258; nucleotides 41508 to 47320; or a combination thereof. A primer pair of the invention is useful for performing PKD1-specific amplification of a portion of a PKD1 gene.

Primer pairs of the invention are exemplified by a pair including at least one forward primer and at least one reverse primer of the oligonucleotides sequences set forth in SEQ ID NOS:3 to 18 or a sequence substantially identical thereto. In one embodiment, the primer pair includes SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 113. Also provided are primer pairs useful for performing nested amplification of a PKD1-specific amplification product of a PKD1 gene, for example, the primer pairs set forth as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS:105 and 106; SEQ ID NOS:107 and 108; SEQ ID NOS:109 and 110; or SEQ ID NOS:111 and 112. In another embodiment, the invention relates to a plurality of primer pairs, which can include two or more primer pairs that are useful for generating two or more PKD1-specific amplification products of a PKD1 gene; or can include two or more primer pairs that are useful for generating a PKD1-specific amplification product of a PKD1 gene and for generating a nested amplification product of the PKD1-specific amplification product.

The present invention also relates to a purified mutant PKD1 polypeptide, or a peptide portion thereof, comprising an amino acid sequence of a mutant of SEQ ID NO:2. A mutant PKD1 polypeptide, or peptide portion thereof can be substantially identical to a sequence of SEQ ID NO:2 and, for example, include amino acid residue 88 of SEQ ID NO:2, wherein residue 88 is a V; residue 967 of SEQ ID NO:2, wherein residue 967 is an R; residue 2696 of SEQ ID NO:2, wherein residue 2696 is an R; residue 2985 of SEQ ID NO:2, wherein residue 2985 is a G; residue 3039 of SEQ ID NO:2, wherein residue 3039 is a C; residue 3285 of SEQ ID NO:2, wherein residue 3285 is an I; or residue 3311 of SEQ ID NO:2, wherein residue 3311 is an R; or can include residue 3000 of a truncated mutant PKD1 polypeptide ending at amino acid residue 3000 with respect to SEQ ID NO:2, wherein residue 3001 is absent (and the mutant PKD1 polypeptide is truncated) due to the presence of a STOP codon in the encoding mutant PKD1 polynucleotide; or a combination of such mutations. Also provided is a purified antibody that specifically binds to a mutant PKD1 polypeptide, or to a peptide thereof.

The present invention further relates to a primer or an oligonucleotide of the invention immobilized to a solid support. In addition, the primer or oligonucleotide can be one of a plurality of primers, oligonucleotides, or a combination thereof, each of which is immobilized to a solid support. The solid support can be any support, including, for example, a microchip, in which case, the primers, oligonucleotides, or combination thereof can be arranged in array, particularly an addressable array. The primers, oligonucleotides, or combination thereof also can be degenerate with respect to each other, and specific for a wild type PKD1 polynucleotide, a mutant PKD1 polynucleotide, including a variant, or combinations thereof, and, therefore, provide a means for multiplex analysis. Accordingly, the present invention provides compositions comprising one or a plurality of immobilized primers or oligonucleotides of the invention, or combinations thereof.

The present invention also relates to a method of detecting a PKD1 polynucleotide in a sample, wherein the PKD1 polynucleotide is a wild type PKD1 polynucleotide having a sequence as set forth in SEQ ID NO:1, or a mutant PKD1 polynucleotide, which can be a variant PKD1 polynucleotide that has a sequence different from SEQ ID NO:1 but is not associated with a PKD1-associated disorder or can be a mutant PKD1 polynucleotide that is associated with a PKD1-associated disorder. A method of the invention can be performed, for example, by contacting nucleic acid molecules in a sample suspected of containing a PKD1 polynucleotide with at least one primer pair under conditions suitable for amplification of a PKD1 polynucleotide by the primer pair; and generating a PKD1-specific amplification product under said conditions, thereby detecting a PKD1 polynucleotide in the sample. The primer pair can be any primer pair as disclosed herein, for example, a primer pair such as SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 113; or can be a combination of such primer pairs.

A method of detecting a PKD1 polynucleotide can further include, upon generating a PKD1-specific amplification product, contacting the amplification product with at least a second primer pair, under conditions suitable for nested amplification of the PKD1-specific amplification product by the second primer pair, and generating a nested amplification product. The second primer pair can be any primer pair that can produce a nested amplification product of the PKD1-specific amplification product, for example, a second primer pair such as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; primer pairs formed using consecutive primers set forth in Table 2 as SEQ ID NOS:62 to 96, 113, and 97 to 112; or a combination thereof.

Upon detecting a PKD1 polynucleotide in a sample according to a method of the invention, an additional step of detecting the presence or absence of a mutation in an amplification product of the PKD1 polynucleotide in the sample as compared to a corresponding nucleotide sequence in SEQ ID NO:1. As such, a method of the invention provides a means to identify a PKD1 polynucleotide in a sample as a mutant PKD1 polynucleotide or a wild type PKD1 polynucleotide, wherein detecting the absence of a mutation in the amplification product identifies the PKD1 polynucleotide in the sample as a wild type PKD1 polynucleotide, and wherein detecting the presence of a mutation in the amplification product identifies the PKD1 polynucleotide in the sample as a mutant PKD1 polynucleotide, which can be a variant PKD1 polynucleotide, or can be mutant PKD1 polynucleotide associated with a PKD1-associated disorder, the latter of which are exemplified by a polynucleotide that is substantially identical to SEQ ID NO:1, and wherein at least nucleotide 474 is a T; nucleotide 487 is an A; nucleotide 3110 is a C; nucleotide 8298 is a G; nucleotide 9164 is a G; nucleotide 9213 is an A; nucleotide 9326 is a T; nucleotide 9367 is a T; nucleotide 10064 is an A; nucleotide 10143 is a G; nucleotide 10234 is a C; or nucleotide 10255 is a T.

The presence or absence of a mutation in an amplification product generated according to a method of the invention can be detected any method useful for detecting a mutation. For example, the nucleotide sequence of the amplification product can be determined, and can be compared to the corresponding nucleotide sequence of SEQ ID NO:1. The melting temperature of the amplification product also can be determined, and can be compared to the melting temperature of a corresponding double stranded nucleotide sequence of SEQ ID NO:1. The melting temperature can be determined using a method such as denaturing high performance liquid chromatography.

An advantage of a method of the invention is that a large number of samples can be examined serially or in parallel. Accordingly, a method of the invention can be performed with respect to a plurality of samples, and can be performed using a high throughput format, for example, by organizing the samples of a plurality of samples in an array such as in an array is on a microchip. The method can further include detecting the presence or absence of a mutation in an amplification product of the samples of the plurality of samples, for example, by determining the melting temperature of the amplification product and comparing it to the melting temperature of a corresponding nucleotide sequence of SEQ ID NO:1 using a method such as denaturing high performance liquid chromatography, or the presence or absence of a mutation can be performed using any method useful for such a purpose, for example, matrix-assisted laser desorption time of flight mass spectrometry or high throughput conformation-sensitive gel electrophoresis, each of which is readily adaptable to a high throughput analysis format.

In another embodiment, the presence or absence of a mutation in an amplification product can be detected by contacting the amplification product with the oligonucleotide of the invention, under condition suitable for selective hybridization of the oligonucleotide to an identical nucleotide sequence; and detecting the presence or absence of selective hybridization of the oligonucleotide to the amplification product. Using such a method detecting the presence of selective hybridization identifies the PKD1 polynucleotide in the sample as a mutant PKD1 polynucleotide, and detecting the absence of selective hybridization identifies the PKD1 polynucleotide as a wild type PKD1 polynucleotide. Where an absence of a mutation is detected, the PKD1 polynucleotide in the sample is identified as a wild type PKD1 polynucleotide. In comparison, where the presence of a mutation is identified, the mutant PKD1 polynucleotide so identified can be further examined to determine whether the mutant PKD1 polynucleotide is a variant PKD1 polynucleotide, which is associated with a normal phenotype with respect to PKD1, for example, where the amplification product has a nucleotide sequence substantially identical to SEQ ID NO:1, and including C474T, G487A, G4885A; C6058T; G6195A; T7376C; C7696T; G8021A; C9367T, A10143G, T10234C, or a combination thereof, or is a mutant PKD1 polynucleotide associated with a PKD1-associated disorder, for example, where the amplification product has a nucleotide sequence substantially identical to SEQ ID NO:1, and including T3110C, G3707A; T6078A; C7433T; T8298G; A9164G; G9213A, C9326T; G10064A; an insertion of GCG between nucleotides G7535 and A7536; or a combination thereof, each of which is associated with ADPKD (see Example 2; see, also, Phakdeekitcharoen et al., Kidney International 58:1400-1412, 2000, which is incorporated herein by reference).

The present invention further relates to a method of detecting the presence of a mutant PKD1 polynucleotide in a sample. In one embodiment, a method of the invention is performed by amplifying a nucleic acid sequence in a sample suspected of containing a mutant PKD1 polynucleotide using a primer pair of the invention, for example, a primer pair selected from SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; or SEQ ID NOS:9 and 13, thereby obtaining a PKD1-specific amplification product of a PKD1 gene sequence; and detecting a mutant PKD1 polynucleotide in the amplification product. The mutant PKD1 nucleotide in the amplification product can be detected using any method useful for detecting a mutation in a polynucleotide, for example, using denaturing high performance liquid chromatograph. In another embodiment, a method of the invention is performed by contacting a sample suspected of containing a mutant PKD1 polynucleotide with a probe comprising an isolated polynucleotide of the invention, or an oligonucleotide portion thereof, under conditions such that the probe selectively hybridizes to a mutant PKD1 polynucleotide, and detecting specific hybridization of the probe and a PKD1 polynucleotide, thereby detecting the presence of a mutant PKD1 polynucleotide sequence in the sample.

The present invention further relates to a method of identifying a subject having or is at risk of having a PKD1-associated disorder. Such a method can be performed, for example, by contacting nucleic acid molecules in a sample from a subject with at least one primer pair of the invention under conditions suitable for amplification of a PKD1 polynucleotide by the primer pair, thereby generating an amplification product; and testing an amplification product for the presence or absence of a mutation indicative of a PKD1-associated disorder. As disclosed herein, the absence of such a mutation identifies the subject as not having or at risk of the having a PKD1-associated disorder, wherein the presence of such a mutation identifies the subject as having or is at risk of having a PKD1-associated disorder, for example, ADPKD or acquired cystic disease.

A primer pair useful in a diagnostic method of the invention can include at least one primer pair selected from SEQ ID NO:3 and 4; SEQ ID NO:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113. The subject can be any subject having a PKD1 gene and susceptible to a PKD1-associated disorder, including a vertebrate subject, and particularly a mammalian subject such as a cat or a human. In addition, the diagnostic method can be performed in a high throughput format, thereby allowing the examination of a large number samples in a cost-effective manner.

The diagnostic method can further include contacting the amplification product generated as described above with at least a second primer pair, under conditions suitable for nested amplification of the amplification product by a second primer pair, thereby generating a nested amplification product. The second primer pair can be, for example, a primer pair selected from SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; a primer pair formed using two consecutive primers set forth in Table 2 as SEQ ID NOS:62 to 96,113, and 97 to 112 (i.e., SEQ ID NOS:62 and 63, SEQ ID NOS:64 and 65, and so on); and a combination thereof, in which case, the step of testing the amplification product for the presence or absence of a mutation comprises testing the nested amplification product. It should be recognized that the selection of a primer pair for nested amplification is based, in part, on the sequence of the PKD1-specific amplification product that is to be used as a template for the nested amplification, i.e., nested primer pairs are selected such that they can hybridize to a target PKD1-specific amplification product and can amplify the target sequence.

An amplification product can be tested for the presence or absence of the mutation, for example, by determining the nucleotide sequence of the amplification product, and comparing it to a corresponding nucleotide sequence of SEQ ID NO:1; by determining the melting temperature of the amplification product, and comparing it to the melting temperature of a corresponding nucleotide sequence of SEQ ID NO:1, for example, using a method such as denaturing high performance liquid chromatography; or by contacting the amplification product with an oligonucleotide probe containing nucleotide 474 of SEQ ID NO:1, wherein nucleotide 474 is a T; nucleotide 487 of SEQ ID NO:1, wherein nucleotide 487 is an A; nucleotide 3110 of SEQ ID NO:1, wherein nucleotide 3110 is a C; nucleotide 8298 of SEQ ID NO:1, wherein nucleotide 8298 is a G; nucleotide 9164 of SEQ ID NO:1, wherein nucleotide 9164 is a G; nucleotide 9213 of SEQ ID NO:1, wherein nucleotide 9213 is an A; nucleotide 9326 of SEQ ID NO:1, wherein nucleotide 9326 is a T; nucleotide 9367 of SEQ ID NO:1, wherein nucleotide 9367 is a T; nucleotide 10064 of SEQ ID NO:1, wherein nucleotide 10064 is an A; nucleotide 10143 of SEQ ID NO:1, wherein nucleotide 10143 is a G; nucleotide 10234 of SEQ ID NO:1, wherein nucleotide 10234 is a C; and nucleotide 10255 of SEQ ID NO:1, wherein nucleotide 10255 is a T, under conditions suitable for selective hybridization of the probe to a mutant PKD1 polypeptide, which can be a normal variant or can be a mutant PKD1 polynucleotide associated with a PKD1-associated disorder.

The present invention also relates to a method of diagnosing a PKD1-associated disorder in a subject suspected of having a PKD1-associated disorder. Such a method is performed by amplifying a nucleic acid sequence in a sample obtained from the subject using a primer pair suitable for PKD1-specific amplification of a PKD1 gene sequence, for example, a primer pair such as SEQ ID NO:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18, or SEQ ID NOS:9 and 113, thereby obtaining a PKD1-specific first amplification product; and detecting a mutation of a PKD1 gene sequence in the PKD1-specific first amplification product, wherein the mutation is indicative of a PKD1-associated disorder, thereby diagnosing a PKD1-associated disorder in the subject.

In one embodiment, the diagnostic method includes a step of further amplifying the first amplification product using a second set of primer pairs to obtain a nested amplification product; and detecting a PKD1 gene mutation in the nested amplification product. The second set of primer pairs can be any primer pairs useful for amplifying the PKD1-specific first amplification product, including, for example, the primer pairs exemplified by SEQ ID NOS:19 and 20; SEQ ID NOS: 21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; or any of the primer pairs formed using consecutive primers set forth in Table 2 as SEQ ID NOS:62 to 96, 113, and 97 to 112.

In another method, the diagnostic method includes a step of contacting the PKD1-specific first amplification product or second amplification product with a probe comprising an isolated polynucleotide, or an oligonucleotide portion thereof, comprising a mutant of SEQ ID NO:1, under conditions such that the probe can selectively hybridize to a mutant PKD1 polynucleotide; and detecting selective hybridization of the probe to the first amplification product, thereby diagnosing a PKD1-associated disorder in the subject. The probe can be, for example, an oligonucleotide portion of SEQ ID NO:1 that includes one or more of nucleotide 474 is a T; nucleotide 487 is an A; nucleotide 3110 is a C; nucleotide 8298 is a G; nucleotide 9164 is a G; nucleotide 9213 is an A; nucleotide 9326 is a T; nucleotide 9367 is a T; nucleotide 10064 is an A; nucleotide 10143 is a G; nucleotide 10234 is a C; or nucleotide 10255 is a T.

The present invention also relates to a method of detecting the presence of a mutant PKD1 polypeptide in a sample. Such a method can be performed, for example, by contacting a sample suspected of containing a mutant PKD1 polypeptide with an antibody that specifically binds to a mutant PKD1 polypeptide, under conditions which allow the antibody to bind to the mutant PKD1 polypeptide and detecting specific binding of the antibody and the mutant PKD1 polypeptide in the sample. The detection of an immunocomplex of the antibody and a mutant PKD1 polypeptide, for example, indicates the presence of a mutant PKD1 polypeptide in the sample. In one embodiment, the method is performed by contacting a tissue sample from a subject suspected of containing a PKD1 polypeptide with the antibody that specifically binds a mutant PKD1 polypeptide under conditions that allow the antibody interact with a PKD1 polypeptide and detecting specific binding of the antibody and the PKD1 polypeptide in the tissue.

The present invention further relates to a kit for detecting a mutant PKD1 polynucleotide, which can be a variant PKD1 polynucleotide or a mutant PKD1 polynucleotide associated with a PKD1-associated disorder. The kit can contain, for example, a carrier means containing therein one or more containers wherein a first container contains a nucleotide sequence useful for detecting a wild type or mutant PKD1 polynucleotide. As such, a nucleotide sequence useful in a kit of the invention can be an oligonucleotide comprising at least ten contiguous nucleotides of SEQ ID NO:1, including at least one of nucleotide 474, wherein nucleotide 474 is a T; nucleotide 487, wherein nucleotide 487 is an A; nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. A nucleotide sequence useful in a kit of the invention also can comprise one or both primers of a primer pair, particularly at least a forward primer and a reverse primer as set forth in SEQ ID NOS:3 to 18; and the kit can further include at least a second primer pair, including a forward and reverse primer as set forth in SEQ ID NOS:19 to 51 and 61 to 113. In another aspect, the present invention relates to a kit containing an antibody that specifically binds to a mutant PKD1 polypeptide or peptide portion thereof.

DETAILED DESCRIPTION OF THE INVENTION

The present invention provides compositions and methods for identifying polycystic kidney disease-associated protein-1 (PKD1) gene variants and mutants, and for diagnosing PKD1-associated disorders in a subject. Prior to the present disclosure, the ability to selectively examine the entire PKD1 gene for mutations was precluded due to the high sequence homology of the PKD1 gene and the PKD1 gene homologs, including those present with the PKD1 gene on human chromosome 16. As disclosed herein, polynucleotide sequences have now been developed that are useful as probes and primers for examining the entire PKD1 gene. Accordingly, the present invention provides polynucleotides, and oligonucleotide portions thereof, of a PKD1 gene and of PKD1 gene mutants that are useful for detecting PKD1 mutations, and that can be diagnostic of a PKD1-associated disorder.

Autosomal dominant polycystic kidney disease (ADPKD) exhibits a transmission pattern typical of autosomal dominant inheritance, where typically each offspring of an affected individual has a 50% chance of inheriting the causative gene. Linkage studies indicated that a causative gene is present on the short arm of chromosome 16, near the α globin cluster; this locus was designated PKD1 (Reeders et al., Nature, 317:542, 1985.) Though other PKD-associated genes exist (for example, PKD2), defects in PKD1 appear to cause ADPKD in about 85-90% of affected families (Parfrey et al., New Eng. J. Med. 323:1085-1090, 1990; Peters et al., Contrib. Nephrol. 97:128-139, 1992).

The PKD1 gene has been localized to chromosomal position 16p13.3, specifically to an interval of approximately 600 kb between the markers ATPL and CMM65 (D16S84). This region is rich in CpG islands that often flank transcribed sequences; it has been estimated that this interval contains at least 20 genes. The precise location of the PKD1 gene was pinpointed by the finding of an ADPKD family whose affected members carry a translocation that disrupts a 14 kb RNA transcript associated with this region (European PKD Consortium, Cell, 77:881, 1994).

Figure 1:
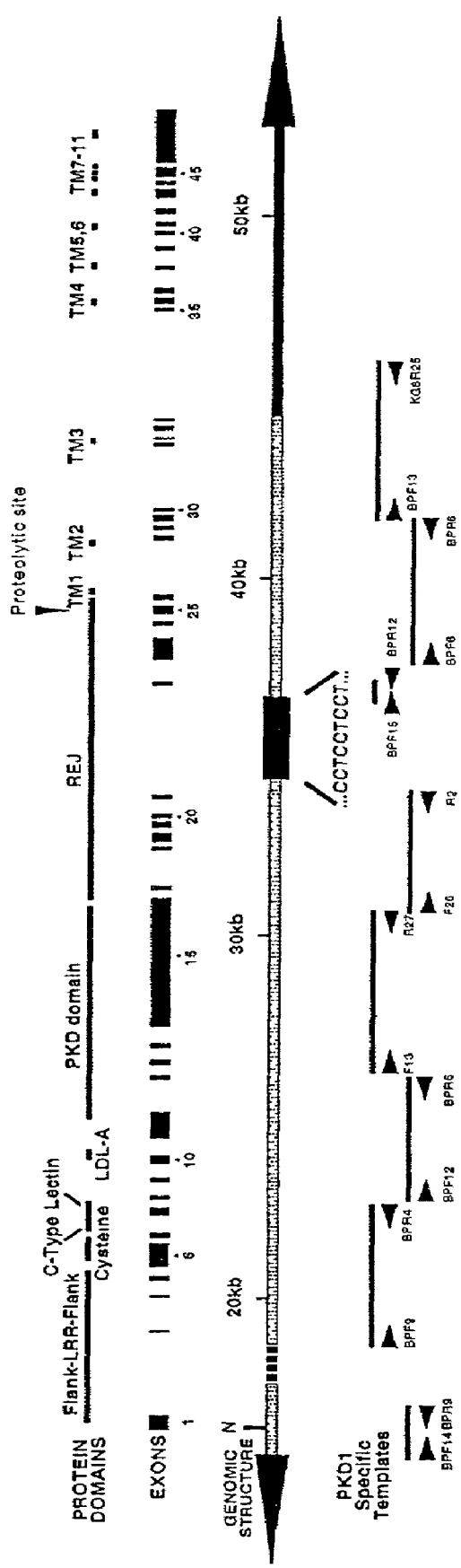
FIG. 1 is a schematic showing the genomic structure of the PKD1 gene (SEQ ID NO:1) and the relative position of locus-specific templates and primers.

The genomic structure of the PKD1 gene, which is illustrated in FIG. 1 (SEQ ID NO:1; see Appendix A; see, also, GenBank Accession No. L39891, which is incorporated herein by reference), extends over approximately 50 kb, contains 46 exons, and is bisected by two large polypyrimidine tracts of approximately 2.5 kb and 0.5 kb, respectively, in introns 21 and 22 (indicated by "... CCTCCTCCT ..." in FIG. 1). The replicated portion of the gene, which begins prior to the 5'UTR and is believed to end in exon 34 (FIG. 1; stippled region), covers approximately two thirds of the 5' end of the gene and is duplicated several times in a highly similar, transcribed fashion elsewhere in the human genome (Germino et al., Genomics 13:144-151, 1992; European Chromosome 16 Tuberous Sclerosis Consortium, 1993, Cell 75:1305-1315). The encoded PKD1 polypeptide is shown as SEQ ID NO:2 (see Appendix A; see, also, GenBank Accession No. P98161, which is incorporated herein by reference). It should be recognized that SEQ ID NO:2 is not the same amino acid sequence as that shown to be encoded by GenBank Accession No. L39891 (see, also, GenBank AAB59488), presumably due to errors in predicting the encoded PKD1 polypeptide from the PKD1 gene sequence. Instead, the wild type PKD1 polypeptide sequence is shown in SEQ ID NO:2 (GenBank Accession No. P98161).

The present invention provides a PKD1 gene specific primer, which can be one of a primer pair. A primer of the invention includes a 5' region and adjacent PKD1-specific 3' region, wherein the 5' region has a nucleotide sequence that can hybridize to a PKD1 gene sequence or to a PKD1 gene sequence and a PKD1 gene homolog sequence, and the 3' region has a nucleotide sequence that selectively hybridizes only to a PKD1 gene sequence, and particularly not to a PKD1 gene homolog sequence, except that a primer of the invention does not have a sequence as set forth in SEQ ID NO:11, SEQ ID NO:18, SEQ ID NO:52, or SEQ ID NO:60. Thus, a primer of the invention can have a sequence as set forth in any of SEQ ID NOS:3, 4, 5, 6, 7, 8, 9, 10, 12, 13, 14, 15, 16, 17, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112 and 113, as well as a sequence that is substantially identical to any of SEQ ID NOS:3 to 51 and 61 to 113, provided the sequence comprises a 5' region that can hybridize to a PKD1 gene sequence or to a PKD1 gene sequence and a PKD1 gene homolog sequence, and a 3' region that selectively hybridizes to a PKD1 gene sequence, but not to a PKD1 gene homolog sequence; and provided the sequence is not otherwise specifically excluded herein.

As disclosed herein, a primer of the invention can be prepared by aligning SEQ ID NO:1 with the PKD1 gene homologs contained in GenBank Accession Nos. AC002039, AC010488, AC040158, AF320593 and AF320594 (each of which is incorporated herein by reference; see, also, Bogdanova et al., Genomics 74:333-341, 2001, which is incorporated herein by reference) and identifying regions having potential sequence differences, then selecting as PKD1-specific primers those sequences that match over at least about ten nucleotides and that have a mismatch at or adjacent to the 3' terminus of the matched regions (see Example 1; see, also, Phakdeekitcharoen et al., supra, 2000). Such primers are referred to as "PKD1-specific primers" because, while they can hybridize to a PKD1 gene and a PKD1 gene homologue, an extension product only can be generated upon hybridization to a PKD1 gene due to the mismatch of one or more nucleotides in the 3' region when the primer hybridizes to a PKD1 gene homologue. Confirmation that a selected oligonucleotide is a PKD1-specific primer can be made using methods as disclosed herein (Example 1) or otherwise known in the art. For example, a simple and straightforward method for determining that a primer is a PKD1-specific primer of the invention is to perform a primer extension or an amplification reaction using the putative PKD1-specific primer and templates including a PKD1 gene sequence and PKD1 gene homolog sequences, and detecting a single extension product or amplification product generated from the PKD1 gene template, but not the PKD1 gene homolog templates. Sequences identified as PKD1-specific primers using this or another method can be confirmed by performing various control experiments as described by Watnick et al. (supra, 1999), for example, by comparing an amplification product obtained in a cell having a PKD1 gene with the products, if any, produced using the radiation hybrid cell line, 145.19, which lacks the PKD1 gene but contains PKD1 gene homologs.

A nucleotide sequence suspected of being useful as a PKD1-specific primer also can be compared against a human genomic DNA database using, for example, a BLAST search or other algorithm, to confirm that the nucleotide sequence meets the requirements of a PKD1-specific primer as defined herein. For example, a putative PKD1-specific primer can be examined at the National Center for Biotechnology Information (NCBI), which can be accessed on the world wide web, by selecting the "Blast" option, thereafter selecting the "Search for short nearly exact matches," entering in the sequence to be examined, and, using the default search algorithms (word size 7), searching the "nr" database, which include all non-redundant GenBank+EMBL+DDBJ+PDB sequences, but no EST, SST, GSS or HTGS sequences; output can be restricted to showing only the top ten matches.

In a PKD1-specific primer of the invention, the 5' region contains at least about ten contiguous nucleotides, generally at least about 12 nucleotides, and usually about 14 to 18 nucleotides. In addition, the 3' region of the primer contains at least one 3' terminal nucleotide, and can include a sequence of at least about 2 to 6 nucleotides, particularly about 2 to 4 nucleotides. Where the 3' region consists of a single 3' terminal nucleotide, the primer is selected such that the 3' terminal nucleotide is identical to a nucleotide that is 5' and adjacent to the nucleotide sequence of the PKD1 gene to which the 5' region of the primer can hybridize, and is different from a nucleotide that is 5' and adjacent to a nucleotide sequence of the PKD1 homolog to which the 5' region of the primer can hybridize, i.e., provides a mismatched nucleotide. Where the 3' region of the PKD1-specific primer contains two or more nucleotides, one or more of the nucleotides can be mismatched, and the mismatched nucleotide can, but need not include the 3' terminal nucleotide, provided that when the mismatched nucleotide or nucleotides do not include the 3' terminal nucleotide, the primer cannot be extended when hybridized to a PKD1 gene homolog.

PKD1-specific primers of the invention are exemplified by primers that can selectively hybridize to a nucleotide sequence that flanks and is within about fifty nucleotides of a nucleotide sequence of SEQ ID NO:1 selected from about nucleotides 2043 to 4290; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320. A primer of the invention is exemplified by any of SEQ ID NOS: 3 to 10, 12 to 17, 19 to 51, and 61 to 113, and can have a sequence substantially identical to any of SEQ ID NOS:3 to 51 and 61 to 113, provided the sequence meets the requirements of a PKD1-specific primer as disclosed herein, and provided the sequence is not a sequence as set forth in any of SEQ ID NO:11, SEQ ID NO:18, SEQ ID NO:52, and SEQ ID NO:60.

A primer is considered to be "substantially identical" to any of SEQ ID NOS:3 to 51 and 61 to 113 if the primer has at least about 80% or 85%, generally at least about 90%, usually at least about 95%, and particularly at least about 99% sequence identity with one of SEQ ID NOS:3 to 51 and 61 to 113, and has a 5' region and adjacent PKD1-specific 3' region, wherein the 5' region has a nucleotide sequence that can hybridize to a PKD1 gene sequence or to a PKD1 gene sequence and a PKD1 gene homolog sequence, and the 3' region has a nucleotide sequence that selectively hybridizes only to a PKD1 gene sequence, and particularly not to a PKD1 gene homolog sequence, as defined herein, except that a primer of the invention does not have a sequence as set forth in SEQ ID NO:11, SEQ ID NO:18, SEQ ID NO:52, or SEQ ID NO:60. As such, a primer of the invention can include one or a few, but no more than about four or five, more or fewer nucleotide than a primer as set forth in SEQ ID NOS:3 to 51 and 61 to 113, provided the primer meets the functional requirements as defined herein.

The present invention also provides primer pairs. In one embodiment, a primer pair of the invention comprising a forward and reverse PKD1-specific primer as disclosed herein. As such, a primer pair of the invention can amplify a portion of SEQ ID NO:1 including about nucleotides 2043 to 4290; nucleotides 17907 to 22489; nucleotides 22218 to 26363; nucleotides 26246 to 30615; nucleotides 30606 to 33957; nucleotides 36819 to 37140; nucleotides 37329 to 41258; nucleotides 41508 to 47320; or a combination thereof. In general, a primer pair of the invention can produce an amplification product of about ten kilobases or shorter, generally about 7500 bases or shorter, and particularly about six kilobases or shorter. Primer pairs of the invention are exemplified by a forward primer and a reverse primer selected from SEQ ID NOS:3 to 18, for example, by any of SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113, which can be used to produce PKD1-specific amplification products of about 0.3 kilobases to about 5.8 kilobases.

As disclosed herein, a set of eight polymerase chain reaction (PCR) primer pairs can be used to prepare PKD1-specific amplification products that encompass all of the exons and their flanking introns within the replicated region of the PKD1 gene. In view of the disclosed nucleotide sequences of the primers and of SEQ ID NO:1, it will be recognized that additional PCR primer pairs useful for a preparing PKD1-specific first amplification product can be based on the exemplified primers and primer pairs, but can include one or few additional nucleotides (based on SEQ ID NO:1) at one or both ends of the exemplified primers, or can have one or a few nucleotides of an exemplified primer deleted, and their usefulness can be determined by comparing an amplification product generated using the derived or modified primer with a PKD1-specific amplification product as disclosed herein. As such, a primer pair based, for example, on SEQ ID NOS: 3 and 4 can be used to generate a PKD-1 specific amplification product containing about nucleotides 2043 to 4290 of SEQ ID NO:2, where in reference to "about" nucleotides 2043 to 4290 of SEQ ID NO:2 accounts for the disclosure that a primer pair used for amplification can be identical or substantially identical to SEQ ID NOS: 3 and 4.

Accordingly, the present invention provides primer pairs comprising a forward primer and a reverse primer having nucleotide sequences as set forth in SEQ ID NOS:3 to 18; primer pairs exemplified by SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and SEQ ID NOS:9 and 113; and substantially identical primer pairs that comprise primers based on or derived from the exemplified primers, such primer pairs being useful for preparing a PKD1-specific amplification product. The primer pairs shown as SEQ ID NOS: 9 and 10 and SEQ ID NOS: 11 and 12 have been described by Phakdeekitcharoen et al. (supra, 2000), as have the PKD1 specific amplification products generated using these primers.

It should be recognized that certain primers and certain primer pairs exemplified herein are not considered to be encompassed within the present invention. For example, the primer set forth in SEQ ID NO:11 has been described in U.S. Pat. No. 6,017,717 (which is incorporated herein by reference; column 24, SEQ ID NO:15); and the primer set forth in SEQ ID NO:18 has been described by Watnick et al. (Hum. Mol. Genet. 6:1473-1481, 1997, which is incorporated herein by reference; see page 1479; KG8R25), and, therefore, neither of these primers is considered to be a primer of the invention. Nevertheless, the primers set forth as SEQ ID NOS: 11 and 18 can be encompassed within the primer pairs of the invention, including within various disclosed and exemplified primer pairs, for example, the primer pairs set forth as SEQ ID NOS:11 and 12 and as SEQ ID NOS:17 and 18, as well as within combinations of two or more primer pairs, for example, a combination comprising SEQ ID NOS: 11 and 12 and SEQ ID NOS:13 and 14.

The primers set forth in SEQ ID NO:9 and SEQ ID NO:10 have been described by Watnick et al. (Am. J. Hum. Genet. 65:1561-1571, 1999, which is incorporated herein by reference) and, therefore, can be specifically excluded from certain embodiments of the invention, as desired, for example, as encompassed within the primers of the invention. It should be recognized, however, that the combination of SEQ ID NOS:9 and 10 as a primer pair is not described by Watnick et al. (supra, 1999). SEQ ID NOS:49 to 51 and 61 to 105 also have been described by Watnick et al. (supra, 1999) and, therefore, can be specifically excluded from certain embodiments of the invention, as desired.

Except as provided herein, a primer of the invention is exemplified by any of SEQ ID NOS:3 to 51 and 61 to 113, as well as substantially identical oligonucleotide primers that are based on or derived from SEQ ID NOS:3 to 51 and 61 to 113. It should be recognized, however, that the primer set forth as SEQ ID NO:12 is substantially similar to the primer designated TWR2 by Watnick et al. (Mol. Cell 2:247-251, 1998, which is incorporated herein by reference; page 250; 5'-GCAGGGTGAGCAGGTGGGGCCATCCTA-3'; SEQ ID NO:60), and that the primer set forth as SEQ ID NO:10 is substantially identical to SEQ ID NO:13 in U.S. Pat. No. 6,071,717 (5'-AGGTCAACGTGGGCCTCCAAGTAGT-3'; SEQ ID NO:52). As such, a primer having the nucleotide sequence of SEQ ID NO:52 or of SEQ ID NO:60 is specifically excluded from the primers that otherwise would be encompassed within the scope of primers that have a sequence substantially identical to the sequence of the primer set forth as SEQ ID NO:12 or SEQ ID NO:10, respectively.

The present invention also provides an isolated mutant PKD1 polynucleotide, or an oligonucleotide portion thereof comprising a mutation as disclosed herein. As used herein, the term "isolated" or "purified," when used in reference to a polynucleotide, oligonucleotide, or polypeptide, means that the material is in a form other than that in which it normally is found in nature. Thus, where a polynucleotide or polypeptide occurs in a cell in nature, an isolated polynucleotide or purified polypeptide can be one that separated, at least in part, from the materials with which it is normally associated. In general, an isolated polynucleotide or a purified polypeptide is present in a form in which it constitutes at least about 5 to 10% of a composition, usually 20% to 50% of a composition, particularly about 50% to 75% of a composition, and preferably about 90% to 95% or more of a composition. Methods for isolating a polynucleotide or polypeptide are well known and routine in the art.

As part of or following isolation, a polynucleotide can be joined to other polynucleotides, such as DNA molecules, for example, for mutagenesis studies, to form fusion proteins, or for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, nevertheless are considered "isolated" because they are not in a form in which they exist in nature. Similarly, the polynucleotides, oligonucleotides, and polypeptides can be present in a composition such as a media formulation (solutions for introduction of polynucleotides, oligonucleotides, or polypeptides, for example, into cells or compositions or solutions for chemical or enzymatic reactions which are not naturally occurring compositions) and, therein remain isolated polynucleotides, oligonucleotides, or polypeptides within the meaning of that term as it is employed herein. An isolated polynucleotide can be a polynucleotide that is not immediately contiguous with nucleotide sequences with which it is immediately contiguous in a genome or other naturally occurring cellular DNA molecule in nature. Thus, a recombinant polynucleotide, which can comprise a polynucleotide incorporated into a vector, an autonomously replicating plasmid, or a virus; or into the genomic DNA of a prokaryote or eukaryote, which does not normally express a PKD1 polypeptide.

As used herein, the term "polynucleotide" or "oligonucleotide" or "nucleotide sequence" or the like refers to a polymer of two or more nucleotides or nucleotide analogs. The polynucleotide can be a ribonucleic acid (RNA) or deoxyribonucleic acid (DNA) molecule, and can be single stranded or double stranded DNA or RNA, or a double stranded DNA: RNA hybrid. A polynucleotide or oligonucleotide can contain one or more modified bases, for example, inosine or a tritylated base. The bonds linking the nucleotides in a polymer generally are phosphodiester bonds, but can be other bonds routinely used to link nucleotides including, for example, phosphorothioate bonds, thioester bonds, and the like. A polynucleotide also can be a chemically, enzymatically or metabolically modified form.

As used herein, the term "mutant PKD1 polynucleotide" means a nucleotide sequence that has one or a few nucleotide changes as compared to the nucleotide sequence set forth as SEQ ID NO:1. The nucleotide change can be a deletion, insertion or substitution, and can be silent such that there is no change in the reading frame of a polypeptide encoded by the PKD1 polynucleotide, or can be a change that results in an amino acid change or in the introduction of a STOP codon into the polynucleotide, or a change in a nucleotide sequence involved in transcription or translation of the PKD1 polynucleotide, for example, a change that results in altered splicing of a PKD1 gene transcript into an mRNA (see Example 2). As disclosed herein, a mutant PKD1 polynucleotide can be a polymorphic variant, which, other than one or a few nucleotide changes with respect to SEQ ID NO:1, encodes a PKD1 polypeptide and does not correlate with a PKD1 associated disorder, particularly ADPKD, or can be a mutant PKD1 polynucleotide that contains one or more mutations that correlate with a PKD1 associated disorder such as ADPKD (see Example 2).

For convenience of discussion and for use as a frame of reference, the PKD1 nucleotide sequence set forth in SEQ ID NO:1 is referred to as a "wild type PKD1 polynucleotide" or a "wild type PKD1 gene" sequence, and, similarly, the polypeptide set forth as SEQ ID NO:2 is referred to as a "wild type PKD1 polypeptide." However, while the presence of the wild type PKD1 gene sequence (i.e., SEQ ID NO:1) in an individual correlates to the absence of ADPKD in the individual, it should be recognized that polymorphic variants of SEQ ID NO:1 also are found in individuals that do not exhibit ADPKD or other PKD1-associated disorder. The term "variants" or "polymorphic variants" is used herein to refer to mutant PKD1 polynucleotide sequences (with respect to SEQ ID NO:1) that do not correlate with the signs or symptoms characteristic of a PKD1 associated disorder such as ADPKD. Variant PKD1 polynucleotides include, for example, nucleotide substitutions that do not result in a change in the encoded amino acid, i.e., silent mutations, such as G4885A, in which the wild type and mutant codons both encode a threonine (T1558T), and C6058T, in which the wild type and mutant codons both encode a serine (S1949S; see Example 2; see, also, Phakdeekitcharoen et al., supra, 2000); those that do not segregate with the disease, or those that are found in a panel of unaffected individuals. As such, it should be recognized that the term "mutant PKD1 polynucleotide" broadly encompasses PKD1 variants, which do not correlate with a PKD1 associated disorder, as well as mutant PKD1 polynucleotides that correlate or are associated with a PKD11 associated disorder.

Examples of mutant PKD1 polynucleotide sequences, including variant PKD1 polynucleotide sequence, include sequences substantially as set forth in SEQ ID NO:1, but having a mutation at nucleotide 474, wherein nucleotide 474 is a T; nucleotide 487, wherein nucleotide 487 is an A; nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T; or a combination thereof (see Example 2; see, also, Tables 3 and 4). Examples of a mutant PKD1 polynucleotide of the invention also include a polynucleotide that encodes a PKD1 polypeptide having substantially as set forth in SEQ ID NO:2, but having an A88V, W967R, G1166S; V1956E; R1995H; R2408C; D2604N; L2696R, R2985G, R3039C, V3285I, H3311R mutation, or a combination thereof, as well as polypeptides that have, for example, an addition of a Gly residue between amino acid residues 2441 and 2442 of SEQ ID NO:2 due to an insertion, or that terminate with amino acid 3000 of SEQ ID NO:2 due to the presence of a STOP codon at the position in SEQ ID NO:1 that would otherwise encode amino acid 3001 (see, also, Table 4; Example 2).

Additional examples of mutant PKD1 polynucleotides of the invention include polynucleotide sequences that selectively hybridize to the complements of the polynucleotide sequences, or oligonucleotide portions thereof, as disclosed herein, under highly stringent hybridization conditions, e.g., hybridization to filter-bound DNA in 0.5M NaHPO$_4$, 7% sodium dodecyl sulfate (SDS), 1 mM EDTA at 65° C., and washing in 0.1× SSC/0.1% SDS at 68° C. (Ausubel et al., Current Protocols in Molecular Biology, (Green Publishing Associates, Inc., and John Wiley & Sons, Inc., New York 1989), and supplements; see p. 2.10.3; Sambrook et al., Molecular Cloning: A laboratory manual (Cold Spring Harbor Laboratory Press, 1989), which are incorporated herein by reference), as well as polynucleotides that encode a PKD1 polypeptide substantially as set forth in SEQ ID NO:2, but having one or more mutations; or an RNA corresponding to such a polynucleotide.

A polynucleotide or polypeptide sequence that is "substantially identical" to a PKD1 polynucleotide of SEQ ID NO:1 or a polypeptide sequence of SEQ ID NO:2 generally is at least 80% or 85%, usually at least about 90%, and particularly at least about 95%, and preferably at least about 99% identical to the nucleotide sequence or amino acid sequence as set forth in SEQ ID NO:1 or SEQ ID NO:2, respectively. It should be recognized, however, that a mutation in a PKD1 gene sequence can result in the expression of a truncated PKD1 polypeptide, or even a complete loss of expression of the PKD1 polypeptide. As such, while a mutant PKD1 polynucleotide is identified as being substantially identical to SEQ ID NO:1, it may not always be possible to make the same comparison with respect to the encoded polypeptides. In one aspect of the invention, a polynucleotide or polypeptide sequence that is substantially identical to SEQ ID NO:1 or 2 will vary at one or more sites having a mutation, for example, a mutation present in a mutant PKD1 polynucleotide as set forth in the preceding paragraph. Sequence identity can be measured using sequence analysis software (e.g., Sequence Analysis Software Package of the Genetics Computer Group, University of Wisconsin Biotechnology Center, 1710 University Avenue, Madison Wis. 53705).

A polynucleotide or oligonucleotide portion thereof of the invention can be useful, for example, as a probe or as a primer for an amplification reaction. Reference to an "oligonucleotide portion" of a mutant PKD1 polynucleotide means a nucleotide sequence of the mutant PKD1 polynucleotide that is less than the full length polynucleotide. Generally, a polynucleotide useful as a probe or a primer contains at least about 10 nucleotides, and usually contains about 15 to 30 nucleotides or more (see, for example, Tables 1 and 2). Polynucleotides can be prepared by any suitable method, including, for example, by restriction enzyme digestion of an appropriate polynucleotide, by direct chemical synthesis using a method such as the phosphotriester method (Narang et al., 1979, Meth. Enzymol., 68:90-99); the phosphodiester method (Brown et al., 1979, Meth. Enzymol., 68:109-151); the diethylphosphoramidite method (Beaucage et al., 1981, Tetrahedron Lett., 22:1859-1862); the triester method (Matteucci et al., 1981, J. Am. Chem. Soc., 103:3185-3191), including by automated synthesis methods; or by a solid support method (see, for example, U.S. Pat. No. 4,458,066). In addition, a polynucleotide or oligonucleotide can be prepared using recombinant DNA methods as disclosed herein or otherwise known in the art.

An oligonucleotide of the invention can include a portion of a mutant PKD1 polynucleotide, including, for example, a sequence substantially identical to that of SEQ ID NO:1, except wherein nucleotide 474 is a T; or wherein nucleotide 487 is an A; or wherein nucleotide 3110 is a C; or wherein nucleotide 8298 is a G; or wherein nucleotide 9164 is a G; or wherein nucleotide 9213 is an A; or wherein nucleotide 9326 is a T; or wherein nucleotide 9367 is a T; or wherein nucleotide 10064 is an A; or wherein nucleotide 10143 is a G; or wherein nucleotide 10234 is a C; or wherein nucleotide 10255 is a T; or wherein the oligonucleotide contains a combination of such substitutions with respect to SEQ ID NO:1. Thus, as disclosed herein, the oligonucleotide can be any length and can encompass one or more of the above mutations.

An oligonucleotide of the invention can selectively hybridize to a mutant PKD1 polynucleotide sequence as disclosed herein. As such, the oligonucleotide does not hybridize substantially, if at all, to a wild type PKD1 polynucleotide (i.e., to SEQ ID NO:1). As used herein, the term "selectively hybridize" refers to the ability of an oligonucleotide (or polynucleotide) probe to hybridize to a selected sequence, but not to a highly related nucleotide sequence. For example, a oligonucleotide of the invention selectively hybridizes to a mutant PKD1 polynucleotide, but not substantially to a corresponding sequence of SEQ ID NO:1. As such, hybridization of the oligonucleotide to SEQ ID NO:1 generally is not above background, or, if some hybridization occurs, is at least about ten-fold less than the amount of hybridization that occurs with respect to the mutant PKD1 polynucleotide.

In addition, the term "hybridize" is used herein to have its commonly understood meaning of two nucleotide sequences that can associate due to shared complementarity. As disclosed herein, a primer of the invention can hybridize to PDK1 gene and may also hybridize to a PDK1 gene homolog, but generally does not substantially hybridize to a nucleotide sequence other than a PKD1 gene or PKD1 gene homolog. Desired hybridization conditions, including those that allow for selective hybridization, can be obtained by varying the stringency of the hybridization conditions, based, in part, on the length of the sequences involved, the relative G:C content, the salt concentration, and the like (see Sambrook et al., supra, 1989). Hybridization conditions that are highly stringent conditions are used for selective hybridization and can be used for hybridization of a primer or primer pair of the invention to a PKD1 gene or PKD1 gene homolog, and include, for example, washing in 6× SSC/0.05% sodium pyrophosphate at about 37° C. (for 14 nucleotide DNA probe), about 48° C. (for 17 nucleotide probe), about 55° C. (for a 20 nucleotide probe), and about 60° C. (for a 23 nucleotide probe). As disclosed herein, polynucleotides that selectively hybridize to a mutant PKD1 polynucleotide provide a means to distinguish the mutant PKD1 polynucleotide from a wild type PKD1 polynucleotide.

A polynucleotide or oligonucleotide of the invention can be used as a probe to screen for a particular PKD1 variant or mutant of interest. In addition, the oligonucleotides of the invention include a PKD1 antisense molecule, which can be useful, for example, in PKD1 polynucleotide regulation and amplification reactions of PKD1 polynucleotide sequences, including mutant PKD1 polynucleotide sequences. Further, such oligonucleotides can be used as part of ribozyme or triple helix sequence for PKD1 gene regulation. Still further, such oligonucleotides can be used as a component of diagnostic method, whereby the level of PKD1 transcript can be determined or the presence of an ADPKD-causing allele can be detected. Further, such oligonucleotides can be used, for example, to screen for and identify PKD1 homologs from other species.

The term "primer" or "PCR primer" refers to an isolated natural or synthetic oligonucleotide that can act as a point of initiation of DNA synthesis when placed under conditions suitable for primer extension. Synthesis of a primer extension product is initiated in the presence of nucleoside triphosphates and a polymerase in an appropriate buffer at a suitable temperature. A primer can comprise a plurality of primers, for example, where there is some ambiguity in the information regarding one or both ends of the target region to be synthesized. For instance, if a nucleic acid sequence is determined from a protein sequence, a primer generated to synthesize nucleic acid sequence encoding the protein sequence can comprise a collection of primers that contains sequences representing all possible codon variations based on the degeneracy of the genetic code. One or more of the primers in this collection will be homologous with the end of the target sequence or a sequence flanking a target sequence. Likewise, if a conserved region shows significant levels of polymorphism in a population, mixtures of primers can be prepared that will amplify adjacent sequences.

During PCR amplification, primer pairs flanking a target sequence of interest are used to amplify the target sequence. A primer pair typically comprises a forward primer, which hybridizes to the 5' end of the target sequence, and a reverse primer, which hybridizes to the 3' end of the target sequence. Except as otherwise provided herein, primers of the present invention are exemplified by those having the sequences set forth as SEQ ID NOS:3 to 51 and 61 to 113 (see Tables 1 and 2). Forward primers are exemplified by SEQ ID NOS:3, 5, 7, 9, 11, 13, 15, 17, 19, 21, 23, 25, 27, 29, 31, 33, 35, 37, 39, 41, 43, 45, 47 and 49; and reverse primers are exemplified by SEQ ID NOS:4, 6, 8, 10, 12, 14, 16, 18, 20, 22, 24, 26, 28, 30, 32, 34, 36, 38, 40, 42, 44, 46, 48, and 50. A primer pair of the invention includes at least one forward primer and at least one reverse primer that allows for generation of an amplification product, which can be a long range PKD1-specific amplification product or a nested amplification product of such an amplification product, including a forward and reverse primer as set forth in SEQ ID NOS:3 to 18 and of SEQ ID NOS:19 to 51 and 61 to 113, provided that the forward primer is 5' (or upstream) of the reverse primer with reference to a target polynucleotide sequence, and that the primers are in sufficient proximity such that an amplification product can be generated.

Nucleic acid sequences that encode a fusion protein can be produced and can be operatively linked to expression control sequences. Such fusion proteins and compositions are useful in the development of antibodies or to generate and purify peptides and polypeptides of interest. As used herein, the term "operatively linked" refers to a juxtaposition, wherein the components so described are in a relationship permitting them to function in their intended manner. For example, an expression control sequence operatively linked to a coding sequence is ligated such that expression of the coding sequence is achieved under conditions compatible with the expression control sequences, whereas two operatively linked coding sequences can be ligated such that they are in the same reading frame and, therefore, encode a fusion protein.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the mRNA, and STOP codons. Control sequences include, at a minimum, components whose presence can influence expression, and can also include additional components whose presence is advantageous, for example, leader sequences and fusion partner sequences. Expression control sequences can include a promoter.

A polynucleotide of the invention can comprise a portion of a recombinant nucleic acid molecule, which, for example, can encode a fusion protein. The polynucleotide, or recombinant nucleic acid molecule, can be inserted into a vector, which can be an expression vector, and can be derived from a plasmid, a virus or the like. The expression vector generally contains an origin of replication, a promoter, and one or more genes that allow phenotypic selection of transformed cells containing the vector. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988); baculovirus-derived vectors for expression in insect cells; and the like.

The choice of a vector will also depend on the size of the polynucleotide sequence and the host cell to be employed in the methods of the invention. Thus, the vector used in the invention can be plasmids, phages, cosmids, phagemids, viruses (e.g. retroviruses, parainfluenzavirus, herpesviruses, reoviruses, paramyxoviruses, and the like), or selected portions thereof (e.g., coat protein, spike glycoprotein, capsid protein). For example, cosmids and phagemids are typically used where the specific nucleic acid sequence to be analyzed or modified is large because these vectors are able to stably propagate large polynucleotides. Cosmids and phagemids are particularly suited for the expression or manipulation of the PKD1 polynucleotide of SEQ ID NO:1 or a mutant PKD1 polynucleotide.

In yeast, a number of vectors containing constitutive or inducible promoters can be used (see Ausubel et al., supra, 1989; Grant et al., Meth. Enzymol. 153:516-544, 1987; Glover, DNA Cloning, Vol. 11, IRL Press, Washington D.C., Ch. 3, 1986; and Bitter, Meth. Enzymol. 152:673-684, 1987; and The Molecular Biology of the Yeast Saccharomyces, Eds. Strathern et al., Cold Spring Harbor Press, Vols. I and II, 1982). A constitutive yeast promoter such as ADH or LEU2 or an inducible promoter such as GAL can be used ("Cloning in Yeast," Ch. 3, Rothstein, In "DNA Cloning" Vol. 11, A Practical Approach, ed. Clover, IRL Press, 1986). Alternatively, vectors can be used which promote integration of foreign DNA sequences into the yeast chromosome. The construction of expression vectors and the expression of genes in transfected cells involves the use of molecular cloning techniques also well known in the art (see Sambrook et al., supra, 1989;

Ausubel et al., supra, 1989). These methods include in vitro recombinant DNA techniques, synthetic techniques and in vivo recombination/genetic recombination.

A polynucleotide or oligonucleotide can be contained in a vector and can be introduced into a cell by transformation or transfection of the cell. By "transformation" or "transfection" is meant a permanent (stable) or transient genetic change induced in a cell following incorporation of new DNA (i.e., DNA exogenous to the cell). Where the cell is a mammalian cell, a permanent genetic change is generally achieved by introduction of the DNA into the genome of the cell.

A transformed cell or host cell can be any prokaryotic or eukaryotic cell into which (or into an ancestor of which) has been introduced, by means of recombinant DNA techniques, a polynucleotide sequence of the invention or fragment thereof. Transformation of a host cell can be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art, or using $MgCl_2$ or RbCl. Transformation can also be performed after forming a protoplast of the host cell or by electroporation.

When the host is a eukaryote, such methods of transfection include the use of calcium phosphate co-precipitates, conventional mechanical procedures such as microinjection, electroporation, insertion of a plasmid encased in liposomes, or the use of virus vectors, or other methods known in the art. One method uses a eukaryotic viral vector, such as simian virus 40 (SV40) or bovine papillomavirus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell can be a yeast cell (e.g., *Saccharomyces cerevisiae*), or can be a mammalian cell, including a human cell.

A variety of host-expression vector systems can be utilized to express a PKD1 polynucleotide sequence such as SEQ ID NO:1, a coding sequence of SEQ ID NO:1 or a mutant PKD1 polynucleotide. Such host-expression systems represent vehicles by which the nucleotide sequences of interest can be produced and subsequently purified, and also represent cells that, when transformed or transfected with the appropriate nucleotide coding sequences, can express a PKD1 protein, including a PKD1 variant or mutant polypeptide or peptide portion thereof in situ. Such cells include, but are not limited to, microorganisms such as bacteria (e.g., *E. coli, B. subtilis*) transformed with recombinant bacteriophage DNA, plasmid DNA or cosmid DNA expression vectors containing a PKD1 polynucleotide, or oligonucleotide portion thereof (wild type, variant or other mutant); yeast (e.g., *Saccharomyces, Pichia*) transformed with recombinant yeast expression vectors containing a PKD1 polynucleotide, or oligonucleotide portions thereof (wild type, variant or other PKD1 mutant); insect cell systems infected with recombinant virus expression vectors (e.g., baculovirus) containing a PKD1 polynucleotide, or oligonucleotide portion thereof (wild type, PKD1 variant or other mutant); plant cell systems infected with recombinant virus expression vectors (e.g., cauliflower mosaic virus or tobacco mosaic virus) or transformed with recombinant plasmid expression vectors (e.g., Ti plasmid) containing a mutant PKD1 polynucleotide, or oligonucleotide portion thereof; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the PKD1 protein (wild type, variant or other PKD1 mutant) being expressed. For example, when a large quantity of such a protein is to be produced, for the generation of antibodies, which can be used to identify or diagnose PKD1-associated diseases or disorders, or to screen peptide libraries, vectors that direct the expression of high levels of fusion protein products that are readily purified can be desirable. Such vectors include, but are not limited to, the *E. coli* expression vector pUR278 (Ruther et al., 1983, EMBO J. 2:1791), in which a PKD1 polynucleotide, or oligonucleotide portion thereof (wild type, variant or other mutant) can be ligated individually into the vector in frame with the lac Z coding region so that a fusion protein is produced; pIN vectors (Inouye and Inouye, Nucl. Acids Res. 13:3101-3109, 1985; Van Heeke and Schuster, J. Biol. Chem. 264:5503-5509, 1989); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned PKD1 protein, variant or mutant can be released from the GST moiety.

In an insect system, *Autographa californica* nuclear polyhedrosis virus (AcNPV) is used as a vector to express foreign genes. The virus grows in *Spodoptera frugiperda* cells. A PKD1 polynucleotide, or oligonucleotide portion thereof can be cloned individually into non-essential regions (for example the polyhedrin gene) of the virus and placed under control of an AcNPV promoter (for example the polyhedrin promoter). Successful insertion of a PKD1 polynucleotide, or oligonucleotide portion thereof will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (see Smith et al., 1983, J. Virol. 46:584; U.S. Pat. No. 4,215,051).

In mammalian host cells, a number of viral-based expression systems can be utilized. In cases where an adenovirus is used as an expression vector, a PKD1 polynucleotide, or oligonucleotide portion thereof, can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome such as the E1 or E3 region results in a recombinant virus that is viable and capable of expressing a PKD1 protein (e.g., wild-type, variants or mutants thereof) in infected hosts (Logan and Shenk, Proc. Natl. Acad. Sci., USA 81:3655-3659, 1984). Specific initiation signals can also be required for efficient translation of an inserted PKD1 sequence. These signals include the ATG initiation codon and adjacent sequences. Where an entire PKD1 polynucleotide, including its own initiation codon and adjacent sequences, is inserted into the appropriate expression vector, no additional translational control signals can be needed. However, where only a portion of a PKD1 sequence is inserted, exogenous translational control signals, including, for example, an ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, and the like (see Bittner et al., Meth. Enzymol. 153:516-544, 1987).

In addition, a host cell strain can be chosen which modulates the expression of the inserted sequences, or modifies and processes the expressed polypeptide in a specific fashion. Such modifications (e.g, glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein being expressed. To this end, eukaryotic host cells which possess the cellular machinery for proper processing of the primary transcript, glycosylation, and phosphorylation of the polypeptide can be used. Such mammalian host cells include, but are not limited to, CHO, VERO, BHK, HeLa, COS, MDCK, 293, 3T3, WI38, and the like.

For long term, high yield production of recombinant proteins, stable expression is preferred. For example, cell lines that stably express a PKD1 protein, including wild-type, variants or mutants of PKD1, can be engineered. Rather than using expression vectors which contain viral origins of replication, host cells can be transformed with DNA controlled by appropriate expression control elements (e.g., promoter and/or enhancer sequences, transcription terminators, polyadenylation sites, and the like), and a selectable marker. Following the introduction of the foreign DNA, engineered cells can be grown for 1-2 days in an enriched media, then switched to selective media. The selectable marker in the recombinant plasmid confers resistance to the selection and allows cells to stably integrate the plasmid into their chromosomes and grow to form foci, which can be cloned and expanded into cell lines. This method can advantageously be used to engineer cell lines that express a PKD1 variant or mutant polypeptide. Such engineered cell lines can be particularly useful in screening and evaluation of compounds that affect the endogenous activity of a variant or mutant PKD1 polypeptide. Such engineered cell lines also can be useful to discriminate between factors that have specific vs. non-specific effects. In particular, mutant cell lines should lack key functions, and various mutations can be used to identify key functional domains using in vivo assays.

A number of selection systems can be used, including but not limited to the herpes simplex virus thymidine kinase (Wigler et al., Cell 11:223, 1977), hypoxanthine-guanine phosphoribosyltransferase (Szybalska and Szybalski, Proc. Natl. Acad. Sci. USA 48:2026, 1962), and adenine phosphoribosyltransferase (Lowy et al., Cell 22:817, 1980) genes can be employed in tk⁻, hgprt⁻ or aprt⁻ cells, respectively. Also, antimetabolite resistance can be used as the basis of selection for dhfr, which confers resistance to methotrexate (Wigler et al., Proc. Natl. Acad. Sci. USA 77:3567, 1980; O'Hare et al., Proc. Natl. Acad. Sci. USA 78:1527, 1981); gpt, which confers resistance to mycophenolic acid Mulligan and Berg, Proc. Natl. Acad. Sci. USA 78:2072, 1981); neo, which confers resistance to the aminoglycoside G-418 (Colberre-Garapin et al., J. Mol. Biol. 150:1, 1981); and hygro, which confers resistance to hygromycin (Santerre et al., Gene 30:147, 1984) genes. Accordingly, the invention provides a vector that contains a mutant PKD1 polynucleotide, or oligonucleotide portion thereof, or one or more primers or their complements, including an expression vector that contains any of the foregoing sequences operatively associated with a regulatory element that directs the expression of a coding sequence or primer; and also provides a host cell that contains any of the foregoing sequences, alone or operatively associated with a regulatory element, which can directs expression of a polypeptide encoded the polynucleotide, as appropriate.

In addition to mutant PKD1 polynucleotide sequences disclosed herein, homologs of mutant PKD1 polynucleotide of the invention, including a non-human species, can be identified and isolated by molecular biological techniques well known in the art. Further, mutant PKD1 alleles and additional normal alleles of the human PKD1 polynucleotide, can be identified using the methods of the invention. Still further, there can exist genes at other genetic loci within the human genome that encode proteins having extensive homology to one or more domains of the PKD1 polypeptide (SEQ ID NO:2). Such genes can also be identified including associated variants and mutants by the methods of the invention.

A homolog of a mutant PKD1 polynucleotide sequence can be isolated by performing a polymerase chain reaction (PCR; see U.S. Pat. No. 4,683,202, which is incorporated herein by reference) using two oligonucleotide primers, which can be selected, for example, from among SEQ ID NOS:3 to 51, preferably from among SEQ ID NOS: 3 to 18, or can be degenerate primer pools designed on the basis of the amino acid sequences of a PKD1 polypeptide such as that set forth in SEQ ID NO:2 or a mutant thereof as disclosed herein. The template for the reaction can be cDNA obtained by reverse transcription of mRNA prepared from human or non-human cell lines or tissue known to express a PKD1 allele or PKD1 homologue. The PCR product can be subcloned and sequenced or manipulated in any number of ways (e.g., further manipulated by nested PCR) to insure that the amplified sequences represent the sequences of a PKD1 or a PKD mutant polynucleotide sequence. The PCR fragment can then be used to isolate a full length PKD1 cDNA clone (including clones containing a mutant PKD1 polynucleotide sequence) by labeling the amplified fragment and screening a nucleic acid library (e.g., a bacteriophage cDNA library). Alternatively, the labeled fragment can be used to screen a genomic library (for review of cloning strategies, see, for example, Sambrook et al., supra, 1989; Ausubel et al., supra, 1989).

The present invention also provides a purified mutant PKD1 polypeptide, or a peptide portion thereof. As disclosed herein, a mutant PKD1 polypeptide has an amino acid sequence substantially identical to SEQ ID NO:2, and includes a mutation resulting in the deletion, addition (insertion), or substitution of an amino acid of SEQ ID NO:2, or is truncated with respect to SEQ ID NO:2. Examples of such mutations include, with respect to SEQ ID NO:2, an A88V, W967R, G1166S; V1956E; R1995H; R2408C; D2604N; L2696R, R2985G, R3039C, V3285I, or H331 IR mutation, an addition of a Gly residue between amino acid residues 2441 and 2442 of SEQ ID NO:2 due to an insertion, or a truncated PKD1 polypeptide terminates with amino acid 3000 of SEQ ID NO:2 due to the presence of a STOP codon at the position in SEQ ID NO:1 that would otherwise encode amino acid 3001; as well as mutant PKD1 polypeptides having a combination of such mutations (see Table 4).

A mutant PKD1 polypeptide or peptide portion thereof can contain one or more of the exemplified mutations. As used herein, reference to a peptide portion of SEQ ID NO:2 or of a mutant PKD1 polypeptide refers to a contiguous amino acid sequence of SEQ ID NO:2 or of SEQ ID NO:2 including a mutation as disclosed herein, respectively, that contains fewer amino acids than full length wild type PKD1 polypeptide.

Generally, a peptide portion of a PKD1 polypeptide or a mutant PKD1 polypeptide contains at least about five amino acids (or amino acid derivatives or modified amino acids), each linked by a peptide bond or a modified form thereof, usually contains at least about eight amino acids, particularly contains about ten amino acids, and can contain twenty or thirty or more amino acids of SEQ ID NO:2. In particular, where the peptide is a peptide portion of a mutant PKD1 polypeptide, the peptide includes a mutant amino acid with respect to SEQ ID NO:2.

The mutant PKD1 polypeptides and peptide fragments thereof of the invention include a PKD1 polypeptide or peptide having a sequence substantially identical to that set forth in SEQ ID NO:2, and having one or a combination of the following mutations: A88V, W967R, L2696R, R2985G, R3039C, V3285I, or H3311 R, or a mutation resulting in termination of the mutant PKD1 polypeptide at amino acid 3000 (with respect to SEQ ID NO:2) due to the presence of a STOP codon at the position that otherwise would encode amino acid 3001. The wild type PKD1 polypeptide (SEQ ID NO:2) contains 4303 amino acid residues and has a predicted molecular mass of approximately 467 kilodaltons (kDa). Further encompassed by the present invention are mutant PKD1 polypeptides that are truncated with respect to SEQ ID NO:2, for example, a mutation of SEQ ID NO:1 resulting in a G9213A, which results in premature termination of the encoded PKD1 polypeptide (see Example 2). Such truncated products can be associated with PKD1-associated disorders such as ADPKD (see, also, Table 4).

PKD1 polypeptides that are functionally equivalent to a wild type PKD1 polypeptide, including variant PKD1 polypeptides, which can contain a deletion, insertion or substitution of one or more amino acid residues with respect to SEQ ID NO:2, but that nevertheless result in a phenotype that is indistinguishable from that conferred by SEQ ID NO:2, are encompassed within the present invention. Such amino acid substitutions, for example, generally result in similarity in polarity, charge, solubility, hydrophobicity, hydrophilicity, amphipatic nature or the like of the residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine, glycine, alanine, asparagine, glutamine, serine, threonine, phenylalanine and tyrosine. In many cases, however, a nucleotide substitution can be silent, resulting in no change in the encoded PKD1 polypeptide (see Example 2). Such variant PKD1 polynucleotides are exemplified by those encoded by the variant PKD1 polynucleotide sequences substantially identical to SEQ ID NO:1 (SEQ ID NO:2), but containing (encoding) G487A (A92A), C9367T (G3052G), T10234C (L3341L), and G10255T (R3348R) as shown in Table 3 (see, also, Example 2), and by C9494T (L3095L).

Mutant PKD1 polypeptides and peptide portions thereof that are substantially identical to the PKD1 polypeptide SEQ ID NO:2 or peptide portions thereof, which cause ADPKD symptoms, are encompassed within the scope of the invention. Such mutant PKD1 polypeptides and peptide portions thereof can include dominant mutant PKD1 polypeptides, or PKD1 related polypeptides functionally equivalent to such mutant PKD1 polypeptides. Examples of mutant PKD1 polypeptide sequences include a polypeptide sequences substantially identical to SEQ ID NO:2 having one or more amino acid substitutions such as A88V, W967R, L2696R, R2985G, R3039C, V3285I, or H331 IR, or truncated after amino acid 3000. A peptide portion of a mutant PKD1 polypeptide can be 3, 6, 9, 12, 20, 50, 100 or more amino acid residues in length, and includes at least one of the mutations identified above.

A PKD1 wild type or mutant polypeptide, or peptide portions thereof, can be purified from natural sources, as discussed below; can be chemically synthesized; or can be recombinantly expressed. For example, one skilled in the art can synthesize peptide fragments corresponding to a mutated portion of the PKD1 polypeptide as set forth in SEQ ID NO:2 (e.g., including residue 3110) and use the synthesized peptide fragment to generate polyclonal and monoclonal antibodies. Synthetic polypeptides or peptides can be prepared by chemical synthesis, for example, solid-phase chemical peptide synthesis methods, which are well known (see, for example, Merrifield, J. Am. Chem. Soc., 85:2149-2154,1963; Stewart and Young, Solid Phase Peptide Synthesis, 2d ed., Pierce Chemical Co., Rockford Ill., pages 11-12), and have been employed in commercially available laboratory peptide design and synthesis kits (Cambridge Research Biochemicals). Such commercially available laboratory kits have generally utilized the teachings of Geysen et al., Proc. Natl. Acad. Sci., USA, 81:3998 (1984) and provide for synthesizing peptides upon the tips of a multitude of rods or pins, each of which is connected to a single plate. When such a system is utilized, a plate of rods or pins is inverted and inserted into a second plate of corresponding wells or reservoirs, which contain solutions for attaching or anchoring an appropriate amino acid to the tips of the pins or rods. By repeating such a process step, i.e., inverting and inserting the tips of the rods or pins into appropriate solutions, amino acids are built into desired peptides.

A number of available FMOC peptide synthesis systems are available. For example, assembly of a polypeptide or fragment can be carried out on a solid support using an Applied Biosystems, Inc., Model 431A automated peptide synthesizer. Such equipment provides ready access to the peptides of the invention, either by direct synthesis or by synthesis of a series of fragments that can be coupled using other known techniques. Accordingly, methods for the chemical synthesis of polypeptides and peptides are well-known to those of ordinary skill in the art, e.g., peptides can be synthesized by solid phase techniques, cleaved from the resin and purified by preparative high performance liquid chromatography (see, e.g., Creighton, 1983, Proteins: Structures and Molecular Principles, W. H. Freeman & Co., N.Y., pp. 50-60). The composition of the synthetic peptides can be confirmed by amino acid analysis or sequencing; e.g., using the Edman degradation procedure (see e.g., Creighton, 1983, supra at pp. 34-49). Thus, fragments of the PKD1 polypeptide, variant, or mutant can be chemically synthesized. Peptides can then be used, for example, to generate antibodies useful in the detection of PKD1 variants and mutants, as well as the diagnosis of PKD1-associated disorder (e.g., ADPKD).

A PKD1 polypeptide or peptide, including variants or mutants of the invention, can be substantially purified from natural sources (e.g., purified from cells) using protein separation techniques, well known in the art. Such methods can separate the PKD1 polypeptide away from at least about 90% (on a weight basis), and from at least about 99% of other proteins, glycoproteins, and other macromolecules normally found in such natural sources. Such purification techniques can include, but are not limited to ammonium sulfate precipitation, molecular sieve chromatography, and/or ion exchange chromatography. Alternatively, or additionally, the PKD1 polypeptide, variant, or mutant can be purified by immunoaffinity chromatography using an inunuoabsorbent column to which an antibody is immobilized that is capable of specifically binding the PKD1 polypeptide, variant, or mutant. Such an antibody can be monoclonal or polyclonal in origin. For example, an antibody that specifically binds to a mutant PKD1 polypeptide does not bind to a wild-type PKD1 polypeptide or peptide thereof. If the PKD1 polypeptide is glycosylated, the glycosylation pattern can be utilized as part of a purification scheme via, for example, lectin chromatography.

The cellular sources from which the PKD1 polypeptide, variant, or mutants thereof can be purified include, for example, those cells that are shown by northern and/or western blot analysis to express a PKD1 polynucleotide, variant, or mutant sequence. Preferably, such cellular sources are renal cells including, for example, renal tubular epithelial cells, as well as biliary duct cells, skeletal muscle cells, lung alveolar epithelial cell, placental cells, fibroblasts, lymphoblasts, intestinal epithelial cells, and endothelial cells. Other sources include biological fluids, fractionated cells such as organelle preparations, or tissues obtained from a subject. Examples of biological fluids of use with the invention are blood, serum, plasma, urine, mucous, and saliva. Tissue or cell samples can also be used with the invention. The samples can be obtained by many methods such as cellular aspiration, or by surgical removal of a biopsy sample.

PKD1 polypeptides, variants, or mutants of the invention can be secreted out of the cell. Such extracellular forms of the PKD1 polypeptide or mutants thereof can preferably be purified from whole tissue rather than cells, utilizing any of the techniques described above. PKD1 expressing cells such as those described above also can be grown in cell culture, under conditions well known to those of skill in the art. PKD1 polypeptide or mutants thereof can then be purified from the cell media using any of the techniques discussed above.

A PKD1 polypeptide, variant, or mutant can additionally be produced by recombinant DNA technology using the PKD1 nucleotide sequences, variants and mutants described above coupled with techniques well known in the art. Alternatively, RNA capable of encoding PKD1 polypeptides, or peptide fragments thereof, can be chemically synthesized using, for example, automated or semi-automated synthesizers (see, for example, "Oligonucleotide Synthesis", 1984, Gait, ed., IRL Press, Oxford, which is incorporated herein by reference).

When used as a component in the assay systems described herein, the mutant PKD1 polypeptide or peptide can be labeled, either directly or indirectly, to facilitate detection of a complex formed between the PKD1 polypeptide and an antibody or nucleic acid sequence, for example. Any of a variety of suitable labeling systems can be used including, but not limited to, radioisotopes such as $^{125}$I, enzyme labeling systems such as biotin-avidin or horseradish peroxidase, which generates a detectable calorimetric signal or light when exposed to substrate, and fluorescent labels.

The present invention also provides antibodies that specifically bind a PKD1 mutant or PKD1 variant, except that, if desired, an antibody of the invention can exclude an antibody as described in U.S. Pat. No. 5,891,628, which is incorporated herein by reference, or an antibody that that specifically binds a PKD1 mutant as described in U.S. Pat. No. 5,891,628. Antibodies that specifically bind a mutant PKD1 polypeptide are useful as diagnostic or therapeutic reagents and, therefore, can be used, for example, in a diagnostic assay for identifying a subject having or at risk of having ADPKD, and are particularly convenient when provided as a kit.

As used herein, the term "specifically binds," when used in reference to an antibody and an antigen or epitopic portion thereof, means that the antibody and the antigen (or epitope) have a dissociation constant of at least about $1\times10^{-7}$, generally at least about $1\times10^{-8}$, usually at least about $1\times10^{-9}$, and particularly at least about $1\times10^{-10}$ or less. Methods for identifying and selecting an antibody having a desired specificity are well known and routine in the art (see, for example, Harlow and Lane, "Antibodies: A Laboratory Manual" (Cold Spring Harbor Pub. 1988), which is incorporated herein by reference.

Methods for producing antibodies that can specifically bind one or more PKD1 polypeptide epitopes, particularly epitopes unique to a mutant PKD1 polypeptide, are disclosed herein or otherwise well known and routine in the art. Such antibodies can be polyclonal antibodies or monoclonal antibodies (mAbs), and can be humanized or chimeric antibodies, single chain antibodies, anti-idiotypic antibodies, and epitope-binding fragments of any of the above, including, for example, Fab fragments, F(ab')$_2$ fragments or fragments produced by a Fab expression library. Such antibodies can be used, for example, in the detection of PKD1 polypeptides, or mutant PKD1 polypeptides, including variant PKD1 polypeptides, which can be in a biological sample, or can be used for the inhibition of abnormal PKD1 activity. Thus, the antibodies can be utilized as part of ADPKD treatment methods, as well as in diagnostic methods, for example, to detect the presence or amount of a PKD1 polypeptide.

For the production of antibodies that bind to PKD1, including a PKD1 variant or PKD1 mutant, various host animals can be immunized by injection with a PKD1 polypeptide, mutant polypeptide, variant, or a portion thereof. Such host animals can include but are not limited to, rabbits, mice, and rats. Various adjuvants can be used to increase the immunological response, depending on the host species, including, but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (*Bacillus* Calmette-Guerin) or *Corynebacterium parvum*.

Antibodies that bind to a mutant PKD1 polypeptide, or peptide portion thereof, of the invention can be prepared using an intact polypeptide or fragments containing small peptides of interest as the immunizing antigen. The polypeptide or a peptide used to immunize an animal can be derived from translated cDNA or chemical synthesis, and can be conjugated to a carrier protein, if desired. Such commonly used carriers that can be chemically coupled to the peptide include keyhole limpet hemocyanin, thyroglobulin, bovine serum albumin, tetanus toxoid and others as described above or otherwise known in the art. The coupled polypeptide or peptide is then used to immunize the animal and antiserum can be collected. If desired, polyclonal or monoclonal antibodies can be purified, for example, by binding to and elution from a matrix to which the polypeptide or a peptide to which the antibodies were raised is bound. Any of various techniques commonly used in immunology for purification and/or concentration of polyclonal antibodies, as well as monoclonal antibodies, can be used (see for example, Coligan, et al., Unit 9, Current Protocols in Immunology, Wiley Interscience, 1991, which is incorporated herein by reference).

Anti-idiotype technology can be used to produce monoclonal antibodies that mimic an epitope. For example, an anti-idiotypic monoclonal antibody made to a first monoclonal antibody will have a binding domain in the hypervariable region that is the image of the epitope bound by the first monoclonal antibody. Antibodies of the invention include polyclonal antibodies, monoclonal antibodies, and fragments of polyclonal and monoclonal antibodies that specifically bind to a mutant PKD1 polypeptide or peptide portion thereof.

The preparation of polyclonal antibodies is well known to those skilled in the art (see, for example, Green et al., Production of Polyclonal Antisera, in Immunochemical Protocols (Manson, ed.), pages 1-5 (Humana Press 1992); Coligan et al., Production of Polyclonal Antisera in Rabbits, Rats, Mice and Hamsters, in Current Protocols in Immunology, section 2.4.1 (1992), which are incorporated herein by reference). The preparation of monoclonal antibodies likewise is conventional (see, for example, Kohler and Milstein, Nature, 256:495, 1975, which is incorporated herein by reference; see, also Coligan et al., supra, sections 2.5.1-2.6.7; and Harlow et al., supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography (see Coligan et al., sections 2.7.1-2.7.12 and sections 2.9.1-2.9.3; Barnes et al., Purification of Immunoglobulin G (IgG), in Methods in Molecular Biology, Vol. 10, pages 79-104 (Humana Press 1992)). Methods of in vitro and in vivo multiplication of hybridoma cells expressing monoclonal antibodies is well-known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth-sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into manunals histocompatible with the parent cells, e.g., syngeneic mice, to cause growth of antibody-producing tumors. Optionally, the animals are primed with a hydrocarbon, especially oils such as pristane tetramethylpentadecane prior to injection. After one to three weeks, the desired monoclonal antibody is recovered from the body fluid of the animal.

Therapeutic applications for antibodies disclosed herein are also part of the present invention. For example, antibodies of the present invention can be derived from subhuman primate antibodies. General techniques for raising therapeutically useful antibodies in baboons can be found, for example, in Goldenberg et al., International Application Publication No. WO 91/11465, 1991; Losman et al., Int. J. Cancer, 46:310, 1990, which are incorporated herein by reference.

An anti-PKD1 antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Natl. Acad. Sci. USA 86:3833, 1989, which is incorporated herein by reference. Techniques for producing humanized monoclonal antibodies are described, for example, by Jones et al., Nature, 321:522, 1986; Riechmann et al., Nature 332:323, 1988; Verhoeyen et al., Science 239:1534, 1988; Carter et al., Proc. Natl. Acad. Sci. USA, 89:4285, 1992; Sandhu, Crit. Rev. Biotech. 12:437, 1992; and Singer et al., J. Immunol. 150: 2844, 1993, which are incorporated herein by reference.

Antibodies of the invention also can be derived from human antibody fragments isolated from a combinatorial immunoglobulin library (see, for example, Barbas et al., Methods: A Companion to Methods in Enzymology, Vol. 2, page 119, 1991; Winter et al., Ann. Rev. Immunol. 12:433, 1994, which are incorporated herein by reference). Cloning and expression vectors that are useful for producing a human immunoglobulin phage library can be obtained, for example, from Stratagene (La Jolla Calif.).

In addition, antibodies of the present invention can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet., 7:13 (1994); Lonberg et al., Nature, 368:856 (1994); Taylor et al., Int. Immunol., 6:579 (1994), each of which is incorporated herein by reference.

Antibody fragments of the invention can be prepared by proteolytic hydrolysis of an antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331, 647, and references contained therein, each of which in incorporated herein by reference (see, also, Nisonhoff et al., Arch. Biochem. Biophys, 89:230, 1960; Porter, Biochem. J. 73:119, 1959; Edelman et al., Meth. Enzymol. 1:422, 1967; and Coligan et al., at sections 2.8.1-2.8.10 and 2.10.1-2.10.4). Other methods of cleaving antibodies, such as separation of heavy chains to form monovalent light-heavy chain fragments, further cleavage of fragments, or other enzymatic, chemical, or genetic techniques can also be used, provided the fragments bind to the antigen that is recognized by the intact antibody.

Fv fragments comprise an association of $V_H$ and $V_L$ chains, for example, which can be noncovalent (see Inbar et al., Proc. Natl. Acad. Sci. USA 69:2659, 1972). The variable chains also can be linked by an intermolecular disulfide bond, can be crosslinked by a chemical such as glutaraldehyde (Sandhu, supra, 1992), or F$_v$ fragments comprising $V_H$ and $V_L$ chains can be connected by a peptide linker. These single chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Meth. Enzymol., 2:97, 1991; Bird et al., Science 242:423, 1988; Ladner et al., U.S. Pat. No. 4,946,778; Pack et al., BioTechnology 11:1271, 1993; and Sandhu, supra, 1992).

Another form of an antibody fragment is a peptide coding for a single complementarity determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., Methods: A Companion to Meth. Enzymol., 2:106, 1991).

A variety of methods can be employed utilizing reagents such as a mutant PKD1 polynucleotide, or oligonucleotide portion thereof and antibodies directed against a mutant PKD1 polypeptide or peptide. Specifically, such reagents can be used for the detection of the presence of PKD1 mutations, e.g., molecules present in diseased tissue but absent from, or present in greatly reduced levels compared or relative to the corresponding non-diseased tissue.

The methods described herein can be performed, for example, by utilizing pre-packaged kits, which can be diagnostic kits, comprising at least one specific oligonucleotide portion of a PKD1 gene or mutant PKD1 polynucleotide, a primer pair, or an anti-PKD1 antibody reagent as disclosed herein, which can be conveniently used, for example, in a clinical setting to diagnose subjects exhibiting PKD1 abnormalities or to detect PKD1-associated disorders, including ADPKD. Any tissue in which a PKD1 polynucleotide is expressed can be utilized in a diagnostic method of the invention.

Nucleic acids from a tissue to be analyzed can be isolated using procedures that are well known in the art, or a diagnostic procedures can be performed directly on a tissue section (fixed or frozen), which can be obtained from a subject by biopsy or resection, without further purification. Oligonucleotide sequences of the invention can be used as probes or primers for such in situ procedures (Nuovo, 1992, PCR in situ hybridization: protocols and applications, Raven Press, N.Y.). For example, oligonucleotide probes useful in the diagnostic methods of the invention include nucleotide sequences having at least 10 contiguous nucleotides and having a sequence substantially identical to a portion of SEQ ID NO:1, and including nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; nucleotide 10255, wherein nucleotide 10255 is a T, or a combination thereof. Primers useful in the present invention include those set forth in SEQ ID NOS:3 to 18 and SEQ ID NOS: 19 to 51 and 61 to 112. Such primers flank and can be used to amplify sequences containing one or more mutated nucleotides of a mutant PKD1 polynucleotide.

PKD1 polynucleotide sequences, either RNA or DNA, can be used in hybridization or amplification assays of biological samples to detect abnormalities of PKD1 expression; e.g., Southern or northern blot analysis, single stranded conformational polymorphism (SSCP) analysis including in situ hybridization assays, or polymerase chain reaction analyses, including detecting abnormalities by a methods such as denaturing high performance liquid chromatography (DHPLC; also referred to as temperature-modulated heteroduplex chromatography) or conformation sensitive gel electrophoresis (CSGE), both of which are readily adaptable to high throughput analysis (see, for example, Kristensen et al., BioTechniques 30:318-332, 2001; Leung et al., BioTechniques 30:334-340, 2001, which are incorporated herein by reference). Such analyses can reveal quantitative abnormalities in the expression pattern of the PKD1 polynucleotide, and, if the PKD1 mutation is, for example, an extensive deletion, or the result of a chromosomal rearrangement, can reveal more qualitative aspects of the PKD1 abnormality.

Diagnostic methods for detecting a mutant PKD1 polynucleotide can involve, for example, contacting and incubating nucleic acids derived from a tissue sample being analyzed, with one or more labeled oligonucleotide probes of the invention or with a primer or primer pair of the invention, under conditions favorable for the specific annealing of these reagents to their complementary sequences within the target molecule. After incubation, non-annealed oligonucleotides are removed, and hybridization of the probe or primer, if any, to a nucleic acid from the target tissue is detected. Using such a detection scheme, the target tissue nucleic acid can be immobilized, for example, to a solid support such as a membrane, or a plastic surface such as that on a microtiter plate or polystyrene beads. In this case, after incubation, non-annealed, labeled nucleic acid reagents are easily removed. Detection of the remaining, annealed, labeled nucleic acid reagents is accomplished using standard techniques well known to those in the art.

Oligonucleotide probes or primers of the invention also can be associated with a solid matrix such as a chip in an array, thus providing a means for high throughput methods of analysis. Microfabricated arrays of large numbers of oligonucleotide probes (DNA chips) are useful for a wide variety of applications. Accordingly, methods of diagnosing or detecting a PKD1 variant or mutant can be implemented using a DNA chip for analysis of a PKD1 polynucleotide and detection of mutations therein. A methodology for large scale analysis on DNA chips is described by Hacia et al. (Nature Genet. 14:441-447, 1996; U.S. Pat. No. 6,027,880, which are incorporated herein by reference; see, also, Kristensen et al., supra, 2001). As described in Hacia et al., high density arrays of over 96,000 oligonucleotides, each about 20 nucleotides in length, are immobilized to a single glass or silicon chip using light directed chemical synthesis. Contingent on the number and design of the oligonucleotide probe, potentially every base in a sequence can be examined for alterations.

Polynucleotides or oligonucleotides applied to a chip can contain sequence variations, which can be used to identify mutations that are not yet known to occur in the population, or they can only those mutations that are known to occur, including those disclosed herein (see Example 2). Examples of oligonucleotides that can be applied to the chip include oligonucleotides containing at least 10 contiguous nucleotides and having a sequence substantially identical to a portion of SEQ ID NO:1, and including nucleotide 474, wherein nucleotide 474 is a T; nucleotide 487, wherein nucleotide 487 is an A; nucleotide 3110, wherein nucleotide 3110 is a C; a position corresponding to nucleotide 3336, wherein nucleotide 3336 is deleted; nucleotide 3707, wherein nucleotide 3707 is an A; nucleotide 4168, wherein nucleotide 4168 is a T; nucleotide 4885, wherein nucleotide 4885 is an A; nucleotide 5168, wherein nucleotide 5168 is a T; nucleotide 6058, wherein nucleotide 6058 is a T; nucleotide 6078, wherein nucleotide 6078 is an A; nucleotide 6089, wherein nucleotide 6089 is a T; nucleotide 6195, wherein nucleotide 6195 is an A; nucleotide 6326, wherein nucleotide 6326 is a T; a position corresponding to nucleotides 7205 to 7211, wherein nucleotides 7205 to 7211 are deleted; nucleotide 7376, wherein nucleotide 7376 is a C; a nucleotide sequence corresponding to nucleotides 7535 to 7536, wherein a GCG nucleotide sequence is inserted between nucleotides 7535 and 7536; nucleotide 7415, wherein nucleotide 7415 is a T; nucleotide 7433, wherein nucleotide 7433 is a T; nucleotide 7696, wherein nucleotide 7696 is a T; nucleotide 7883, wherein nucleotide 7883 is a T; nucleotide 8021, wherein nucleotide 8021 is an A; a nucleotide sequence corresponding to nucleotide 8159 to 8160, wherein nucleotides 8159 to 8160 are deleted; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; nucleotide 10255, wherein nucleotide 10255 is a T; or a combination thereof.

Prior to hybridization with oligonucleotide probes on the chip, the test sample is isolated, amplified and labeled (e.g. fluorescent markers). The test polynucleotide sample is then hybridized to the immobilized oligonucleotides. The intensity of sequence-based techniques of the target polynucleotide to the immobilized probe is quantitated and compared to a reference sequence. The resulting genetic information can be used in molecular diagnosis. A common utility of the DNA chip in molecular diagnosis is screening for known mutations.

In addition to DNA chip methodology, methods using machinery adapted to DNA analysis can allow for commercialization of the disclosed methods of detection of PKD1 mutations and diagnosis of ADPKD. For example, genotyping by mass spectrometry can be used, or matrix-assisted laser desorption/ionization-time-of-flight (MALDI-TOF) mass spectrometry can be used for mass genotyping of single-base pair and short tandem repeat mutant and variant sequences. For example, PCR amplification of the region of the mutation with biotin attached to one of the primers can be conducted, followed by immobilization of the amplified DNA to streptavidin beads. Hybridization of a primer adjacent to the variant or mutant site is performed, then extension with DNA polymerase past the variant or mutant site in the presence of dNTPs and ddNTPs is performed. When suitably designed according to the sequence, this results in the addition of only a few additional bases (Braun, Little, Koster, 1997). The DNA is then processed to remove unused nucleotides and salts, and the short primer plus mutant site is removed by denaturation and transferred to silicon wafers using a piezoelectric pipette. The mass of the primer+variant or mutant site is then determined by delayed extraction MALDI-TOF mass spectrometry. Single base pair and tandem repeat variations in sequence are easily determined by their mass. This final step is very rapid, requiring only 5 sec per assay, and all of these steps can be automated, providing the potential of performing up to 20,000 genotypings per day. This technology is rapid, extremely accurate, and adaptable to any variant or mutation, can identify both single base pair and short tandem repeat variants, and adding or removing variant or mutant sequences to be tested can be done in a few seconds at trivial cost.

Another diagnostic methods for the detection of mutant PKD1 polynucleotides involves amplification, for example, by PCR (see U.S. Pat. No. 4,683,202), ligase chain reaction (Barany, Proc. Natl. Acad. Sci. USA 88:189193, 1991 a), self sustained sequence replication (Guatelli et al., Proc. Natl. Acad. Sci. USA 87:1874-1878, 1990), transcriptional amplification system (Kwoh et al., Proc. Natl. Acad. Sci. USA 86:1173-1177, 1989), Q-Beta Replicase (Lizardi et al., Bio/Technology 6:1197, 1988), or any other RNA amplification method, followed by the detection of the amplification products. The present invention provides reagents, methods and compositions that can be used to overcome prior difficulties with diagnosing ADPKD.

Using the primer pairs and methods described herein, the entire replicated segment of the PKD1 gene, including exons 1 and 22, can be amplified from genomic DNA to generate a set of eight long range amplification products, which range in size from about 0.3 kb to 5.8 kb (Table 1; see, also, FIG. 1). The availability of widely scattered PKD1-specific primers provides a means to anchor PKD1-specific amplification, and the ability to use various primer combinations provides a means to produce longer or shorter amplification products as desired. For example, the largest PKD1 fragment, which is amplified by primers BPF 13 and KG8R25 (see Table 1; SEQ ID NOS: 17 and 18, respectively), can be divided into two shorter segments by using the PKD1-specific primer, KG85R25 (SEQ ID NO:18), with forward nested primer F32 (5'-GCCTTGCGCAGCTTGGACT-3'; SEQ ID NO:53), and using BPF13 (SEQ ID NO:17) and a second specific primer, 31R (5'-ACAGTGTCTTGAGTCCAAGC-3'; SEQ ID NO:54).

It should be recognized that, while many of the primers disclosed herein are positioned with intronic sequences of the PKD1 gene, others such as SEQ ID NO:16 are positioned in coding sequences. As such, a cDNA molecule can obtained from a target RNA molecule, for example, by reverse transcription of the RNA molecule using a primer such as SEQ ID NO:16 and an appropriate second primer positioned 5' or 3' to SEQ ID NO:16. In this embodiment, a PKD1 RNA can be isolated from any tissue in which wild type PKD1 is known to be expressed, including, for example, kidney tissue, nucleated peripheral blood cells, and fibroblasts. A target sequence within the cDNA is then used as the template for a nucleic acid amplification reaction, such as a PCR amplification reaction, or the like. An amplification product can be detected, for example, using radioactively or fluorescently labeled nucleotides or the like and an appropriate detection system, or by generating a sufficient amount of the amplification product such that it can be visualized by ethidium bromide staining and gel electrophoresis.

Genomic DNA from a subject, including from a cell or tissue sample, can be used as the template for generating a long range PKD1-specific amplification product. Methods of isolating genomic DNA are well known and routine (see Sambrook et al., supra, 1989). Amplification of the genomic PKD1 DNA has advantages over the cDNA amplification process, including, for example, allowing for analysis of exons and introns of the PKD1 gene. As such, a target sequence of interest associated with either an intron or exon sequence of a PKD1 gene can be amplified and characterized. A target sequence of interest is any sequence or locus of a PKD1 gene that contains or is thought to contain a mutation, including those mutations that correlate to a PKD1-associated disorder or disease.

Using primers flanking the target sequence, a sufficient number of PCR cycles is performed to provide a PKD1-specific amplification product corresponding to the target sequence. If desired, additional amplification can be performed, for example, by performing a nested PCR reaction. Examples of primers useful for generating a PKD1-specific first amplification product from genomic DNA include the primer pairs having sequences as exemplified in SEQ ID NO:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; and SEQ ID NOS: 17 and 18. The PKD1-specific first amplification product can be further amplified using nested primers specific for a target sequence, including the primer pairs exemplified as SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; and the primer pairs formed using consecutive primers set forth in Table 2 as SEQ ID NOS:62 to 96, 113, and 97 to 112.

The amplified target sequences can be examined for changes (i.e., mutations) with respect to SEQ ID NO:1 using any of various well known methods as disclosed herein or otherwise known in the art. For example, the amplification products can simply be sequenced using routine DNA sequencing methods, particularly where only one or few amplification products are to be examined. However, DNA sequencing will be more valuable as a method of detecting mutations according to a method of the invention as sequencing technology improves and becomes more adaptable to high throughput screening assays. In addition, methods that are useful for detecting the presence of a mutation in a DNA sequence include, for example, DHPLC (Huber et al., Nucl. Acids Res. 21:1061-10666, 1993; Liu et al., Nucl. Acids Res. 26:1396-1400, 1998; Choy et al., Ann. Hum. Genet. 63:383-391, 1999; Ellis et al., Hum. Mutat. 15:556-564, 2000; which are incorporated herein by reference; see, also, Kristensen et al., supra, 2001); CSGE (Leung et al., supra, 2001); single-stranded conformation analysis (SSCA; Orita et al., Proc. Natl. Acad. Sci., USA 86:2766-2770, 1989); denaturing gradient gel electrophoresis (DGGE; Sheffield et al., Proc. Natl. Acad. Sci., USA 86:232-236, 1989); RNase protection assays; allele-specific oligonucleotides (ASOs; Handelin and Shuber, Current Protocols in Human Genetics, Suppl. 16 (John Wiley & Sons, Inc. 1998), 9:9.4.1-9.4.8); the use of proteins that recognize nucleotide mismatches, such as the *E. coli* mutS protein; and allele-specific PCR.

For allele-specific PCR, primers are used that hybridize at their 3' ends to a particular mutations. Examples of primers that can be used for allele specific PCR include an oligonucleotide of at least 10 nucleotide of SEQ ID NO:1 and that has at its 3' end nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. If the particular mutation is not present, an amplification product is not observed. Amplification Refractory Mutation System (ARMS) can also be used (see European Patent Application Publ. No. 0332435; Newton et al., Nucl. Acids. Res. 17:2503-2516, 1989).

In the SSCA, DGGE and RNase protection methods, a distinctive electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed that detects a specific sequence, and the assay is performed by detecting the presence or absence of a hybridization signal. In the mutS assay, the protein binds only to sequences that contain a nucleotide mismatch in a heteroduplex between mutant and wild-type sequences.

Denaturing gradient gel electrophoresis is based on the melting behavior of the DNA fragments and the use of denaturing gradient gel electrophoresis as shown by Fischer and Lerman, Proc. Natl. Acad. Sci. USA 80:1579-83, 1983; Myers et al.; Nucl. Acids Res. 13:3111-3129,1985; Lerman et al., in Molecular Biol. of Homo Sapiens, Cold Spring Harbor Lab. (1986) pp. 285-297. DNA fragments differing by single base substitutions can be separated from each other by electrophoresis in polyacrylamide gels containing an ascending gradient of the DNA denaturants urea and formamide. Two identical DNA fragments differing by only one single base pair, will initially move through the polyacrylamide gel at a constant rate. As they migrate into a critical concentration of denaturant, specific domains within the fragments melt to produce partially denatured DNA. Melting of a domain is accompanied by an abrupt decrease in mobility. The position in the denaturant gradient gel at which the decrease in mobility is observed corresponds to the melting temperature of that domain. Since a single base substitution within the melting domain results in a melting temperature difference, partial denaturation of the two DNA fragments will occur at different positions in the gel. DNA molecules can therefore be separated on the basis of very small differences in the melting temperature. Additional improvements to this DGGE have been made as disclosed by Borresen in U.S. Pat. No. 5,190,856. In addition, after a first DGGE analysis, an identified product can be cloned, purified and analyzed a second time by DGGE.

Denaturing high performance liquid chromatography (DHPLC; Kristensen et al., supra, 2001) and high throughput conformation sensitive gel electrophoresis (HTCSGD; Leung et al., supra, 2001) are particularly useful methods for detecting a mutant PKD1 polynucleotide sequence because the methods are readily adaptable to high throughput analysis. In addition, these methods are suitable for detecting known mutations as well as identifying previously unknown mutations. As such, these methods of detection can be adopted for use in clinical diagnostic settings. DHPLC, for example, can be used to rapidly screen a large number of samples, for example, 96 samples prepared using a 96 well microtiter plate format, to identify those showing a change in the denaturation properties. Where such a change is identified, confirmation that the PKD1 polynucleotide in the sample showing the altered denaturation property is a mutant PKD1 polynucleotide can be confirmed by DNA sequence analysis, if desired.

An oligonucleotide probe specific for a mutant PKD1 polynucleotide also can be used to detect a mutant PKD1 polynucleotide in a biological sample, including in a biological fluid, in cells or tissues obtained from a subject, or in a cellular fraction such as an organelle preparation. Cellular sources useful as samples for identifying a mutant PKD1 polynucleotide include, for example, renal cells including renal tubular epithelial cells, bile duct cells, skeletal muscle cells, lung alveolar epithelial cells, placental cells, fibroblasts and lymphocytes. Biological fluids useful as samples for identifying a mutant PKD1 polynucleotide include, for example, whole blood or serum or plasma fractions, urine, mucous, and saliva. A biological sample such as a tissue or cell sample can be obtained by any method routinely used in a clinical setting, including, for example, by cellular aspiration, biopsy or other surgical procedure.

The oligonucleotide probe can be labeled with a compound that allows detection of binding to a mutant PKD1 polynucleotide in the sample. A detectable compound can be, for example, a radioactive label, which provides a highly sensitive means for detection, or a non-radioactive label such as a fluorescent, luminescent, chemiluminescent, or enzymatically detectable label or the like (see, for example, Matthews et al., Anal. Biochem. 169:1-25, 1988).

The method of detection can be a direct or indirect method. An indirect detection process can involve, for example, the use of an oligonucleotide probe that is labeled with a hapten or ligand such as digoxigenin or biotin. Following hybridization, the target-probe duplex is detected by the formation of an antibody or streptavidin complex, which can further include an enzyme such as horseradish peroxidase, alkaline phosphatase, or the like. Such detection systems can be prepared using routine methods, or can be obtained from a commercial source. For example, the GENIUS detection system (Boehringer Mannheim) is useful for mutational analysis of DNA, and provides an indirect method using digoxigenin as a tag for the oligonucleotide probe and an anti-digoxigenin-antibody-alkaline phosphatase conjugate as the reagent for identifying the presence of tagged probe.

Direct detection methods can utilize, for example, fluorescent labeled oligonucleotides, lanthanide chelate labeled oligonucleotides or oligonucleotide-enzyme conjugates. Examples of fluorescent labels include fluorescein, rhodamine and phthalocyanine dyes. Examples of lanthanide chelates include complexes of europium ($Eu^{3+}$) or terbium ($Tb^{3+}$). Oligonucleotide-enzyme conjugates are particularly useful for detecting point mutations when using target-specific oligonucleotides, as they provide very high sensitivities of detection. Oligonucleotide-enzyme conjugates can be prepared by a number of methods (Jablonski et al., Nucl. Acids Res. 14:6115-6128, 1986; Li et al., Nucl. Acids. Res. 15:5275-5287, 1987; Ghosh et al., Bioconjugate Chem. 1:71-76, 1990). The detection of target nucleic acids using these conjugates can be carried out by filter hybridization methods or by bead-based sandwich hybridization (Ishii et al., Bioconjugate Chem. 4:34-41, 1993).

Methods for detecting a labeled oligonucleotide probe are well known in the art and will depend on the particular label. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide chelate labels, fluorescent signals can be measured with spectrofluorimeters, with or without time-resolved mode or using automated microtiter plate readers. For enzyme labels, detection is by color or dye deposition, for example, p-nitrophenyl phosphate or 5-bromo-4-chloro-3-indolyl phosphate/nitroblue tetrazolium for alkaline phosphatase, and 3,3'-diaminobenzidine-$NiCl_2$ for horseradish peroxidase, fluorescence by 4-methyl umbelliferyl phosphate for alkaline phosphatase, or chemiluminescence by the alkaline phosphatase dioxetane substrates LumiPhos 530 (Lumigen Inc., Detroit Mich.) or AMPPD and CSPD (Tropix, Inc.). Chemiluminescent detection can be carried out with X-ray or Polaroid film, or by using single photon counting luminometers, which also is a useful detection format for alkaline phosphatase labeled probes.

Mutational analysis can also be carried out by methods based on ligation of oligonucleotide sequences that anneal immediately adjacent to each other on a target DNA or RNA molecule (Wu and Wallace, Genomics 4:560-569, 1989; Landren et al., Science 241:1077-1080, 1988; Nickerson et al., Proc. Natl. Acad. Sci. USA 87:8923-8927, 1990; Barany, supra, 1991a). Ligase-mediated covalent attachment occurs only when the oligonucleotides are correctly base-paired. The ligase chain reaction (LCR) and the oligonucleotide ligation assay (OLA), which utilize the thermostable Taq ligase for target amplification, are particularly useful for interrogating mutation loci. The elevated reaction temperatures permit the ligation reaction to be conducted with high stringency (Barany, PCR Methods and Applications 1:5-16, 1991b; Grossman et al., Nucl. Acids. Res. 22:4527-4534, 1994, which are incorporated herein by reference).

Analysis of point mutations in DNA can also be carried out by using PCR and variations thereof. Mismatches can be detected by competitive oligonucleotide priming under hybridization conditions where binding of the perfectly matched primer is favored (Gibbs et al., Nucl. Acids. Res. 17:2437-2448, 1989). In the amplification refractory mutation system technique (ARMS), primers can be designed to have perfect matches or mismatches with target sequences either internal or at the 3' residue (Newton et al., supra, 1989). Under appropriate conditions, only the perfectly annealed oligonucleotide can function as a primer for the PCR reaction, thus providing a method of discrimination between normal and mutant sequences.

Detection of single base mutations in target nucleic acids can be conveniently accomplished by differential hybridization techniques using sequence-specific oligonucleotides (Suggs et al, Proc. Natl. Acad. Sci. USA 78:6613-6617, 1981; Conner et al., Proc. Natl. Acad. Sci. USA 80:278-282, 1983; Saiki et al., Proc. Natl. Acad. Sci. USA 86:6230-6234, 1989). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats can be used, including Southern blots, slot blots, reverse dot blots, solution hybridization, solid support based sandwich hybridization, bead-based, silicon chip-based and microtiter well-based hybridization formats.

An alternative strategy involves detection of the mutant sequences by sandwich hybridization methods. In this strategy, the mutant and wild type target nucleic acids are separated from non-homologous DNA/RNA using a common capture oligonucleotide immobilized on a solid support and detected by specific oligonucleotide probes tagged with reporter labels. The capture oligonucleotides can be immobilized on microtiter plate wells or on beads (Gingeras et al., J. Infect. Dis. 164:1066-1074, 1991; Richen et al., Proc. Natl. Acad. Sci. USA 88:11241-11245, 1991).

Another method for analysis of a biological sample for specific mutations in a PKD1 polynucleotide sequence (e.g., mutant PKD1 polynucleotides, or oligonucleotide portions thereof) is a multiplexed primer extension method. In this method primer is hybridized to a nucleic acid suspected of containing a mutation such that the primer is hybridized 3' to the suspected mutation. The primer is extended in the presence of a mixture of one to three deoxynucleoside triphosphates and one of three chain terminating deoxynucleoside triphosphates selected such that the wild-type extension product, the mutant DNA-derived extension product and the primer each are of different lengths. These steps can be repeated, such as by PCR or RT-PCR, and the resulting primer extended products and primer are then separated on the basis of molecular weight to thereby enable identification of mutant DNA-derived extension product.

In one aspect of the invention, the OLA is applied for quantitative mutational analysis of PKD1 polynucleotide sequences (Grossman, et al., supra, 1994). In this embodiment of the invention, a thermostable ligase-catalyzed reaction is used to link a fluorescently labeled common probe with allele-specific probes. The latter probes are sequence-coded with non-nucleotide mobility modifiers that confer unique electrophoretic mobilities to the ligation products.

Oligonucleotides specific for wild type or mutant PKD1 sequences can be synthesized with different oligomeric nucleotide or non-nucleotide modifier tails at their 5' termini. Examples of nucleotide modifiers are inosine or thymidine residues, whereas examples of non-nucleotide modifiers include pentaethyleneoxide (PEO) and hexaethyleneoxide (HEO) monomeric units. The non-nucleotide modifiers are preferred and most preferably PEO is used to label the probes. When a DNA template is present, a thermostable DNA ligase catalyzes the ligation of normal and mutant probes to a common probe bearing a fluorescent label. The PEO tails modify the mobilities of the ligation products in electrophoretic gels. The combination of PEO tails and fluorophor labels (TET and FAM (5-carboxy-fluorescein derivatives)), HEX and JOE (6-carboxy-fluorescein derivatives), ROX (6-carboxy-x-rhodamine), or TAMRA (N, N, N', N'-tetramethyl-6-carboxy-rhodamine; Perkin-Elmer, ABI Division, Foster City Calif.) allow multiplex analysis based on size and color by providing unique electrophoretic signatures to the ligation products. The products are separated by electrophoresis, and fluorescence intensities associated with wild type and mutant products are used to quantitate heteroplasmy. Thus, wild type and mutant, including variant, sequences are detected and quantitated on the basis of size and fluorescence intensities of the ligation products. This method further can be configured for quantitative detection of multiple PKD1 polynucleotide mutations in a single ligation reaction.

Mismatch detection or mutation analysis can also be performed using mismatch specific DNA intercalating agents. Such agents intercalate at a site having a mismatch followed by visualization on a polyacrylamide or agarose gel or by electrocatalysis. Accordingly, PKD1 polynucleotide sequences can be contacted with probes specific for a PKD1 mutation or probes that are wild type for an area having a specific mutation under conditions such that the PKD1 polynucleotide and probe hybridize. The hybridized sequences are then contacted with a mismatch intercalating agent and, for example, separated on a gel. Visualized bands on the gel correspond to a sequence having a mismatch. If the probes are wild-type probes mismatches will occur if the target PKD1 sequence contains a mismatch. If the probes are specific for a mutated sequence mismatches will be present where the target PKD1 sequence is wild type, but the hybridized or duplex sequences will not contain mismatches where the probe sequence hybridizes to a PKD1 sequence containing the same mutation.

For quantitative analysis of PKD1 mutations using OLA, oligonucleotide probes are preferably labeled with fluorophor labels that provide spectrally distinguishable characteristics. In one embodiment, oligonucleotides are labeled with 5' oligomeric PEO tails. Synthesis of such 5' labeled oligonucleotides can be carried out, for example, using an automated synthesizer using standard phosphoramidite chemistry. Following cleavage from resin and deprotection with ammonium hydroxide, the $(PEO)_n$-oligonucleotides can be purified by reverse phase HPLC. Oligonucleotides with 3'-FAM or TET dyes (Perkin Elmer) and 5'-phosphates can be synthesized and purified by the procedure of Grossman et al., supra, 1994. The 5'-PEO-labeled probes can be synthesized to have 5'-PEO-tails of differing lengths to facilitate distinguishing the ligated probe products both electrophoretically by size and by spectral characteristics of the fluorophor labels.

The oligonucleotide probes are used for identifying mutant PKD1 polynucleotides, which can be indicative of a PKD1-associated disorder such as ADPKD. Preferably, the probes are specific for one or more PKD1 nucleotide positions of SEQ ID NO:1 selected from nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T. The oligonucleotide probes for the OLA assay are typically designed to have calculated melting temperatures of about 40° C. to 50° C., generally about 48° C., by the nearest neighbor method (Breslaur et al., Proc. Natl. Acad. Sci. USA 83:9373-9377, 1986) so that the ligation reaction can be performed at a temperature range of about 40° C. to 60° C., typically from about 45° C. to about 55° C. The wild type and mutant, including variant, oligonucleotide probes can be synthesized with various combinations of PEO oligomeric tails and fluorescein dyes such as TET and FAM. These combinations of mobility modifiers and fluorophor labels furnish electrophoretically unique ligation products that can enable the monitoring of two or more PKD1 nucleotide sites in a single ligation reaction.

In one embodiment, a method of diagnosing a PKD1-associated disorder in a subject is performed by amplifying a portion of a PKD1 polynucleotide in a nucleic acid sample from a subject suspected of having a PKD1-associated disorder with at least a first primer pair to obtain a first amplification product, wherein said first primer pair is a primer pair of claim 3; amplifying the first amplification product with at least a second primer pair to obtain a nested amplification product, wherein the second primer pair is suitable for performing nested amplification of the first amplification product; and determining whether the nested amplification product has a mutation associated with a PKD1-associated disorder, wherein the presence of a mutation associated with a PKD1-associated disorder is indicative of a PKD1-associated disorder, thereby diagnosing a PKD1-associated disorder in the subject. The method can be performed using a first primer pair selected from SEQ ID NOS:3 and 4; SEQ ID NOS:5 and 6; SEQ ID NOS:7 and 8; SEQ ID NOS:9 and 10; SEQ ID NOS:11 and 12; SEQ ID NOS:13 and 14; SEQ ID NOS:15 and 16; SEQ ID NOS:17 and 18; and a combination thereof, and a second primer pair selected from SEQ ID NOS:19 and 20; SEQ ID NOS:21 and 22; SEQ ID NOS:23 and 24; SEQ ID NOS:25 and 26; SEQ ID NOS:27 and 28;

SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS:105 and 106; SEQ ID NOS:107 and 108; SEQ ID NOS:109 and 110; or SEQ ID NOS:111 and 112; and a combination thereof.

In another embodiment, a method of diagnosing a PKD1-associated disorder in a subject is performed by amplifying a portion of PKD1 polynucleotide in a nucleic acid sample from a subject suspected of having a PKD1-associated disorder with a first primer pair to obtain a first amplification product; amplifying the first amplification product using a second primer pair to obtain a second amplification product; and detecting a mutation in the second amplification product, wherein the mutation comprises SEQ ID NO:1 wherein nucleotide 3110 is a C; nucleotide 3336 is deleted; nucleotide 3707 is an A; nucleotide 5168 is a T; nucleotide 6078 is an A; nucleotide 6089 is a T; nucleotide 6326 is a T; nucleotides 7205 to 7211 are deleted; nucleotide 7415 is a T; nucleotide 7433 is a T; nucleotide 7883 is a T; or nucleotides 8159 to 8160 are deleted; nucleotide 8298 is a G; nucleotide 9164 is a G; nucleotide 9213 is an A; or nucleotide 9326 is a T; nucleotide 10064 is an A; or wherein a GCG nucleotide sequence is inserted between nucleotides 7535 and 7536; or a combination thereof, thereby diagnosing a PKD1-associated disorder in the subject.

The present invention also provides a method of identifying a subject having or at risk of having a PKD1-associated disorder. Such a method can be performed, for example, by comprising contacting nucleic acid molecules in a sample from a subject with at least one primer pair of the invention under conditions suitable for amplification of a PKD1 polynucleotide by the primer pair, thereby generating a PKD1-specific amplification product; and testing an amplification product for the presence or absence of a mutation indicative of a PKD1-associated disorder, wherein the absence of the mutation identifies the subject a not having or at risk of the having a PKD1-associated disorder, and wherein the presence of the mutation identifies the subject as having or is at risk of having a PKD1-associated disorder. The primer pair can be, for example, selected from SEQ ID NO:3 and 4; SEQ ID NO:5 and 6; SEQ ID NOS:7 and 8; SEQ ID NOS:9 and 10; SEQ ID NOS:11 and 12; SEQ ID NOS:13 and 14; SEQ ID NOS:15 and 16; or SEQ ID NOS:17 and 18. The PKD1-associated disorder can be autosomal dominant polycystic kidney disease, acquired cystic disease, or any other PKD-1 associated disorder, and the subject can be, for example, a vertebrate, particularly a human subject.

Such a method is particularly adaptable to a high throughput format, and, if desired, can include a step of contacting the PKD1-specific amplification product with at least a second primer pair, under conditions suitable for nested amplification of the PKD1-specific amplification product by a second primer pair, thereby generating a nested amplification product, then testing the nested amplification product for the presence or absence of a mutation indicative of a PKD1-associated disorder. The second primer pair can be any primer pair suitable for nested amplification of the PKD1-specific amplification product, for example, a primer pair selected from SEQ ID NOS:19 and 20; SEQ ID NOS:21 and 22; SEQ ID NOS:23 and 24; SEQ ID NOS:25 and 26; SEQ ID NOS:27 and 28; SEQ ID NOS:29 and 30; SEQ ID NOS:31 and 32; SEQ ID NOS:33 and 34; SEQ ID NOS:35 and 36; SEQ ID NOS:37 and 38; SEQ ID NOS:39 and 40; SEQ ID NOS:41 and 42; SEQ ID NOS:43 and 44; SEQ ID NOS:45 and 46; SEQ ID NOS:47 and 48; SEQ ID NOS:49 and 50; SEQ ID NOS:51 and 61; SEQ ID NOS:62 and 63; SEQ ID NOS:64 and 65; SEQ ID NOS:66 and 67; SEQ ID NOS:68 and 69; SEQ ID NOS:70 and 71; SEQ ID NOS:72 and 73; SEQ ID NOS:74 and 75; SEQ ID NOS:76 and 77; SEQ ID NOS:78 and 79; SEQ ID NOS:80 and 81; SEQ ID NOS:82 and 83; SEQ ID NOS:84 and 85; SEQ ID NOS:86 and 87; SEQ ID NOS:88 and 89; SEQ ID NOS:90 and 91; SEQ ID NOS:92 and 93; SEQ ID NOS:94 and 95; SEQ ID NOS:96 and 113; SEQ ID NOS:97 and 98; SEQ ID NOS:99 and 100; SEQ ID NOS:101 and 102; SEQ ID NOS:103 and 104; SEQ ID NOS:105 and 106; SEQ ID NOS:107 and 108; SEQ ID NOS:109 and 110; or SEQ ID NOS:111 and 112; and a combination thereof.

Testing an amplification product for the presence or absence of the mutation can be performed using any of various well known methods for examining a nucleic acid molecule. For example, nucleotide sequence of the amplification product can be determined, and compared with the nucleotide sequence of a corresponding nucleotide sequence of SEQ ID NO:1. The amplification product also can be tested by determining the melting temperature of the amplification product, and comparing the melting temperature to the melting temperature of a corresponding nucleotide sequence of SEQ ID NO:1. The melting temperature can be determined, for example, using denaturing high performance liquid chromatography.

Where a nested amplification is to be performed, the method can include a step directed to reducing contamination of the PKD1-specific amplification product by genomic DNA prior to contacting the PKD1-specific amplification product with the at least second set of primer pairs. For example, contamination of the PKD1-specific amplification product can be reduced by diluting the PKD1-specific amplification product.

The mutation indicative of a of PKD1 associated disorder can be, for example, a nucleotide sequence substantially identical to SEQ ID NO:1, wherein nucleotide 3110 is a C; nucleotide 8298 is a G; nucleotide 9164 is a G; nucleotide 9213 is an A; nucleotide 9326 is a T; or nucleotide 10064 is an A; or can be a nucleotide sequence substantially identical to SEQ ID NO:1, wherein nucleotide 3336 is deleted; nucleotide 3707 is an A; nucleotide 5168 is a T; nucleotide 6078 is an A; nucleotide 6089 is a T; nucleotide 6326 is a T; nucleotides 7205 to 7211 are deleted; nucleotide 7415 is a T; nucleotide 7433 is a T; nucleotide 7883 is a T; or nucleotides 8159 to 8160 are deleted; or wherein a GCG nucleotide sequence is inserted between nucleotides 7535 and 7536.

Data that is collected pursuant to a step of detecting the presence or absence of a mutation indicative of a PKD1-associated disorder in an amplification product, which can be an amplification product generated according to a method of the invention, including, for example, a PKD1-specific amplification product or a nested amplification product, can be accumulated, and can be formatted into a form that facilitates determining, for example, whether a subject is at risk of a PKD1-associated disorder. As such, the data can be formatted into a report that indicates whether a subject is at risk of a PKD1-associate disorder. The report can be in any of various forms, including, for example, contained in a computer random access or read-only memory, or stored on a diskette, CD, DVD, magnetic tape; presented on a visual display such as a computer monitor or other cathode ray tube or liquid crystal display; or printed on paper. Furthermore, the data, which can be formatted into a report, can be transmitted to a user interested in or privy to the information. The data or report can be transmitted using any convenient medium, for example, via the internet, by facsimile or by mail, depending on the form of the data or report.

Also provided is a method of detecting the presence of a mutant PKD1 polynucleotide in a sample by contacting a sample suspected of containing a mutant PKD1 polynucleotide with an oligonucleotide of the invention under conditions that allow the oligonucleotide to selectively hybridize with a mutant PKD1 polynucleotide; and detecting selective hybridization of the oligonucleotide and a mutant PKD1 polynucleotide, thereby detecting the presence of a mutant PKD1 polynucleotide sequence in the sample. In another embodiment, a method of detecting the presence of a mutant PKD1 polypeptide in a sample is provided, for example, by contacting a sample suspected of containing a mutant PKD1 polypeptide with an antibody of the invention under conditions that allow the antibody to specifically bind a mutant PKD1 polypeptide; and detecting specific binding of the antibody and the mutant PKD1 polypeptide in the sample, thereby detecting the presence of a mutant PKD1 polypeptide in a sample. The mutant PKD1 polypeptide can have a sequence, for example, substantially as set forth in SEQ ID NO:2, and having a mutation of A88V, W967R, L2696R, R2985G, W3001X, R3039C, V3285I, H3311R, or a combination thereof (see, also, Table 4).

Antibodies that can specifically bind wild type or mutant PKD1 polypeptides, or peptide portions thereof, can also be used as ADPKD diagnostic reagents. Such reagents provide a diagnostic method that can detect the expression of abnormal PKD1 proteins or of abnormal levels of PKD1 protein expression, including the detection of mutant PKD1 polypeptides or aberrant cellular localization of a PKD1 protein. For example, differences in the size, electronegativity, or antigenicity of the mutant PKD1 protein relative to a wild type PKD1 protein can be detected.

Diagnostic methods for the detection of mutant PKD1 polypeptides or peptide portions thereof can involve, for example, immunoassays wherein epitopes of a mutant PKD1 polypeptide are detected by their interaction with an anti-PKD1 specific antibody (e.g., an anti-mutant PKD1 specific antibody). For example, an antibody that specifically binds to a mutant PKD1 polypeptide does not bind to a wild-type PKD1 polypeptide or peptide thereof. Particular epitopes of PKD1 to which antibodies can be developed include peptides that are substantially identical to SEQ ID NO:2, and having at least five amino acids, including amino acid residue 88, wherein residue 88 is a V; residue 967, wherein residue 967 is an R; residue 2696, wherein residue 2696 is an R; residue 2985, wherein residue 2985 is a G; residue 3039, wherein residue 3039 is a C; residue 3285, wherein residue 3285 is an I; or residue 3311, wherein residue 3311 is an R; or a C-terminal peptide including amino acid residue 3000, where residue 3001 is absent and the mutant PKD1 polypeptide is truncated due to the presence of a STOP codon in the encoding mutant PKD1 polynucleotide.

Antibodies, or fragments of antibodies, such as those described, above, are useful in the present invention and can be used to quantitatively or qualitatively detect the presence of wild type or mutant PKD1 polypeptides or peptide portions thereof, for example. This can be accomplished, for example, by immunofluorescence techniques employing a fluorescently labeled antibody (see below) coupled with light microscopic, flow cytometric, or fluorimetric detection.

The antibodies (or fragments thereof useful in the present invention can, additionally, be employed histologically, as in immunofluorescence or immunoelectron microscopy, for in situ detection of PKD1 polypeptide, peptides, variants or mutants thereof. Detection can be accomplished by removing a histological specimen from a subject, and applying thereto a labeled antibody of the present invention. The histological sample can be taken from a tissue suspected of exhibiting ADPKD. The antibody (or fragment) is preferably applied by overlaying the labeled antibody (or fragment) onto a biological sample. Through the use of such a procedure, it is possible to determine not only the presence of PKD1 polypeptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant PKD1 polypeptide or peptide portions thereof typically comprise incubating a biological sample, such as a biological fluid, a tissue extract, freshly harvested cells, or cells that have been incubated in tissue culture, in the presence of a detectably labeled antibody capable of identifying a PKD1 polypeptide, mutant PKD1 polypeptide and peptide portions thereof, and detecting the bound antibody by any of a number of techniques well-known in the art. The biological sample can be brought in contact with and immobilized onto a solid phase support or carrier such as nitrocellulose, or other solid support that is capable of immobilizing cells, cell particles or soluble proteins. The support can then be washed with suitable buffers followed by treatment with the detectably labeled mutant PKD1 specific antibody, preferably an antibody that recognizes a developed include peptides that are substantially identical to SEQ ID NO:2, and having at least five amino acids, including amino acid residue 88, wherein residue 88 is a V; residue 967, wherein residue 967 is an R; residue 2696, wherein residue 2696 is an R; residue 2985, wherein residue 2985 is a G; residue 3039, wherein residue 3039 is a C; residue 3285, wherein residue 3285 is an I; or residue 3311, wherein residue 3311 is an R; or a C-terminal peptide including amino acid residue 3000, where residue 3001 is absent and the mutant PKD1 polypeptide is truncated due to the presence of a STOP codon in the encoding mutant PKD1 polynucleotide (see, also, Table 4). The solid phase support can then be washed with the buffer a second time to remove unbound antibody, and the amount of bound label on solid support can be detected by conventional means specific for the label.

A "solid phase support" or "carrier" can be any support capable of binding an antigen or an antibody. Well-known supports or carriers include glass, polystyrene, polypropylene, polyethylene, dextran, nylon, amylases, natural and modified celluloses, polyacrylamides, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, or the like. Those skilled in the art will know many other suitable carriers for binding antibody or antigen, or will be able to ascertain the same by use of routine experimentation.

The binding activity of a given lot of an anti-mutant PKD1 antibody can be determined according to well known methods. Those skilled in the art will be able to determine operative and optimal assay conditions for each determination by employing routine experimentation. One of the ways in which the mutant PKD1-specific antibody can be detectably labeled is by linking the antibody to an enzyme and use the enzyme labeled antibody in an enzyme immunoassay (EIA; Voller, "The Enzyme Linked Immunosorbent Assay (ELISA):, Diagnostic Horizons 2:1-7, 1978; Microbiological Associates Quarterly Publication, Walkersville, Md.); Voller et al., J. Clin. Pathol. 31:507-520, 1978; Butler, Meth. Enzymol. 73:482-523, 1981; Maggio (ed.), "Enzyme Immunoassay", CRC Press, Boca Raton FL, 1980; Ishikawa et al., (eds.), "Enzyme Immunoassay", Kgaku Shoin, Tokyo, 1981). The enzyme that is bound to the antibody will react with an appropriate substrate, preferably a chromogenic substrate, in such a manner as to produce a chemical moiety that can be detected, for example, by spectrophotometric, fluorimetric or by visual means.

Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection can also be accomplished by visual comparison of the extent of enzymatic reaction of a substrate in comparison with similarly prepared standards. In addition, detection can be accomplished using any of a variety of other immunoassays, including, for example, by radioactively labeling the antibodies or antibody fragments and detecting PKD1 wild type or mutant peptides using a radioimmunoassay (RIA; see, for example, Weintraub, Principles of Radioimmunoassays, Seventh Training Course on Radioligand Assay Techniques, The Endocrine Society, March, 1986, which is incorporated herein by reference). The radioactive isotope can be detected by such means as the use of a gamma counter or a scintillation counter or by autoradiography.

The antibody also can be labeled with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester. Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In vitro systems can be designed to identify compounds capable of binding a mutant PKD1 polynucleotide of the invention (e.g., a polynucleotide having a sequence substantially identical to SEQ ID NO:1 and having a mutation such as C474T; G487A; T3110C; T8298G; A9164G; G9213A; C9326T; C9367T; G10064A; A10143G; T10234C; or G10255T). Such compounds can include, but are not limited to, peptides made of D-and/or L-configuration amino acids in, for example, the form of random peptide libraries (see, e.g., Lam et al., Nature 354:82-84, 1981), phosphopeptides in, for example, the form of random or partially degenerate, directed phosphopeptide libraries (see, e.g., Songyang et al., Cell 72:767-778, 1993), antibodies, and small or large organic or inorganic molecules. Compounds identified can be useful, for example, in modulating the activity of PKD1 proteins, variants or mutants. For example, mutant PKD1 polypeptides of the invention can be useful in elaborating the biological function of the PKD1 protein. Such mutants can be utilized in screens for identifying compounds that disrupt normal PKD1 interactions, or can in themselves disrupt such interactions.

The principle of the assays used to identify compounds that bind to a mutant PKD1 protein involves preparing a reaction mixture of the PKD1 protein, which can be a mutant, including a variant, and the test compound under conditions and for a time sufficient to allow the two components to interact, then isolating the interaction product (complex) or detecting the complex in the reaction mixture. Such assays can be conducted in a heterogeneous or homogeneous format. Heterogeneous assays involve anchoring PKD or the test substance onto a solid phase and detecting PKD1 test substance complexes anchored on the solid phase at the end of the reaction. In homogeneous assays, the entire reaction is carried out in a liquid phase. In either approach, the order of addition of reactants can be varied to obtain different information about the compounds being tested.

In addition, methods suitable for detecting protein-protein interactions can be employed for identifying novel PKD1 cellular or extracellular protein interactions based upon the mutant or variant PKD1 polypeptides of the invention. For example, some traditional methods that can be employed are co-immunoprecipitation, crosslinking and copurification through gradients or chromatographic columns. Additionally, methods that result in the simultaneous identification of the genes coding for the protein interacting with a target protein can be employed. These methods include, for example, probing expression libraries with labeled target protein, using this protein in a manner similar to antibody probing of kgt libraries. One such method for detecting protein interactions in vivo is the yeast two hybrid system. One version of this system has been described (Chien et al., Proc. Natl. Acad. Sci. USA 88:9578-9582, 1991) and can be performed using commercially available reagents (Clontech; Palo Alto Calif.).

A PKD1 polypeptide (e.g., a variant or mutant) of the invention can interact with one or more cellular or extracellular proteins in vivo. Such cellular proteins are referred to herein as "binding partners". Compounds that disrupt such interactions can be useful in regulating the activity of a PKD1 polypeptide, especially mutant PKD1 polypeptides. Such compounds include, for example, molecules such as antibodies, peptides, peptidomimetics and the like.

In instances whereby ADPKD symptoms are associated with a mutation within the PKD1 polynucleotide (e.g., SEQ ID NO:1 having a mutation at T3110C; T8298G; A9164G;

G9213A; C9326T; G10064A or the like; see Example 2), which produces PKD1 polypeptides having aberrant activity, compounds identified that disrupt such activity can therefore inhibit the aberrant PKD1 activity and reduce or treat ADPKD1-associated symptoms or ADPKD disease, respectively (see Table 4). For example, compounds can be identified that disrupt the interaction of mutant PKD1 polypeptides with cellular or extracellular proteins, for example, the PKD2 gene product, but do not substantially effect the interactions of the normal PKD1 protein. Such compounds can be identified by comparing the effectiveness of a compound to disrupt interactions in an assay containing normal PKD1 protein to that of an assay containing mutant PKD1 polypeptide, for example, a two hybrid assay.

The basic principle of the assay systems used to identify compounds that interfere with the interaction between the PKD1 protein, preferably a mutant PKD1 protein, and its cellular or extracellular protein binding partner or partners involves preparing a reaction mixture containing the PKD1 protein and the binding partner under conditions and for a time sufficient to allow the two proteins to interact or bind, thus forming a complex. In order to test a compound for inhibitory activity, reactions are conducted in the presence or absence of the test compound, i.e., the test compound can be initially included in the reaction mixture, or added at a time subsequent to the addition of PKD1 and its cellular or extracellular binding partner; controls are incubated without the test compound or with a placebo. The formation of any complexes between the PKD1 protein and the cellular or extracellular binding partner is then detected. The formation of a complex or interaction in the control reaction, but not in the reaction mixture containing the test compound indicates that the compound interferes with the interaction of the PKD1 protein and the binding partner. As noted above, complex formation or component interaction within reaction mixtures containing the test compound and normal PKD1 protein can also be compared to complex formation or component interaction within reaction mixtures containing the test compound and mutant PKD1 protein. This comparison can be important in those cases wherein it is desirable to identify compounds that disrupt interactions of mutant but not normal PKD1 proteins.

Any of the binding compounds, including but not limited to, compounds such as those identified in the foregoing assay systems can be tested for anti-ADPKD activity. ADPKD, an autosomal dominant disorder, can involve underexpression of a wild-type PKD1 allele, or expression of a PKD1 polypeptide that exhibits little or no PKD1 activity. In such an instance, even though the PKD1 polypeptide is present, the overall level of normal PKD1 polypeptide present is insufficient and leads to ADPKD symptoms. As such increase in the level of expression of the normal PKD1 polypeptide, to levels wherein ADPKD symptoms are ameliorated would be useful. Additionally, the term can refer to an increase in the level of normal PKD1 activity in the cell, to levels wherein ADPKD symptoms are ameliorated.

The identified compounds that inhibit PKD1 expression, synthesis and/or activity can be administered to a patient at therapeutically effective doses to treat polycystic kidney disease. A therapeutically effective dose refers to that amount of the compound sufficient to result in amelioration of symptoms of polycystic kidney disease. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography. Additional factors that can be utilized to optimize dosage can include, for example, such factors as the severity of the ADPKD symptoms as well as the age, weight and possible additional disorders that the patient can also exhibit. Those skilled in the art will be able to determine the appropriate dose based on the above factors.

Pharmaceutical compositions for use in accordance with the present invention can be formulated in conventional manner using one or more physiologically acceptable carriers or excipients. Thus, the compounds and their physiologically acceptable salts and solvates can be formulated for administration by inhalation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycollate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound. For buccal administration the compositions can take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant such as dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g., gelatin, for use in an inhaler can be formulated containing a powder mix of the compound and a suitable powder base such as lactose or starch.

The compounds can be formulated for parenteral administration by injection, e.g., by bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can for example comprise metal or plastic foil, such as a blister pack. The pack or dispenser device can be accompanied by instructions for administration.

Alternatively, ADPKD can be caused by the production of an aberrant mutant form of the PKD1 protein, that either interferes with the normal allele product or introduces a novel function into the cell, which then leads to the mutant phenotype. For example, a mutant PKD1 protein can compete with the wild type protein for the binding of a substance required to relay a signal inside or outside of a cell.

Cell based and animal model based assays for the identification of compounds exhibiting anti-ADPKD activity are also encompassed within the present invention. Cells that contain and express mutant PKD1 polynucleotide sequences (e.g., a sequence substantially identical to the sequence as set forth in SEQ ID NO:1 and having one or more mutations of a C474T; G487A; T3110C; T8298G; A9164G; G9213A; C9326T; C9367T; G10064A; A10143G; T10234C; G10255T or the like; see Example 2), which encode a mutant PKD1 polypeptide, and thus exhibit cellular phenotypes associated with ADPKD, can be utilized to identify compounds that possess anti-ADPKD activity. Such cells can include cell lines consisting of naturally occurring or engineered cells that express mutant or express both normal and mutant PKD1 polypeptides. Such cells include, but are not limited to renal epithelial cells, including primary and immortalized human renal tubular cells, MDCK cells, LLPCK1 cells, and human renal carcinoma cells. Methods of transforming cell with PKD1 polynucleotide sequences encoding wild-type or mutant proteins are described above.

Cells that exhibit ADPKD-like cellular phenotypes, can be exposed to a compound suspected of exhibiting anti-ADPKD activity at a sufficient concentration and for a time sufficient to elicit an anti-ADPKD activity in the exposed cells. After exposure, the cells are examined to determine whether one or more of the ADPKD-like cellular phenotypes has been altered to resemble a more wild type, non-ADPKD phenotype.

Among the cellular phenotypes that can be followed in the above assays are differences in the apical/basolateral distribution of membrane proteins. For example, normal (i.e., non-ADPKD) renal tubular cells in situ and in culture under defined conditions have a characteristic pattern of apical/basolateral distribution of cell surface markers. ADPKD renal cells, by contrast, exhibit a distribution pattern that reflects a partially reversed apical/basolateral polarity relative to the normal distribution. For example, sodium-potassium ATPase generally is found on the basolateral membranes of renal epithelial cells, but also can be found on the apical surface of ADPKD epithelial cells, both in cystic epithelia in vivo and in ADPKD cells in culture (Wilson et al., Am. J. Physiol. 260: F420-F430, 1991). Another marker that exhibits an alteration in polarity in normal versus ADPKD affected cells is the EGF receptor, which is normally located basolaterally, but in ADPKD cells is mislocated to the apical surface. Such a apical/basolateral marker distribution phenotype can be followed, for example, by standard immunohistology techniques using antibodies specific to a markers of interest.

Assays for the function of PKD1 also can include a measure of the rate of cell growth or apoptosis, since dysregulation of epithelial cell growth can be a key step in cyst formation. The cysts are fluid filled structures lined by epithelial cells that are both hyper-proliferative and hyper-apoptotic (Evan et al., Kidney International 16:743-750, 1979; Kovacs and Gomba, Kidney Blood Press. Res. 21:325-328, 1998; Lanoix et al., Oncogene 13: 1153-1160, 1996; Woo, New Engl. J. Med. 333:18-25, 1995, each of which is incorporated herein by reference). The cystic epithelium has a high mitotic rate in vivo as measured by PCNA staining (Nadasdy et al., J. Am. Soc. Nephrol. 5:1462-1468, 1995, which is incorporated herein by reference), and increased levels of expression of other markers of proliferation (Klingel et al., Amer. J. Kidney Dis. 19:22-30, 1992, which is incorporated herein by reference). In addition, cultured cells from ADPKD cystic kidneys have increased growth rates in vitro (Wilson et al., Kidney Int. 30:371-380, 1986; . Wilson, Amer. J. Kidney Dis. 17:634-637, 1991, each of which is incorporated herein by reference).

Further, in studies of rodent models of polycystic kidney disease, the epithelial cells that line cysts of animals with naturally occurring forms of PKD showed abnormalities similar to those reported in human ADPKD (Harding et al., 1992; Ramasubbu et al., J. Am. Soc. Nephrol. 9:937-945, 1998; Rankin et al., J. Cell Physiol. 152:578-586, 1992; Rankin et al., In Vitro Cell Devel. Biol. Anim. 32:100-106, 1996, each of which is incorporated herein by reference). Moreover, mice that have transgenic over-expression of either c-myc or SV40-large T antigen developed PKD (Kelley et al. J. Am. Soc. Nephrol. 2:84-97, 1991; Trudel et al., Kidney Int. 39:665-671 1991, each of which is incorporated herein by reference). Also, expression of recombinant full length PKD1 in epithelial cells reduced their rate of growth and induced resistance to apoptosis when challenged with stimuli such as serum starvation or exposure to UV light, which are known to stimulate apoptosis (Boletta et al., Mol. Cell 6:1267-1273, 2000, which is incorporated herein by reference). As such, biochemical pathways that are activated by PKD1 expression, including, for example, JAK2, STAT1/3, P13 kinase, p21, and AKT, can provide surrogate markers for PKD1 activity.

The propensity of an epithelial cell to form tubules provides still another assay for the function of PKD1. In vivo, PKD is characterized by cystic transformation of renal tubules and pancreatic and biliary ductules. In vitro, expression of full length PKD1 induces spontaneous tubulogenesis in MDCK cells (Boletta et al., supra, 2000). In this model system, control MDCK cells, which did not express recombinant wild type full length PKD1, formed cystic structures unless treated with hepatocyte growth factor or with fibroblast conditioned medium when cultured suspended in collagen. In contrast, MDCK cells that expressed the full length wild type recombinant form of PKD1 spontaneously formed tubules in the absence of exogenous factors when cultured in this manner. As such, this model system can be used to identify ligands that bind to and activate the PKD1 protein, to determine pathways that are targeted for activation by therapeutic agents, and as an assay system to evaluate the effect of sequence variants on PKD1 function.

Additionally, assays for the function of a PKD1 polypeptide can, for example, include a measure of extracellular matrix (ECM) components, such as proteoglycans, laminin, fibronectin and the like, in that studies in both ADPKD and in rat models of acquired cystic disease (Carone et al., Kidney International 35:1034-1040, 1989) have shown alterations in such components. Thus, any compound that serves to create an extracellular matrix environment that more fully mimics the normal ECM should be considered as a candidate for testing for an ability to ameliorate ADPKD symptoms.

In addition, it is contemplated that the present invention can be used to measure the ability of a compound, such as those identified in the foregoing binding assays, to prevent or inhibit disease in animal models for ADPKD. Several naturally-occurring mutations for renal cystic disease have been found in animals, and are accepted in the art as models of ADPKD and provide test systems for assaying the effects of compounds that interact with PKD1 proteins. Of these models, the Han:SPRD rat model, provides an autosomal dominant model system (see, for example, Kaspareit-Ritting-hausen et al., Vet. Path. 26:195, 1989), and several recessive models also are available (Reeders, Nature Genetics 1:235, 1992). In addition, knock-out mice, in which the PKD1 or PKD2 gene has been disrupted, are available and provide a relevant model system for genetic forms of ADPKD. As such, the PKD1 and PKD2 knock-out mice can be useful for confirming the effectiveness in vivo of compounds that interact with PKD1 proteins in vitro (see, for example, Wu et al., Nat. Genet. 24:75-78, 2000; Kim et al., Proc. Natl. Acad. Sci., USA 97:1731-1736, 2000; Lu et al., Nat. Genet. 21:160-161, 1999; Wu et al., Cell 93:177-188, 1998; Lu et al., Nat. Genet. 17:179-181, 1997, each of which is incorporated herein by reference).

Animal models exhibiting ADPKD-like symptoms associated with one or more of the mutant PKD1 polynucleotide sequences as disclosed herein can also be engineered by utilizing the PKD1 polynucleotide sequences such in conjunction with well known methods for producing transgenic animals. Animals of any species, including, but not limited to, mice, rats, rabbits, guinea pigs, pigs, mini-pigs, goats, and non-human primates, e.g., baboons, squirrels, monkeys, and chimpanzees can be used to generate such ADPKD animal models or transgenic animals. In instances where the PKD1 mutation leading to ADPKD symptoms causes a drop in the level of PKD1 protein or causes an ineffective PKD1 protein to be made (e.g., the PKD1 mutation is a dominant loss-of-function mutation, such as a W3001X, i.e., truncated after amino acid residue 3000, or a T3110C mutation; see, also, Table 4) various strategies can be utilized to generate animal models exhibiting ADPKD-like symptoms.

The present invention also provides transgenic non-human organisms, including invertebrates, vertebrates and mammals. For purposes of the subject invention, these animals are referred to as "transgenic" when such animal has had a heterologous DNA sequence, or one or more additional DNA sequences normally endogenous to the animal (collectively referred to herein as "transgenes") chromosomally integrated into the germ cells of the animal. The transgenic animal (including its progeny) will also have the transgene integrated into the chromosomes of somatic cells.

Various methods to make the transgenic animals of the subject invention can be employed. Generally speaking, three such methods can be employed. In one such method, an embryo at the pronuclear stage (a "one cell embryo") is harvested from a female and the transgene is microinjected into the embryo, in which case the transgene will be chromosomally integrated into both the germ cells and somatic cells of the resulting mature animal. In another such method, embryonic stem cells are isolated and the transgene incorporated therein by electroporation, plasmid transfection or microinjection, followed by reintroduction of the stem cells into the embryo where they colonize and contribute to the germ line. Methods for microinjection of mammalian species is described in U.S. Pat. No. 4,873,191.

In yet another such method, embryonic cells are infected with a retrovirus containing the transgene whereby the germ cells of the embryo have the transgene chromosomally integrated therein. When the animals to be made transgenic are avian, because avian fertilized ova generally go through cell division for the first twenty hours in the oviduct, microinjection into the pronucleus of the fertilized egg is problematic due to the inaccessibility of the pronucleus. Therefore, of the methods to make transgenic animals described generally above, retrovirus infection is preferred for avian species, for example as described in U.S. Pat. No. 5,162,215. If microinjection is to be used with avian species, however, the method of Love et al., (Biotechnology, 12, Jan 1994) can be utilized whereby the embryo is obtained from a sacrificed hen approximately two and one-half hours after the laying of the previous laid egg, the transgene is microinjected into the cytoplasm of the germinal disc and the embryo is cultured in a host shell until maturity. When the animals to be made transgenic are bovine or porcine, microinjection can be hampered by the opacity of the ova thereby making the nuclei difficult to identify by traditional differential interference-contrast microscopy. To overcome this problem, the ova can first be centrifuged to segregate the pronuclei for better visualization.

The non-human transgenic animals of the invention include, for example, bovine, porcine, ovine and avian animals (e.g, cow, pig, sheep, chicken, turkey). Such transgenic non-human animals are produced by introducing a transgene into the germline of the non-human animal. Embryonal target cells at various developmental stages can be used to introduce transgenes. Different methods are used depending on the stage of development of the embryonal target cell. The zygote is the best target for microinjection. The use of zygotes as a target for gene transfer has a major advantage in that in most cases the injected DNA will be incorporated into the host gene before the first cleavage (Brinster et al., Proc. Natl. Acad. Sci. USA 82:4438-4442, 1985). As a consequence, all cells of the transgenic non-human animal will carry the incorporated transgene. This will in general also be reflected in the efficient transmission of the transgene to offspring of the founder since 50% of the germ cells will harbor the transgene.

The term "transgenic" is used to describe an animal that includes exogenous genetic material within all of its cells. A transgenic animal can be produced by cross-breeding two chimeric animals that include exogenous genetic material within cells used in reproduction. Twenty-five percent of the resulting offspring will be transgenic i.e., animals that include the exogenous genetic material within all of their cells in both alleles. 50% of the resulting animals will include the exogenous genetic material within one allele and 25% will include no exogenous genetic material.

In the microinjection method useful in the practice of the invention, the transgene is digested and purified free from any vector DNA e.g. by gel electrophoresis. It is preferred that the transgene include an operatively associated promoter that interacts with cellular proteins involved in transcription, ultimately resulting in constitutive expression. Promoters useful in this regard include those from cytomegalovirus (CMV), Moloney leukemia virus (MLV), and herpes virus, as well as those from the genes encoding metallothionein, skeletal actin, P-enolpyruvate carboxylase (PEPCK), phosphoglycerate (PGK), DHFR, and thymidine kinase. Promoters for viral long terminal repeats (LTRs) such as Rous Sarcoma Virus can also be employed. When the animals to be made transgenic are avian, preferred promoters include those for the chicken β-globin gene, chicken lysozyme gene, and avian leukosis virus. Constructs useful in plasmid transfection of embryonic stem cells will employ additional regulatory elements well known in the art such as enhancer elements to stimulate transcription, splice acceptors, termination and polyadenylation signals, and ribosome binding sites to permit translation.

Retroviral infection can also be used to introduce transgene into a non-human animal, as described above. The developing non-human embryo can be cultured in vitro to the blastocyst stage. During this time, the blastomeres can be targets for retro viral infection (Jaenich, Proc. Natl. Acad. Sci. USA 73:1260-1264, 1976). Efficient infection of the blastomeres is obtained by enzymatic treatment to remove the zona pellucida (Hogan et al., In "Manipulating the Mouse Embryo" (Cold Spring Harbor Laboratory Press, Cold Spring Harbor N.Y. 1986)). The viral vector system used to introduce the transgene is typically a replication-defective retro virus carrying the transgene (Jahner et al., Proc. Natl. Acad. Sci. USA 82:6927-6931, 1985; Van der Putten et al., Proc. Natl. Acad. Sci USA 82:6148-6152, 1985). Transfection is easily and efficiently obtained by culturing the blastomeres on a monolayer of virus-producing cells (Van der Putten, supra; Stewart, et al., EMBO J. 6:383-388, 1987). Alternatively, infection can be performed at a later stage. Virus or virus-producing cells can be injected into the blastocoele (Jahner et al., Nature 298:623-628, 1982). Most of the founders will be mosaic for the transgene since incorporation occurs only in a subset of the cells that formed the transgenic nonhuman animal. Further, the founder can contain various retroviral insertions of the transgene at different positions in the genome that generally will segregate in the offspring. In addition, it is also possible to introduce transgenes into the germ line, albeit with low efficiency, by intrauterine retroviral infection of the midgestation embryo (Jahner et al., supra, 1982).

A third type of target cell for transgene introduction is the embryonal stem cell (ES). ES cells are obtained from preimplantation embryos cultured in vitro and fused with embryos (Evans et al. Nature 292:154-156, 1981; Bradley et al., Nature 309:255-258, 1984; Gossler et al., Proc. Natl. Acad. Sci. USA 83:9065-9069, 1986; and Robertson et al., Nature 322:445-448, 1986). Transgenes can be efficiently introduced into the ES cells by DNA transfection or by retro virus-mediated transduction. Such transformed ES cells can thereafter be combined with blastocysts from a nonhuman animal. The ES cells thereafter colonize the embryo and contribute to the germ line of the resulting chimeric animal (for review see Jaenisch, Science 240:1468-1474, 1988).

The transgene can be any piece of DNA that is inserted by artifice into a cell, and becomes part of the genome of the organism (i.e., either stably integrated or as a stable extrachromosomal element) that develops from that cell. Such a transgene can include a gene that is partly or entirely heterologous (i.e., foreign) to the transgenic organism, or can represent a gene homologous to an endogenous gene of the organism. Included within this definition is a transgene created by the providing of an RNA sequence that is transcribed into DNA, then incorporated into the genome. The transgenes of the invention include DNA sequences that encode a mutant PKD1 polypeptide, for example, a polypeptide having an amino acid sequence substantially identical to SEQ ID NO:2 and having a mutation of a A88V, a W967R, a L2696R, an R2985G, an R3039C, a V3285I, a H3311R, or any combination thereof, or encoding a truncated PKD1 polypeptide ending at amino acid 3000 (also referred to herein as "W30001X", where "X" indicates STOP codon; see, also, Table 4) and include sense, antisense, and dominant negative encoding polynucleotides, which can be expressed in a transgenic non-human animal. The term "transgenic" as used herein also includes any organism whose genome has been altered by in vitro manipulation of the early embryo or fertilized egg or by any transgenic technology to induce a specific gene knockout. The term "gene knockout" as used herein, refers to the targeted disruption of a gene in vivo with complete or partial loss of function that has been achieved by any transgenic technology familiar to those in the art. In one embodiment, transgenic animals having a gene knockout are those in which the target gene has been rendered nonfunctional by an insertion targeted to the gene to be rendered non-functional by homologous recombination.

The invention also includes animals having heterozygous mutations in or partial inhibition of function or expression of a PKD1 polypeptide. One of skill in the art would readily be able to determine if a particular mutation or if an antisense molecule was able to partially inhibit PKD1 expression. For example, in vitro testing can be desirable initially by comparison with wild-type (e.g., comparison of northern blots to examine a decrease in expression). After an embryo has been microinjected, colonized with transfected embryonic stem cells or infected with a retrovirus containing the transgene (except for practice of the subject invention in avian species, which is addressed elsewhere herein), the embryo is implanted into the oviduct of a pseudopregnant female. The progeny are tested for incorporation of the transgene by Southern blot analysis of blood samples using transgene specific probes. PCR is particularly useful in this regard. Positive progeny ($P_O$) are crossbred to produce offspring ($P_1$) that are analyzed for transgene expression by northern blot analysis of tissue samples.

In order to distinguish expression of like species transgenes from expression of an endogenous PKD1-related gene, a marker gene fragment can be included in the construct in the 3' untranslated region of the transgene and the northern blot probe designed to probe for the marker gene fragment. The serum levels of a PKD1 polypeptide can also be measured in the transgenic animal to determine the level of PKD1 expression. A method of creating a transgenic organism also can include methods of inserting a transgene into, for example, an embryo of an already created transgenic organism, the organism being transgenic for a different unrelated gene or polypeptide.

Transgenic organisms of the invention are highly useful in the production of organisms for study of, for example, polycystic kidney disease or PKD1-related diseases or disorders and in identifying agents or drugs that inhibit or modulate polycystic kidney disease, PKD1 associated disorders and inheritance. Expression of a mutant human PKD1 polynucleotide can be assayed, for example, by standard northern blot analysis, and the production of the mutant human PKD1 polypeptide can be assayed, for example, by detecting its presence using an antibody directed against the mutant human PKD1 polypeptide. Those animals found to express the mutant human PKD1 polypeptide can then be observed for the development of ADPKD-like symptoms.

As discussed above, animal models of ADPKD can be produced by engineering animals containing mutations in a copy of an endogenous PKD1 gene that correspond to mutations within the human PKD1 polynucleotide. Utilizing such a strategy, a PKD1 homologue can be identified and cloned from the animal of interest, using techniques such as those described herein. One or more mutations can be engineered into such a PKD1 homologue that correspond to mutations within the human PKD1 polynucleotide, as discussed above (e.g., resulting in a mutation of the amino acid sequence as set forth in SEQ ID NO:2 and having a mutation of a A88V, a W967R, a L2696R, an R2985G, a W3001X, an R3039C, a V3285I, a H3311R, or any combination thereof; see, also, Table 4). As disclosed herein, a mutant polypeptide produced by such an engineered corresponding PKD1 homologue can exhibit an aberrant PKD1 activity that is substantially similar to that exhibited by a mutant human PKD1 protein. The engineered PKD1 homologue can then be introduced into the genome of the animal of interest, using techniques such as those described, above. Accordingly, any of the ADPKD animal models described herein can be used to test compounds for an ability to ameliorate ADPKD symptoms, including those associated with the expression of a mutant PKD1 polypeptide substantially identical to SEQ ID NO:2 and having the mutation A88V, W967R, L2696R, R2985G, W3001X, R3039C, V3285I, H3311R, or a combination thereof (see Example 2 and Table 4).

As discussed above, mutations in the PKD1 polynucleotide that cause ADPKD can produce a form of the PKD1 protein that exhibits an aberrant activity that leads to the formation of ADPKD symptoms. A variety of techniques can be utilized to inhibit the expression, synthesis, or activity of such mutant PKD1 polynucleotides and polypeptides. For example, compounds such as those identified through assays described, above, which exhibit inhibitory activity, can be used in accordance with the invention to ameliorate ADPKD symptoms. Such molecules can include, but are not limited to, small and large organic molecules, peptides, and antibodies. Further, antisense and ribozyme molecules that inhibit expression of a PKD1 polynucleotide, (e.g., a mutant PKD1 polynucleotide), can also be used to inhibit the aberrant PKD1 activity. Such techniques are described, below. In yet another embodiment, triple helix molecules can be utilized in inhibiting aberrant PKD1 activity.

Among the compounds that can exhibit anti-ADPKD activity are antisense, ribozyme, and triple helix molecules. Such molecules can be designed to reduce or inhibit mutant PKD1 activity by modulating the expression or synthesis of PKD1 polypeptides. Techniques for the production and use of such molecules are well known to those of skill in the art.

Double stranded interfering RNA molecules are especially useful to inhibit expression of a target gene. For example, double stranded RNA molecules can be injected into a target cell or organism to inhibit expression of a gene and the resultant polypeptide's activity. It has been found that such double stranded RNA molecules are more effective at inhibiting expression than either RNA strand alone (Fire et al., Nature, 19:391(6669):806-11, 1998).

When a disorder is associated with abnormal expression of a PKD1 polypeptide (e.g., overexpression, or expression of a mutated form of the protein), a therapeutic approach that directly interferes with the translation of a PKD1 polypeptide (e.g., a wild type, variant or mutant PKD1 polypeptide) is possible. Alternatively, similar methodology can be used to study gene activity. For example, antisense nucleic acid, double stranded interfering RNA or ribozymes could be used to bind to a PKD1 mRNA sequence or to cleave it. Antisense RNA or DNA molecules bind specifically with a targeted gene's RNA message, interrupting the expression of that gene's protein product. The antisense binds to the messenger RNA forming a double stranded molecule that cannot be translated by the cell. Antisense oligonucleotides of about 15 to 25 nucleotides are preferred since they are easily synthesized and have an inhibitory effect just like antisense RNA molecules. In addition, chemically reactive groups, such as iron-linked ethylenediaminetetraacetic acid (EDTA-Fe) can be attached to an antisense oligonucleotide, causing cleavage of the RNA at the site of hybridization. Antisense nucleic acids are DNA or RNA molecules that are complementary to at least a portion of a specific mRNA molecule (Weintraub, Scientific American, 262:40, 1990). In the cell, the antisense nucleic acids hybridize to the corresponding mRNA, forming a double-stranded molecule. The antisense nucleic acids interfere with the translation of the mRNA, since the cell will not translate a mRNA that is double-stranded. Antisense oligomers of at least about 15 nucleotides also are preferred because they are less likely to cause problems when introduced into the target PKD1 polypeptide producing cell. The use of antisense methods to inhibit the in vitro translation of genes is well known in the art (Marcus-Sakura, Anal. Biochem., 172:289, 1988).

Use of an oligonucleotide to stall transcription is known as the triplex strategy since the oligomer winds around double-helical DNA, forming a three-strand helix. Therefore, these triplex compounds can be designed to recognize a unique site on a chosen gene (Maher et al., Antisense Res. and Devel., 1:227, 1991; Helene, Anticancer Drug Design, 6:569, 1991).

Ribozymes are RNA molecules possessing the ability to specifically cleave other single-stranded RNA in a manner analogous to DNA restriction endonucleases. Through the modification of nucleotide sequences that encode these RNAs, it is possible to engineer molecules that recognize specific nucleotide sequences in an RNA molecule and cleave it (Cech, J. Amer. Med. Assn., 260:3030, 1988). A major advantage of this approach is that, because they are sequence-specific, only mRNAs with particular sequences are inactivated.

There are two basic types of ribozymes namely, tetrahymena-type (Hasselhoff, Nature, 334:585, 1988) and "hammerhead"-type. Tetrahymena-type ribozymes recognize sequences that are four bases in length, while "hammerhead"-type ribozymes recognize base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-base recognition sequences are preferable to shorter recognition sequences. These and other uses of antisense and ribozymes methods to inhibit the in vivo translation of genes are lnown in the art (e.g., De Mesmaeker et a/, Curr. Opin. Struct. Biol., 5:343, 1995; Gewirtz et al., Proc. Natl. Acad. Sci. USA, 93:3161, 1996b; Stein, Chem. and Biol. 3:319, 1996).

Specific ribozyme cleavage sites within any potential RNA target are initially identified by scanning the target molecule for ribozyme cleavage sites, which include the following sequence: GUA, GUU and GUC. Once identified, short RNA sequences of about 15 to 30 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using ribonuclease protection assays.

It is possible that the antisense, ribozyme, or triple helix molecules described herein can reduce or inhibit the translation of mRNA produced by mutant PKD1 alleles of the invention. In order to ensure that substantial normal levels of PKD1 activity are maintained in the cell, nucleic acid molecules that encode and express PKD1 polypeptides exhibiting normal PKD1 activity can be introduced into cells that do not contain sequences susceptible to whatever antisense, ribozyme, or triple helix treatments. Such sequences can be introduced via gene therapy methods such as those described, below. Alternatively, it can be preferable to coadminister normal PKD1 protein into the cell or tissue in order to maintain the requisite level of cellular or tissue PKD1 activity.

Antisense RNA and DNA molecules, ribozyme molecules and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well known modifications to the DNA molecules can be introduced as a means of increasing intracellular stability and half-life. Possible modifications include, but are not limited to, the addition of flanking sequences of ribonucleotide or deoxyribonucleotides to the 5' or 3' end or both of the molecule or the use of phosphorothioate or 2'-O-methyl rather than phosphodiesterase linkages within the oligodeoxyribonucleotide backbone.

As discussed above, mutations in the PKD1 polynucleotide that cause ADPKD can lower the level of expression of the PKD1 polynucleotide or; alternatively, can cause inactive or substantially inactive PKD1 proteins to be produced. In either instance, the result is an overall lower level of normal PKD1 activity in the tissues or cells in which PKD1 is normally expressed. This lower level of PKD1 activity, then, leads to ADPKD symptoms. Thus, such PKD1 mutations represent dominant loss-of-function mutations. For example, a polynucleotide having a sequence as set forth in SEQ ID NO:1 and having a mutation of a G9213A results in early termination of PKD1.

For example, normal PKD1 protein, at a level sufficient to ameliorate ADPKD symptoms can be administered to a patient exhibiting such symptoms or having a mutant PKD1 polynucleotide. Additionally, DNA sequences encoding normal PKD1 protein can be directly administered to a patient exhibiting ADPKD symptoms or administered to prevent or reduce ADPKD symptoms where they have been diagnosed as having a PKD1 mutation identified herein but have not yet demonstrated symptoms. Such administration can be at a concentration sufficient to produce a level of PKD1 protein such that ADPKD symptoms are ameliorated.

Further, subjects with these types of mutations can be treated by gene replacement therapy. A copy of the normal PKD1 polynucleotide can be inserted into cells, renal cells, for example, using viral or non-viral vectors that include, but are not limited to vectors derived from, for example, retroviruses, vaccinia virus, adeno-associated virus, herpes viruses, bovine papilloma virus or non-viral vectors, such as plasmids. In addition, techniques frequently employed by those skilled in the art for introducing DNA into mammalian cells can be utilized. For example, methods including but not limited to electroporation, DEAE-dextran mediated DNA transfer, DNA guns, liposomes, direct injection, and the like can be utilized to transfer recombinant vectors into host cells. Alternatively, the DNA can be transferred into cells through conjugation to proteins that are normally targeted to the inside of a cell. For example, the DNA can be conjugated to viral proteins that normally target viral particles into the targeted host cell.

Administering the whole gene or polypeptide is not necessary to avoid the appearance of ADPKD symptoms. The use of a "minigene" therapy approach also can serve to ameliorate such ADPKD symptoms (see Ragot et al., Nature 3:647, 1993; Dunckley et al., Hum. Mol. Genet. 2:717-723, 1993). A minigene system uses a portion of the PKD1 coding region that encodes a partial, yet active or substantially active PKD1 polypeptide. As used herein, "substantially active" means that the polypeptide serves to ameliorate ADPKD symptoms. Thus, the minigene system utilizes only that portion of the normal PKD1 polynucleotide that encodes a portion of the PKD1 polypeptide capable of ameliorating ADPKD symptoms, and can, therefore represent an effective and even more efficient ADPKD therapy than full-length gene therapy approaches. Such a minigene can be inserted into cells and utilized via the procedures described, above, for full-length gene replacement. The cells into which the PKD1 minigene are to be introduced are, preferably, those cells, such as renal cells, which are affected by ADPKD. Alternatively, any suitable cell can be transfected with a PKD1 minigene so long as the minigene is expressed in a sustained, stable fashion and produces a polypeptide that ameliorates ADPKD symptoms.

A therapeutic minigene for the amelioration of ADPKD symptoms can comprise a nucleotide sequence that encodes at least one PKD1 polypeptide peptide domain, particularly a domain having an amino acid sequence substantially identical to a peptide portion SEQ ID NO:2 and having a mutation as shown in Table 4, for example, an A88V, W967R, L2696R, R2985G, W3001X, R3039C, V3285I, or H3311R mutation. Minigenes that encode such PKD1 polypeptides can be synthesized and/or engineered using the PKD1 polynucleotide sequence (SEQ ID NO:1).

The materials for use in the assay of the invention are ideally suited for the preparation of a kit. Such a kit can comprise a carrier means containing one or more container means such as vials, tubes, and the like, each of the container means comprising one of the separate elements to be used in the method. One of the container means can comprise a probe that is or can be detectably labeled. Such probe can be an oligonucleotide comprising at least 10 contiguous nucleotides and having a sequence of a fragment of SEQ ID NO:1 including: nucleotide 474, wherein nucleotide 474 is a T; nucleotide 487, wherein nucleotide 487 is an A; nucleotide 3110, wherein nucleotide 3110 is a C; nucleotide 8298, wherein nucleotide 8298 is a G; nucleotide 9164, wherein nucleotide 9164 is a G; nucleotide 9213, wherein nucleotide 9213 is an A; nucleotide 9326, wherein nucleotide 9326 is a T; nucleotide 9367, wherein nucleotide 9367 is a T; nucleotide 10064, wherein nucleotide 10064 is an A; nucleotide 10143, wherein nucleotide 10143 is a G; nucleotide 10234, wherein nucleotide 10234 is a C; or nucleotide 10255, wherein nucleotide 10255 is a T (see, also, Example 2).

A kit containing one or more oligonucleotide probes of the invention can be useful, for example, for qualitatively identifying the presence of mutant PKD1 polynucleotide sequences in a sample, as well as for quantifying the degree of binding of the probe for determining the occurrence of specific strongly binding (hybridizing) sequences, thus indicating the likelihood for a subject having or predisposed to a disorder associated with PKD1. Where the kit utilizes nucleic acid hybridization to detect the target nucleic acid, the kit can also have containers containing reagents for amplification of the target nucleic acid sequence. When it is desirable to amplify the mutant target sequence, this can be accomplished using oligonucleotide primers, which are based upon identification of the flanking regions contiguous with the target nucleotide sequence. For example, primers such as those listed below in Tables 1 and 2 can be included in the kits of the invention. The kit can also contain a container comprising a reporter means such as an enzymatic, fluorescent, or radionuclide label, which can be bound to or incorporated into the oligonucleotide and can facilitate identification of the oligonucleotide.

The following examples are intended to illustrate but not limit the invention.

EXAMPLES

The present invention is based upon the use of widely spaced PKD1-specific anchor primers in long range PCR to generate 5 kb to 10 kb PKD1 polynucleotide segments. After appropriate dilution, the PCR products can be used as a template for mutation screening using any one of a variety of methods. Accordingly, a number of mutants have been identified in families with PKD1-associated disorders.

Using a number of PKD1-specific primers, eight templates ranging in size from about 0.3 to 5.8 kb were generated that span from the 5' untranslated region to intron 34 and cover all exons in the replicated region including exon 1 and exon 22 (Example 1). These reagents were used to evaluate 47 Asian PKD1 families (Example 2). Variant nucleotide sequences were found throughout the PKD1 polynucleotide sequence.

Forty-one Thai and 6 Korean ADPKD families were studied. Samples from 50 healthy Thai blood donors collected in blood banks served as normal controls. Genomic DNA was extracted from either fresh or frozen whole blood that had been stored for up to five years using commercially available kits (Puregene, Gentra) or standard phenol-chloroform methods. For the N23HA and 145.19 cell lines (Cell 77:881-894, 1994; Germino et al., Am J. Hum. Genet. 46:925-933, 1990; Ceccherini et al., Proc. Natl. Acad. Sci. USA 89:104-108, 1992, each of which is incorporated herein by reference; see, also, Watnick et al., supra, 1997), genomic DNA was isolated using the Puregene DNA isolation kit.

Example 1

Long Range Specific Templates

A two-part strategy was used to generate and validate PKD1-specific primers that could be used to amplify the replicated portion of PKD1. The sequence of PKD1 (SEQ ID NO:1) was aligned with that of two homologues present in GenBank (Accession Number AC002039) and identified potential sequence differences. Candidate primers were designed such that the mismatches were positioned at or adjacent to the 3' end of the oligonucleotide so as to maximize their specificity for PKD1.

Figure 2:
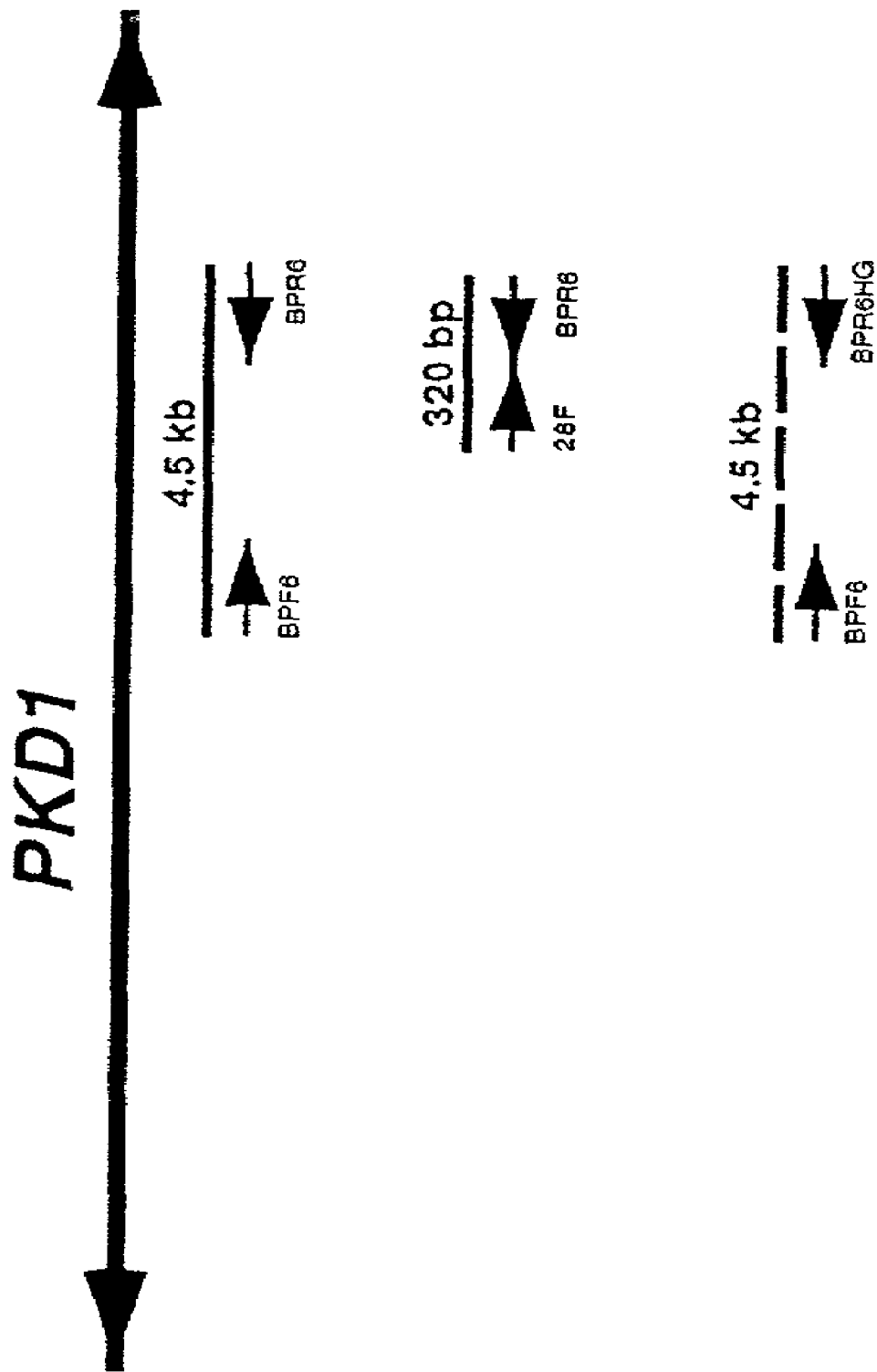
FIG. 2 shows the relative position of the BPF6-BPR6 long-range PCR template and the much shorter PKD1-specific exon 28 product, 28F-BPR6. The dashed line below exon 28 identified the long range PCR amplification product that resulted when BPF6, the sequence of which is common to the PKD1 gene and to the homologs, was used in combination with the homolog-specific primer, BPR6HG.

The primers were tested for specificity using rodent-human somatic cell hybrids that either contained only human 16p13.3 and therefore, human PKD1 (145.19, a radiation hybrid), or that lacked 16p13.3 and contained only the human PKD1-homologues (N23HA). FIG. 2 presents a representative example of this approach using the primer pair, BPF6 and the PKD1-specific primer BPR6. This primer pair amplified a product of the correct length (4.5 kb) under the stated conditions only when total human genomic DNA or 145.19 DNA is used as template. Similar results were obtained when BPR6 was used in combination with the non-specific primer 28F to generate a much shorter product.

As a final control, the absence of amplified product was verified using N23HA as template to confirm that the results obtained using total human genomic DNA and 145.19 DNA were due to the specificity of the primer and not the result of other causes (i.e., difference in quality of DNA or ratio of human/rodent template). A primer specific for the homologues (BPR6HG) was designed that was positioned the same distance from BPF6 as BPR6 and used to amplify a specific band of the same size as the corresponding PKD1-long range product. As predicted, a product of the correct size was amplified from both N23HA and total genomic DNA, but not from 145.19.

A total of eight primer pairs can be used to generate a series of templates that range in size from about 0.3 kb to 5.8 kb and include all exons and their flanking intron sequences in the replicated portion of PKD1 (exons 1 to 34). Table 1 summarizes the details for each product and includes the sequence of each primer, its respective position within the gene, its expected size, and the optimal annealing temperature and extension time for its amplification. FIG. 1 illustrates the relative position of each product with respect to the overall gene structure. It should be noted that exon 1 and its flanking sequences were particularly problematic to evaluate. Primer design was greatly limited by the high degree of homology and extreme GC bias in the region. A combination of widely space primers (to generate a fragment considerably larger than the segment of interest) and the GC melt system were used to circumvent these obstacles.

Specific details concerning the primer sequences, annealing temperatures and extension times used for each long-range (LR) template are provided in Table 1 (all sequences in Tables 1 and 2 are shown in 5' to 3' orientation from left to right). Three hundred to 400 ng of genomic DNA was used as template for each LR product, except for exon 1 (see below). The long range PCR amplification was performed as follows in a Perkin Elmer 9600 thermal cycler: denaturation at 95° C. for 3 min followed by 35 cycles of a two-step protocol that included denaturation at 95° C. for 20 sec followed by annealing and extension at a temperature and for a time specific for each primer pair (Table 1). A final extension at 72° C. for 10 min was included in each program. The total PCR volume was 50 µl using 4 U of rtth DNA polymerase XL (Cetus, Perkin Elmer) and a final MgOAC$_2$ concentration of 0.9 mM. A hot start protocol as

TABLE 1

Oligonucleotide primers for Long-range specific templates from exon 1-34 of PKD1 gene

| Template | Primers | Sequence 5'→3' | Position (5') | Size (kb) | Tm (° C.) | ET (Min) | SEQ ID NO: |
|---|---|---|---|---|---|---|---|
| T1 | BPF14* | CCATCCACCTGCTGTGTGACCTGGTAAAT | 2043 | 2.2 | 69 | 7 | 3 |
|  | BPR9 | CCACCTCATCGCCCCTTCCTAAGCAT | 4290 |  |  | 7 | 4 |
| T2-7 | BPF9* | ATTTTTTGAGATGGAGCTTCACTCTTGCAGG | 17907 | 4.6 | 68 | 7 | 5 |
|  | BPR4 | CGCTCGGCAGGCCCCTAACC | 22489 |  |  |  | 6 |
| T8-12 | BPF12 | CCGCCCCCAGGAGCCTAGACG | 22218 | 4.2 | 68 | 7 | 7 |
|  | BPR5* | CATCCTGTTCATCCGCTCCACGGTTAC | 26363 |  |  |  | 8 |
| T13-15 | F13 | TGGAGGGAGGGACGCCAATC | 26246 | 4.4 | 68 | 7 | 9 |
|  | R27* | GTCAACGTGGGCCTCCAAGT | 30612 |  |  |  | 10 |
| T15-21 | F26* | AGCGCAACTACTTGGAGGCCC | 30603 | 3.4 | 70 | 4.5 | 11 |
|  | R2 | GCAGGGTGAGCAGGTGGGGCCATCCTAC | 33953 |  |  |  | 12 |
| T22 | BPF15 | GAGGCTGTGGGGGTCCAGTCAAGTGG | 36815 | 0.3 | 72 | 1 | 13 |
|  | BPR12* | AGGGAGGCAGAGGAAAGGGCCGAAC | 37136 |  |  |  | 14 |
| T23-28 | BPF6 | CCCCGTCCTCCCCGTCCTTTTGTC | 37325 | 4.2 | 69 | 7 | 15 |
|  | BPR6* | AAGCGCAAAAGGGCTGCGTCG | 41524 |  |  |  | 16 |
| T29-34 | BPF13* | GGCCCTCCCTGCCTTCTAGGCG | 41504 | 5.8 | 68 | 8 | 17 |
|  | KG8R25* | GTTGCAGCCAAGCCCATGTTA | 47316 |  |  |  | 18 |

Tm—annealing temperature;
ET—extension time;
*—PKD1-specific primer.
Bold type in BPR12 primer sequence identifies intentional replacement of C by A to enhance discrimination of PKD1 from homologs.

recommended by the manufacturer was used for the first cycle of amplification. For the exon 1 LR product (T1), the LR was generated using 500 ng of genomic DNA. The long range PCR amplification was modified as follows: denaturation 95° C. for 1 min followed by 35 two-step cycles of denaturation at 95° C. for 30 sec followed by annealing and extension at 69° C. for 7 min. The total PCR volume was 50 µl using 1 µl of Advantage-GC genomic polymerase (Clontech), GC melt of 1.5 M and final MgOAC$_2$ concentration of 1.1 mM.

The long-range templates were serially diluted (1:10$^4$ or 1:10$^5$) to remove genomic contamination, then used as templates for nested PCR of 200-400 bp exonic fragments. A total of 17 new primer pairs were developed for exons 1-12 and exon 22. The sequences and PCR conditions for each new pair are summarized in Table 2. Primer sequences and PCR conditions for exons 13-21 and 23-34 are described in Watnick et al., Am. J. Hum. Genet. 65:1561-1571, 1999; and Watnick et al., Hum. Mol. Genet. 6:1473-1481, 1997, which are incorporated herein by reference. Intron based primers were positioned approximately 30-50 bp away from consensus splice sites. Exons larger than approximately 400 bp were split into overlapping fragments of less than or equal to 350 bp. Two µl of diluted long range (LR) product was used as template for amplification of each exon. Single strand conformation analysis was performed using standard protocols. SSCA analysis was performed by use of 8% polyacrylamide gels with 5% glycerol added. The radiolabeled PCR products were diluted with loading buffer, were denatured by heating at 95° C. for 5 min, then were placed on ice prior to being loaded and run on the gel at room temperature. Gels were run at 400 V overnight, dried, and placed on X-Omat XAR film (Kodak) at room temperature. Aberrantly migrating bands detected by SSCA were cut from the gel and eluted into 100 µl of sterile water overnight. The eluted products were re-amplified using the same set of primers, purified using Centricon-100 columns (Amicon) and then sequences.

TABLE 2

Nested Primers Used for Mutation Detection

| Exons | Primer | Primer Sequence 5' 3' | Fragment Size (bp) | $T_m$ (° C.) | SEQ ID NO: |
|---|---|---|---|---|---|
| T1 | 1F1 | GGTCGCGCTGTGGCGAAGG | 328 | 67 | 19 |
| T1 | 1R1 | CGGCGGGCGGCATCGT |  |  | 20 |

TABLE 2-continued

Nested Primers Used for Mutation Detection

| Exons | Primer | Primer Sequence 5' 3' | Fragment Size (bp) | T$_m$(° C.) | SEQ ID NO: |
|---|---|---|---|---|---|
| T1 | 1F2 | ACGGCGGGGCCATGCG | 348 | 67 | 21 |
| T1 | 1R2 | GCGTCCTGGCCCGCGTCC | | | 22 |
| T2-7 | 2F | TTGGGGATGCTGGCAATGTG | 272 | 62 | 23 |
| T2-7 | 2R | GGGATTCGGCAAAGCTGATG | | | 24 |
| T2-7 | 3F | CCATCAGCTTTGCCGAATCC | 171 | 62 | 25 |
| T2-7 | 3R | AGGGCAGAAGGGATATTGGG | | | 26 |
| T2-7 | 4F | AGACCCTTCCCACCAGACCT | 299 | 62 | 27 |
| T2-7 | 4R | TGAGCCCTGCCCAGTGTCT | | | 28 |
| T2-7 | 5F1 | GAGCCAGGAGGAGCAGAACCC | 259 | 65 | 29 |
| T2-7 | 5R1 | AGAGGGACAGGCAGGCAAAGG | | | 30 |
| T2-7 | 5F2 | CCCAGCCCTCCAGTGCCT | 284 | 65 | 31 |
| T2-7 | 5R2 | CCCAGGCAGCACATAGCGAT | | | 32 |
| T2-7 | 5F3 | CCGAGGTGGATGCCGCTG | 294 | 65 | 33 |
| T2-7 | 5R3 | GAAGGGGAGTGGGCAGCAGAC | | | 34 |
| T2-7 | 6F | CACTGACCGTTGACACCCTCG | 281 | 65 | 35 |
| T2-7 | 6R | TGCCCCAGTGCTTCAGAGATC | | | 36 |
| T2-7 | 7F | GGAGTGCCCTGAGCCCCCT | 311 | 65 | 37 |
| T2-7 | 7R | CCCCTAACCACAGCCAGCG | | | 38 |
| T8-12 | 8F | TCTGTTCGTCCTGGTGTCCTG | 215 | 65 | 39 |
| T8-12 | 8R | GCAGGAGGGCAGGTTGTAGAA | | | 40 |
| T8-12 | 9F | GGTAGGGGGAGTCTGGGCTT | 253 | 65 | 41 |
| T8-12 | 9R | GAGGCCACCCCGAGTCC | | | 42 |
| T8-12 | 10F | GTTGGGCATCTCTGACGGTG | 364 | 65 | 43 |
| T8-12 | 10R | GGAAGGTGGCCTGAGGAGAT | | | 44 |
| T8-12 | 11F2 | GGGGTCCACGGGCCATG | 311 | 67 | 45 |
| T8-12 | 11R2 | AAGCCCAGCAGCACGGTGAG | | | 46 |
| T8-12 | 11midF | GCTTGCAGCCACGGAAC | 386 | 65 | 47 |
| T8-12 | 11midR | GCAGTGCTACCACTGAGAAC | | | 48 |
| T8-12 | 11F1 | TGCCCCTGGGAGACCAACGATAC | 303 | 67 | 49 |
| T8-12 | 11R1 | GGCTGCTGCCCTCACTGGGAAG | | | 50 |
| 12 | 12F | GAGGCGACAGGCTAAGGG | 286 | 64 | 51 |
| | 12R-2 | CATGAAGCAGAGCAGAAGG | | | 61 |
| 13 | 13F: | TGGAGGGAGGGACGCCAATC | 308 | 67 | 62 |
| | 13R: | GAGGCTGGGGCTGGGACAA | | | 63 |
| 14 | 14F: | CCCGGTTCACTCACTGCG | 220 | 64 | 64 |
| | 14R: | CCGTGCTCAGAGCCTGAAAG | | | 65 |

TABLE 2-continued

Nested Primers Used for Mutation Detection

| Exons | Primer | Primer Sequence 5' 3' | Fragment Size (bp) | $T_m$ (° C.) | SEQ ID NO: |
|---|---|---|---|---|---|
| 15 | 15F16: | CGGGTGGGGAGCAGGTGG | 280 | 67 | 66 |
|  | 15R16: | GCTCTGGGTCAGGACAGGGGA |  |  | 67 |
| 15 | 15F15: | CGCCTGGGGGTGTTCTTT | 270 | 64 | 68 |
|  | 15R15: | ACGTGATGTTGTCGCCCG |  |  | 69 |
| 15 | 15F14: | GCCCCCGTGGTGGTCAGC | 250 | 67 | 70 |
|  | 15R14: | CAGGCTGCGTGGGGATGC |  |  | 71 |
| 15 | 15F13: | CTGGAGGTGCTGCGCGTT | 256 | 67 | 72 |
|  | 15R13: | CTGGCTCCACGCAGATGC |  |  | 73 |
| 15 | 15F12: | CGTGAACAGGGCGCATTA | 270 | 65 | 74 |
|  | 15R12: | GCAGCAGAGATGTTGTTGGAC |  |  | 75 |
| 15 | 15F11: | CCAGGCTCCTATCTTGTGACA | 259 | 60 | 76 |
|  | 15R11: | TGAAGTCACCTGTGCTGTTGT |  |  | 77 |
| 15 | 15F10: | CTACCTGTGGGATCTGGGG | 217 | 67 | 78 |
|  | 15R10: | TGCTGAAGCTCACGCTCC |  |  | 79 |
| 15 | 15F9: | GGGCTCGTCGTCAATGCAAG | 267 | 67 | 80 |
|  | 15R9: | CACCACCTGCAGCCCCTCTA |  |  | 81 |
| 15 | 15F8: | 5CCGCCCAGGACAGCATCTTC | 261 | 64 | 82 |
|  | 15R8: | CGCTGCCCAGCATGTTGG |  |  | 83 |
| 15 | 15F7: | CGGCAAAGGCTTCTCGCTC | 288 | 64 | 84 |
|  | 15R7: | CCGGGTGTGGGGAAGCTATG |  |  | 85 |
| 15 | 15F6: | CGAGCCATTTACCACCCATAG | 231 | 65 | 86 |
|  | 15R6: | GCCCAGCACCAGCTCACAT |  |  | 87 |
| 15 | 15F5: | CCACGGGCACCAATGTGAG | 251 | 64 | 88 |
|  | 15R5: | GGCAGCCAGCAGGATCTGAA |  |  | 89 |
| 15 | 15F4: | CAGCAGCAAGGTGGTGGC | 333 | 67 | 90 |
|  | 15R4: | GCGTAGGCGACCCGAGAG |  |  | 91 |
| 15 | 15F3: | ACGGGCACTGAGAGGAACTTC | 206 | 64 | 92 |
|  | 15R3: | ACCAGCGTGCGGTTCTCACT |  |  | 93 |
| 15 | 15F2: | GCCGCGACGTCACCTACAC | 265 | 67 | 94 |
|  | 15R2: | TCGGCCCTGGGCTCATCT |  |  | 95 |
| 15 | 15F1: | GTCGCCAGGGCAGGACACAG | 228 | 68 | 96 |
|  | R27': | AGGTCAACGTGGGCCTCCAA |  |  | 113 |
| 15 | 15F1-1: | ACTTGGAGGCCCACGTTGACC | 276 | 69 | 97 |
|  | 15R1-1: | TGATGGGCACCAGGCGCTC |  |  | 98 |
| 15 | 15F1-2: | CATCCAGGCCAATGTGACGGT | 266 | 64 | 99 |
|  | 15R1-2: | CCTGGTGGCAAGCTGGGTGTT |  |  | 100 |

TABLE 2-continued

Nested Primers Used for Mutation Detection

| Exons | Primer | Primer Sequence 5' 3' | Fragment Size (bp) | $T_m$ (° C.) | SEQ ID NO: |
|---|---|---|---|---|---|
| 16 | 16F: | TAAAACTGGATGGGGCTCTC | 294 | 56 | 101 |
|  | 16R: | GGCCTCCACCAGCACTAA |  |  | 102 |
| 17 | 17F: | GGGTCCCCCAGTCCTTCCAG | 244 | 67 | 103 |
|  | 17R: | TCCCCAGCCCGCCCACA |  |  | 104 |
| 18 | 18F: | GCCCCCTCACCACCCCTTCT | 342 | 67 | 105 |
|  | 18R: | TCCCGCTGCTCCCCCCAC |  |  | 106 |
| 19 | 19F: | GATGCCGTGGGGACCGTC | 285 | 67 | 107 |
|  | 19R: | GTGAGCAGGTGGCAGTCTCG |  |  | 108 |
| 20 | 20F: | CCACCCCCTCTGCTCGTAGGT | 232 | 64 | 109 |
|  | 20R: | GGTCCCAAGCACGCATGCA |  |  | 110 |
| 21 | 21F: | TGCCGGCCTCCTGCGCTGCTGA | 232 | 67 | 111 |
|  | TWR2-1: | GTAGGATGGCCCCACCTGCTCACCCTGC |  |  | 112 |

Variants that were predicted to alter a restriction site were confirmed by restriction enzyme digestion analysis of re-amplified products. In cases where the change did not alter a restriction site, primers were designed with mismatches that create a new restriction site when combined with the point mutation in question. The following primer combinations were utilized:

ASP1 + 26R (ASP1; 5'-CTGGTGACCTACATGGTCATGGCC GAGATC-3'; SEQ ID NO:55);

ASP2 + 30R (ASP2; 5'-GGTTGTCTATCCCGTCTACCTGGCCCTCCT-3'; SEQ ID NO:56);

ASP3 + 30F (ASP3; 5'-GTCCCCAGCCCCAGCCCACCTGGCC-3'; SEQ ID NO:57).

When possible, segregation of the variant with the disease phenotype was tested. In cases where a missense change was unable to be determined on the normal haplotype (and thus be a normal variant) the mutation was tested for in a panel of 50 normal controls.

Example 2

Mutation Screening

The new PKD1-specific products were generated from one affected member of each of the 47 Asian families and then used as template for mutation detection of exons 1-12 and 22-34. Table 2 (above) lists the sequence and PCR condition for primer pairs that were used for nested amplification of individual exons and their adjacent intronic sequence. Overlapping pairs were designed for segments >400 base pairs in length.

A total of 13 novel variants were detected by SSCA using the conditions described above. Two are highly likely to be pathogenic mutations, four are predicted to encode missense substitutions not found in normals and seven are normal variants (see Table 3).

The first pathogenic mutation is a G to A transition at position 9213 in exon 25 that is predicted to result in a nonsense codon (W3001X). Its presence was confirmed by restriction analysis using the enzyme Mae I and it was found to segregate with disease. This variant is predicted to truncate the protein near the carboxyl end of the Receptor for Egg Jelly (REJ) domain. The W3001X mutation results in a greatly truncated product missing all of the membrane spanning elements, intervening loops and carboxy terminus. The second mutation (T3110C) is predicted to result in a non-conservative amino acid substitution (W967R) at a critical position of one of the PKD repeats. The mutation is unique to the family in which it was found and was not observed in a screen of over 100 normal Thai chromosomes. The W967R missense mutation is predicted to disrupt the secondary structure of PKD domain 3. The WDFGDGS (SEQ ID NO:58) motif within the CC' loop region is the most conserved sequence of the PKD domains. The tryptophan is replaced is the first residue of the turn at the end of the C strand and is conserved in 14 out of 16 PKD domains. Moreover, it is evolutionarily conserved in mouse and Fugu polycystin-1.

TABLE 3

Mutations Identified in the PKD1 Gene in a Thai population

| Patient | Exon | Nucleic Acid Change | Codon Change | Consequence | Confirmation Enzyme |
|---|---|---|---|---|---|
| Pathogenic | | | | | |
| RAMA28-01[0] | 12 | T3110C | W967R | Missense (disrupt PKD domain3) | BsaW 1 (cut NC) |
| RAMA59-02* | 25 | G9213A | W3001X | Nonsense (early termination) | Mae I |
| Variants not found in 100 chromosomes | | | | | |
| RAMA3-02* | 22 | T8298G | L2696R | Missense | HinP1 I |
| RAMA87-01* | 25 | A9164G | R2985G | Missense | BsrB 1 |
| RAMA87-01* | 25 | C9326T | R3039C | Missense | Fau I (cut NC) |
| RAMA45-03* | 29 | G10064A | V3285I | Missense | Bsm I |
| Probable normal variants | | | | | |
| RAMA7-06 | 2 | C474T | A88V | Missense | Hph I |
| RAMA107-01 | 2 | G487A | A92A | Silent change | TspR I |
| RAMA94-01 | 25 | C9367T | G3052G | Silent change | Sfo I (cut NC) |
| RAM466-01 | 30 | A10143G[HG] | H3311R | Missense | Nsp I (cut NC) |
| RAMA66-01 | 30 | T10234C[HG] | L3341L | Silent change | ASP1 + BseR I |
| RAMA51-01 | 30 | G10255T | R3348R | Silent change | ASP2 + MSC I |

*—Segregation with disease;
[0]—cannot test for segregation;
NC—Normal control;
[HG]—Present in one copy of the homologues;
ASP—Allele-specific primer.

These pathogenic mutations add to previously identified pathogenic mutations, including a deletion of G3336 (ΔG3336) in exon 13, resulting in a frame shift after amino acid 1041 (FS1041); C4168T (Q1653)X), C6089T (Q1960X) and C6326T (Q2039X) mutations in exon 15, each resulting in a nonsense termination; ΔG7205-G7211 in exon 16, resulting in a FS2331; a C7415T (R2402X) mutation in exon 18, resulting in a nonsense termination; a C7883T (Q2558X) mutation in exon 19, resulting in a nonsense termination; and a ΔC8159-T8160 mutation in exon 21, resulting in a FS2649 (Phakdeekitcharoen et al., supra, 2000). In addition, probable pathogenic mutations including G3707A (G1166S) and T6078A (V1956E) missense mutations in exon 15, and a C7433T (R2408C) missense mutation and an insertion of a GCG trinucleotide between G7535 and G7536 (extra Gly2422) in exon 18 have been identified (Phakdeekitcharoen et al., supra, 2000).

Four additional mutations unique to one of the families also were identified (see Table 3). The mutants segregate with disease, and were not observed in a screen of over 100 normal Thai chromosomes. Three of the four variants are predicted to result in non-conservative amino acid substitutions. Two of them (A9164G, C9326T) are present in the same allele of a single family (RAAM87). As such, these mutations meet several criteria expected of disease-producing mutations, including they are not found in normal, ethnically matched chromosomes, they segregate with the disease, and they result in non-conservative substitutions.

In one case a heteroduplex pattern was discovered for the exon 22 product of the proband by standard agarose electrophoresis. The heteroduplex pattern was confirmed to segregate with disease and subsequently determined that the novel variant was the result of a T to G transversion at position 8298. This mutation is predicted to substitute arginine for leucine at position 2696 of the protein sequence. This non-conservative substitution is within the REJ domain. Interestingly, the R3039C substitution occurs near a newly described putative proteolytic cleavage site of polycystin-1, His(3047)-Leu-Thr-Ala(3050) (SEQ ID NO:59). In the corresponding position of Fugu and murine polycystin-1, glutamic acid and arginine, respectively, are present, suggesting a non-critical role for a non-polar residue at this location.

Seven nucleotide substitutions that are likely normal variants were also identified. Two are missense variants that do not segregate with disease in the family in which they were discovered. The C474T substitution results in the conservative replacement of valine by alanine at position 88 in the first leucine rich (LRR) repeat. The amino acid is not conserved between species and is not predicted to disrupt the LRR structure. The second missense variant, A10143G, substitutes arginine for histidine at position 3311 within the first extracellular loop between TM2 and TM3. It too, is a conservative change involving a residue whose identity is not evolutionarily conserved at this position. The other five variants were silent nucleotide substitutions that were unique to the pedigree in which they were found and not found in more than 100 normal chromosomes. It is possible that these variants can be pathogenic by affecting gene splicing in the region. Two of the normal variants of exon 30, A10143G (H3311R) and T10234C (L3341L), were clustered together in a single PKD1 haplotype. Interestingly, both variants also are present in at least one of the homologues, suggesting a previous gene conversion event as the original of these PKD1 variants. Additional PKD1 variants, which do not appear to be associated with a PKD1-associated disorder, include two silent mutations, G4885A (T1558T) and C6058T (S1949S), and a missense mutation, G6195A (R1995H), in exon 15; a silent T7376C (L2389L) mutation in exon 17; a silent C7696T (C2495C) mutation in exon 18; and a missense G8021A (D2604N) mutation in exon 20 (Phakdeekitcharoen et al., supra, 2000).

Table 4 summarizes the clinical findings for the probands of 17 Thai families. The genotypes and phenotypes for patients with ADPKD are shown. It has been estimated on the basis of studies of Caucasian populations that approximately 15% of mutations are localized to the nonreplicated portion of the PKD1 gene. If the same frequency is true for the Thai population (the patients were not screened for mutations in the nonreiterated portion), then the present studies have identified approximately 45% to 54 percent of all mutations present in the nonreplicated region. This detection rate likely can be increased by using more sensitive detection methods such as DHPLC (Kristensen et al., supra, 2001), HTCSGD (Leung et al., supra, 2001), or the like.

TABLE 4

Genotypes and phenotypes in Thai ADPKD1

| Patients | Age | Exon | Genotype | | Renal insuff. HT (Cr > 2) | Renal stone | Phenotype | | | | Ref. |
| | | | Codon Change | Consequence | | | Palpable kidneys | Liver Cyst | Heart Valv. Abnorm. | Brain Aneur. | |
| --- | --- | --- | --- | --- | --- | --- | --- | --- | --- | --- | --- |
| RAMA28-0 | 30 | 12 | W967R | Missense | + | − | − | − | − | − | − | |
| RAMA103- | 57 | 13 | FS after 1041 | Frameshift | + | − | + | − | + | − | − | (*) |
| RAMA49-0 | 26 | 15 | G1166S | Missense | + | − | − | + | − | − | − | (*) |
| RAMA36-0 | 47 | 15 | Q1653X | Nonsense | + | − | − | + | − | − | − | (*) |
| RAMA108- | 57 | 15 | V1956E | Missense | + | + | − | − | − | − | − | (*) |
| RAMA77-0 | 53 | 15 | Q1960X | Nonsense | + | + | − | + | + | − | − | (*) |
| RAMA32-0 | 36 | 15 | Q2039X | Nonsense | + | + | − | + | − | − | − | (*) |
| RAMA97-0 | 45 | 17 | R2402X | Nonsense | + | + | − | − | − | − | − | (*) |
| RAMA96-0 | 30 | 18 | R2408C | Missense | − | − | + | − | + | − | − | (*) |
| RAMA99-0 | 56 | 18 | R2430X | Nonsense | + | + | + | − | + | − | − | (*) |
| RAMA66-0 | 39 | 18 | 2442 add'l. Gly | Extra Glycine | + | − | + | − | − | − | − | (*) |
| RAMA55-0 | 52 | 19 | Q2558X | Nonsense | − | − | − | + | + | − | − | (*) |
| RAMA5-01 | 53 | 21 | FS after 2649 | Frameshift | + | + | + | + | + | + | + | (*) |
| RAMA3-02 | 40 | 22 | L2696R | Missense | + | + | − | + | + | − | − | |
| RAMA87-0 | 61 | 25 | R2985G | Missense | − | − | − | + | + | − | − | |
| | | 25 | R3039C | Missense | | | | | | | | |
| RAMA59-0 | 35 | 25 | W3001X | Nonsense | + | + | + | − | − | − | − | |
| RAMA45-0 | 59 | 29 | V3285I | Missense | + | + | − | − | − | − | − | |

HT—hypertension;
Renal insuff.—renal insufficiency;
Heart Valv. Abnorm.—heart valvular abnormalities;
Brain Aneur.—brain aneurisyms;
*—Phakdeekitcharoen et al., supra, 2000.

Although the invention has been described with reference to the above examples, it will be understood that modifications and variations are encompassed within the spirit and scope of the invention. Accordingly, the invention is limited only by the following claims.

What is claimed is:

1. A set of primers, wherein primers in the set selectively hybridize under highly stringent conditions to a nucleotide sequence within one of the polycystic kidney disease-associated protein-1 (PKD1) gene sequences set forth as:
nucleotides 2043 to 4290 of SEQ ID NO:1,
nucleotides 17907 to 22489 of SEQ ID NO:1,
nucleotides 22218 to 26363 of SEQ ID NO:1,
nucleotides 26246 to 30615 of SEQ ID NO:1,
nucleotides 30606 to 33957 of SEQ ID NO:1,
nucleotides 36819 to 37140 of SEQ ID NO:1
nucleotides 37329 to 41258 of SEQ ID NO:1, and
nucleotides 41508 to 47320 of SEQ ID NO:1,
or to a nucleotide sequence complementary thereto, wherein each of the primers comprises a 5' region and adjacent 3' region,
the 5' region comprising a nucleotide sequence that selectively hybridizes to a PKD1 gene sequence as set forth in SEQ ID NO:1, wherein the 5' region comprises at least ten contiguous nucleotides, and
the 3' region comprising a nucleotide sequence that selectively hybridizes to a PKD1 gene sequence as set forth in SEQ ID NO:1,
provided the primer does not consist of a sequence as set forth in SEQ ID NO:11, SEQ ID NO:18, SEQ ID NO:52, or SEQ ID NO:60;
wherein the primers amplify at least a first and a second amplification product, and wherein at least one of the primers for the first amplification product consists of SEQ ID NO: 3.

2. A solid matrix, comprising the set of primers of claim 1, wherein each of the primers is immobilized on the solid matrix.

3. The solid matrix of claim 2, wherein the solid matrix is a microchip.

4. The set of primers of claim 1, wherein a second primer for the first amplification product are selected from the group consisting of SEQ ID NOs: 4 and 6.

5. The set of primers of claim 1, wherein the primers for the second amplification product are selected from the group consisting of SEQ ID NOs: 19, 20, 21, and 22.

6. The set of primers of claim 1, wherein said set of primers selectively hybridize to SEQ ID NO: 1 and amplify portions of SEQ ID NO: 1 comprising about 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320, or to a nucleotide sequence complementary to said sequence of SEQ ID NO: 1.

7. The set of primers of claim 6, wherein said set of primers comprises SEQ ID NO: 3 and 4; SEQ ID NO: 5 and 6; SEQ ID NO: 7 and 8; SEQ ID NO: 9 and 10; SEQ ID NO: 11 and 12; SEQ ID NO: 13 and 14; SEQ ID NO: 15 and 16; and SEQ ID NO: 17 and 18.

8. A method of detecting the presence or absence of a mutation in a PKD1 polynucleotide in a sample, the method comprising:
contacting nucleic acid molecules in a sample with a first set of primer pairs to amplify a first amplification product, wherein at least one of the primers for the first amplification product consists of SEQ ID NO: 3, wherein the first set of primer pairs selectively hybridize under highly stringent conditions to a PKD1 polynucleotide comprising SEQ ID NO: 1; and
contacting the first amplification product with a second set of primer pairs to amplify a second amplification product, and wherein the second set of primer pairs selectively hybridize under highly stringent conditions to the first amplification product; and
identifying the presence or absence of a mutation in the second amplification product, thereby detecting the presence or absence of a mutation in the PKD1 polynucleotide in the sample, wherein the mutation is a sequence difference relative to SEQ ID NO: 1.

9. The method of claim 8, wherein amplification is performed by a polymerase chain reaction.

10. The method of claim 8, wherein the PKD1 polynucleotide is a variant PKD1 polynucleotide.

11. The method of claim 10, wherein the variant PKD1 polynucleotide comprises a nucleotide sequence substantially identical to SEQ ID NO:1, wherein nucleotide 474 is a T; nucleotide 487 is an A; nucleotide 4884 is an A; nucleotide 6058 is a T; nucleotide 6195 is n A; nucleotide 7376 is a C; nucleotide 7696 is a T; nucleotide 8021 is an A; nucleotide 9367 is a T; nucleotide 10143 is a G; nucleotide 10234 is a C; or nucleotide 10255 is a T.

12. The method of claim 8, wherein identifying the presence or absence of a mutation in the second amplification product comprises determining the nucleotide sequence of the second amplification product.

13. The method of claim 8, wherein identifying the presence or absence of a mutation in the second amplification product comprises determining the melting temperature of the second amplification product, and comparing the melting temperature to the melting temperature of a corresponding portion of SEQ ID NO:1.

14. The method of claim 8, wherein identifying the presence or absence of a mutation in the second amplification product is performed using denaturing high performance liquid chromatography.

15. The method of claim 8, wherein identifying the presence or absence of a mutation in the second amplification product is performed using matrix-assisted laser desorption time of flight mass spectrometry.

16. The method of claim 8, wherein identifying the presence or absence of a mutation in the second amplification product is performed using high throughput conformation-sensitive gel electrophoresis.

17. The method of claim 8, wherein identifying the presence or absence of a mutation in the second amplification product is performed by a method selected from single stranded conformation analysis, denaturing gradient gel electrophoresis, an RNAse protection assay, allele-specific oligonucleotide detection, an allele-specific polymerase chain reaction, and an oligonucleotide ligation assay.

18. The method of claim 8, wherein identifying the presence or absence of a mutation in the second amplification product is performed using a primer extension reaction assay,
wherein the primer extension reaction is performed using a detectably labeled primer and a mixture of deoxynucleotides and dideoxynucleotides, and
wherein the primer and mixture are selected so as to enable differential extension of the primer in the presence of a wild type PKD1 polynucleotide as compared to a mutant PKD1 polynucleotide.

19. The method of claim 8, wherein the method is performed in a high throughput format using a plurality of samples.

20. The method of claim 19, wherein plurality of samples are in an array.

21. The method of claim 20, wherein the array comprises a microtiter plate.

22. The method of claim 20, wherein the array is on a microchip.

23. The method of claim 8, wherein prior to identifying the presence or absence of a mutation in the second amplification product, the second amplification product is serially diluted to remove genomic contamination.

24. The method of claim 8, wherein a second primer for the first amplification product are selected from the group consisting of SEQ ID NOs: 4 and 6.

25. The method of claim 8, wherein the primers for the second amplification product are selected from the group consisting of SEQ ID NOs: 19, 20, 21, and 22.

26. The method of claim 8, wherein the contacting step includes using a set of primer pairs to amplify multiple first amplification products, wherein said set of primers selectively hybridize to SEQ ID NO: 1 and amplify portions of SEQ ID NO: 1 comprising about 2043 to 4209; nucleotides 17907 to 22489; nucleotides 22218 to 26363; nucleotides 26246 to 30615; nucleotides 30606 to 33957; nucleotides 36819 to 37140; nucleotides 37329 to 41258; and nucleotides 41508 to 47320, or to a nucleotide sequence complementary to said sequence of SEQ ID NO: 1.

27. The method of claim 26, wherein said set of primer pairs comprises SEQ ID NO: 3 and 4; SEQ ID NO: 5 and 6; SEQ ID NO: 7 and 8; SEQ ID NO: 9 and 10; SEQ ID NO: 11 and 12; SEQ ID NO: 13 and 14; SEQ ID NO: 15 and 16; and SEQ ID NO: 17 and 18.

28. The method of claim 8, wherein the mutation is at a position selected from the group consisting of positions 3110, 3336, 3707, 4168, 6078, 6089, 6326, 7205-7211, 7415, 7433, 7535-7536, 7883, 8159-8160, 8298, 9164, 9213, and 9326 of SEQ ID NO: 1.

* * * * *